United States Patent
Moro et al.

(10) Patent No.: US 7,811,605 B2
(45) Date of Patent: *Oct. 12, 2010

(54) METHOD OF FORMATION OF SHAPE-RETENTIVE AGGREGATES OF GEL PARTICLES AND THEIR USES

(75) Inventors: Daniel G. Moro, Dallas, TX (US); John V. St. John, Grapevine, TX (US); Kevin F. Shannon, Irving, TX (US); Bill C. Ponder, Colleyville, TX (US)

(73) Assignee: ULURU Inc., Addison, TX (US)

( * ) Notice: Subject to any disclaimer, the term of this patent is extended or adjusted under 35 U.S.C. 154(b) by 1306 days.

This patent is subject to a terminal disclaimer.

(21) Appl. No.: 10/960,461

(22) Filed: Oct. 6, 2004

(65) Prior Publication Data

US 2005/0118270 A1    Jun. 2, 2005

Related U.S. Application Data

(63) Continuation-in-part of application No. 10/289,756, filed on Nov. 6, 2002, now Pat. No. 7,351,430.

(51) Int. Cl.
*A61K 9/00* (2006.01)
*A61K 9/14* (2006.01)
*A61K 9/16* (2006.01)
*G02C 7/04* (2006.01)

(52) U.S. Cl. ............ 424/489; 424/400; 424/422; 424/427; 424/429; 424/501

(58) Field of Classification Search ............ None
See application file for complete search history.

(56) References Cited

U.S. PATENT DOCUMENTS 3,822,089 A    7/1974    Wichterle (Continued)

FOREIGN PATENT DOCUMENTS

CA    2195373    7/1997

(Continued)

OTHER PUBLICATIONS

Zeta-Meter, Inc. Zeta Potential: A Complete Course in 5 Minutes. Accessed from http://www.zeta-meter.com/5min.pdf via the Wayback Machine (Jun. 6, 2001).*

(Continued)

*Primary Examiner*—David J Blanchard
*Assistant Examiner*—Rachael E Welter
(74) *Attorney, Agent, or Firm*—Antoinette F. Konski; Foley & Lardner LLP

(57) ABSTRACT

The present invention relates to a method of forming shape-retentive aggregates of gel particles in which the aggregates are held together by non-covalent bond physical forces such as, without limitation, hydrophobic-hydrophilic interactions and hydrogen bonds. The method comprises introducing a suspension of gel particles in a polar liquid at a selected concentration, wherein the gel particles have an absolute zeta potential, into a medium in which the absolute zeta potential of the gel particles is decreased, resulting in the gel particles coalescing into the claimed shape-retentive aggregate. This invention also relates to uses of the method of formation of the shape-retentive aggregates of gel particles.

46 Claims, 18 Drawing Sheets

Schematic showing hydrogel particle aggregate formation.

Hydrogel Nanoparticles         Nanoparticle Aggregate

U.S. PATENT DOCUMENTS

| | | | |
|---|---|---|---|
| 3,948,841 | A | 4/1976 | Dusek |
| 3,951,925 | A | 4/1976 | Mishima et al. |
| 3,963,685 | A | 6/1976 | Abrahams |
| 4,272,518 | A | 6/1981 | Moro et al. |
| 4,542,176 | A | 9/1985 | Graham |
| 4,962,133 | A | 10/1990 | Chromecek et al. |
| 5,045,266 | A | 9/1991 | Moro et al. |
| 5,122,544 | A * | 6/1992 | Bailey et al. ............... 521/40.5 |
| 5,266,325 | A | 11/1993 | Kuzma et al. |
| 5,292,515 | A | 3/1994 | Moro et al. |
| 5,468,811 | A | 11/1995 | Moro et al. |
| 5,536,508 | A | 7/1996 | Canal et al. |
| 5,632,774 | A | 5/1997 | Babian |
| 5,770,631 | A | 6/1998 | Fukutomi et al. |
| 5,840,338 | A | 11/1998 | Roos et al. |
| 5,871,722 | A | 2/1999 | Nacht et al. |
| 5,945,457 | A | 8/1999 | Plate et al. |
| 6,068,859 | A | 5/2000 | Curatolo et al. |
| 6,306,177 | B1 | 10/2001 | Felt et al. |
| 6,521,431 | B1 | 2/2003 | Kiser et al. |
| 6,933,356 | B2 | 8/2005 | Hamamoto et al. |
| 2003/0093157 | A1* | 5/2003 | Casares et al. ........... 623/23.73 |
| 2003/0138490 | A1 | 7/2003 | Hu et al. |
| 2004/0086548 | A1 | 5/2004 | St. John et al. |
| 2005/0118270 | A1 | 6/2005 | Moro et al. |
| 2008/0063716 | A1 | 3/2008 | Moro et al. |

FOREIGN PATENT DOCUMENTS

| | | |
|---|---|---|
| EP | 0 785 224 B1 | 1/1997 |
| EP | 1 447 074 A2 | 8/2004 |
| GB | 1 263 873 | 2/1972 |
| JP | 49-50089 | 5/1974 |
| JP | 53040038 A | 4/1978 |
| JP | 58-331 | 1/1983 |
| JP | 58149910 A | 9/1983 |
| JP | 05247225 A | 9/1993 |
| JP | 9-25303 | 1/1997 |
| JP | 9-208710 | 8/1997 |
| JP | 2001-517494 | 10/2001 |
| JP | 2002284882 A | 10/2002 |
| JP | 2002302616 | 10/2002 |
| JP | 2003261777 A | 9/2003 |
| WO | WO 99/15211 A1 | 4/1999 |
| WO | WO 03/026537 A1 | 4/2003 |
| WO | WO 2006/041967 A1 | 4/2006 |

OTHER PUBLICATIONS

Ruckenstein et al, Polymerization in gel-like emulsions, J. of Applied Polymer Science, vol. 36, pp. 907-923, 1988.* am Ende, et al., "Transport of ionizable drugs and proteins in crosslinked poly(acrylic acid) and poly(acrylic acid-co-2-hydroxyethyl methacrylate)" *Journal of Controlled Release* (1997) 48:47-56.

Ayhan, F. et al., "Optimization of urease immobilization onto non-porous HEMA incorporated poly(EGDMA) microbeads and estimation of kinetic parameters" *Bioresource Technology* (2002) 81:131-140.

Beers, K. L. et al., "Atom Transfer Radical Polymereization of 2-Hydroxyethyl Methacrylate" *Macromolecules* (1999) 32:5772-5776.

Bouillaguet, S. et al., "Effect of sub-lethal concentrations of HEMA (2-hydroxyethyl methacrylate) on THP-1 human monocyte-macrophages, in vitro" *Dental Materials* (2000) 16:213-217.

Brahim, S. et al., "Kinetics of glucose oxidase immobilized in p(HEMA)-hydrogel microspheres in a packed-bed bioreactor" *Journal of Molecular Catalysis B: Enzymatic* (2002) 18:69-80.

Brier-Russell, D. et al., "In Vitro Assessment of Interaction of Blood with Model Surfaces: Acrylates and Methacrylates" *Journal of Colloid and Interface Science* (1981) 81:311-318.

Dalton, P. D. et al., "Manufacture of poly(2-hydroxyethyl methacrylate-co-methyl methacrylate) hydrogel tubes for use as nerve guidance channels" *Biomaterials* (2002) 23:3843-3851.

Debord, J.D. et al., "Thermoresponsive Photonic Crystals" *The Journal of Physical Chemistry* (2000) 104(27):6327-6331.

Denizli, A. et al., "Monosize and non-porous p(HEMA-co-MMA) microparticles designed as dye- and metal-chelate affinity sorbents" *Colloids and Surfaces A: Physicochemical and Engineering Aspects* (2000) 174:307-317.

Dziubla, T. D. et al., "Evaluation of porous networks of poly(2-hydroxyethyl methacrylate) as interfacial drug delivery devices" *Biomaterials* (2001) pp. 2893-2899.

Frutos, P. et al., "Release of gentamicin sulphate from a modified commercial bone cement. Effect of of (2-hydroxyethyl methacrylate) comonomer and poly(N-vinyl-2-pyrrolidone) additive on release mechanism and kinetics" *Biomaterials* (2002) 23:3787-3797.

Gallardo, A. et al., "Controlled release of cyclosporine from VP-MEMA copolymer systems of adjustable resorption monitorized by MEKC" *Biomaterials* (2000) 21:915-921.

Gallardo, A. et al., "Modulated release of cyclosporine from soluble vinyl pyrrolidone-hydroxyethyl methacrylate copolymer hydrogels A correlation of 'In vitro' and 'in vivo' experiments" *Journal of Controlled Release* (2001) 72:1-11.

Garrett, Q. et al., "Effect of charged groups on the adsorption and penetration of proteins onto and into carboxymethylated poly(HEMA) hydrogels" *Biomaterials* (1998) 19:2175-2186.

Graham, N. B. et al., "Nanogels and microgels: The new polymeric materials playground" *Pure & Appl. Chem.* (1998) 70(6):1271-1275.

Hacioglu, B. et al., "Polymerization kinetics of HEMA/DEGDMA: using changes in initiation and chain transfer rates to explore the effects of chain-length-dependent termination" *Biomaterials* (2002) 23:4057-4064.

Horak, D. et al., "Hydrogels in endovascular embolization" *Biomaterials* (1997) 18:1355-1359.

Hsiue, G. et al., "Poly(2-hydroxyethyl methacrylate) film as a drug delivery system for pilocarpine" *Biomaterials* (2001) 22:1763-1769.

Hu, Z. et al., "Polymer Gel Nanoparticle Networks" *Advanced Materials* (2000) 12(16):1173-1176.

Hutcheon, G.A. et al., "Water absorption and surface properties of novel poly(ethylmethacrylate) polymer systems for use in bone and cartilage repair" *Biomaterials* (2001) 22:667-676.

Klisch, J. et al., "Combined stent implantation and embolization with liquid 2-polyhydroxyethyl methacrylate for treatment of experimental canine wide-necked aneurysms" *Interventional Neuroradiology* (2002) 44:503-512.

Lesny, P. et al., "Polymer hydrogels usable for nervous tissue repair" *Journal of Chemical Neuroanatomy* (2002) 23:243-247.

Liu, Q. et al., "Preparation of macroporous poly(2-Hydroxyethyl methacrylate) hydrogels by enhanced phase separation" *Biomaterials* (2000) 21:2163-2169.

Lyon, L. A. et al., "Responsive Microgel Photonic Crystals" *Polymer Preprints* (2002) 43:24-25.

Lyon, L. A. et al., "Tunable Kinetics of Core-Shell Microgel Volume Phase Transitions" *Polymer Preprints* (2002) 43:363-364.

Noda, M. et al., "Sublethal, 2-week exposures of dental material components alter TNF-α secretion of THP-1 monocytes" *Dental Materials* (2003) pp. 1-5.

Nojiri, C. et al., "Nonthrombogenic Polymer Vascular Prosthesis" *Artificial Organs* (1995) 19(1):32-38.

Pashley, D. H. et al., "Permeability of demineralized dentin to HEMA" *Dental Materials* (2000) 16:7-14.

Ramakrishna, S. et al., "Biomedical applications of polymer-composite materials: a review" *Composites Science and Technology* (2001) 61:1189-1224.

Reichl, F. X., "Biological clearance of HEMA in guinea pigs" *Biomaterials* (2002) 23:2135-2141.

Robinson, K. L., "Controlled Polymerization of 2-Hydroxyethyl Methacrylate by ATRP at Ambient Temperature" *Macromolecules* (2001) 34:3155-3158.

Rogach, A. L. et al., "Electrophoretic Deposition of Latex-Based 3D Colloidal Photonic Crystals: A Technique for Rapid Production of High-Quality Opals" *Chem Mater.* (2000) 12:2721-2726.

Sefc, L. et al., "Development of hydrogel implants for urinary incontinence treatment" *Biomaterials* (2002) 23:3711-3715.

Sefton, M. V. et al., "Making microencapsulation work: conformal coating, immobilization gels and in vivo performance" *Journal of Controlled Release* (2000) 65: 173-186.

Seidel, J. M. et al., "Synthesis of PolyHEMA Hydrogels for Using as Biomaterials" *Materials Research* (2000) 3(3):79-83.

Tanaka, M. et al., "Study on kinetics of early stage protein adsorption on poly(2-methoxyethylacrylate) (PMEA) surface" *Colloids and Surfaces A: Physicochemical and Engineering Aspects/* (2002) 203:195-204.

Tanaka, M. et al., "Blood compatible aspects of poly(2-methoxyethylacrylate) (PMEA)—relationship between protein adsorption and platelet adhesion on PMEA surface" *Biomaterials* (2000) 21:1471-1481.

Yoshi, E., "Cytotoxic effects of acrylates and methacrylates: Relationships of monomer structures and cytotoxicity" *J. Biomed Mater. Res.* (1997) 37:517-524.

International Search Report issued Mar. 12, 2004 for PCT/US03/35671.

International Preliminary Examination Report issued Jul. 1, 2004 for PCT/US03/35671.

Klein et al. (2003), "Preparation of Monodisperse PMMA Microspheres in Nonpolar Solvents by Dispersion Polymerization with a Macromonomeric Stabilizer," *Colloid Polym. Sci.* 282:7-13.

*Radiation Synthesis and Modification of Polymers for Biomedical Applications* (2002), pp. 1-3, International Atomic Energy Agency, Austria.

Szkurhan & Georges (2004), "Stable Free-Radical Emulsion Polymerization," *Macromolecules* 37:4776-4782.

U.S. Appl. No. 11/581,049, filed Oct. 13, 2006, John V. St. John et al.

U.S. Appl. No. 11/929,534, filed Oct. 30, 2007, John V. St. John et al.

U.S. Appl. No. 11/686,902, filed Mar. 15, 2007, Shannon et al.

Huang et al. (2004) "Controlled drug release from hydrogel nanoparticle networks," *Journal of Controlled Release* 94:303-311.

International Search Report for WO 2006/041967 A1.

Seideli & Malmonge, "Synthesis of PolyHEMA hydrogels for Using as Biomaterials. Bulk and Solution Radical-Initiated Polymerization Techniques" *Mat. Res.* [on line] 2000 (vol. 3, No. 3), pp. 79-83.

Horak et al., "New radiopaque polyHEMA-based hydrogel particles," J. of Biomedical Materials Research, vol. 34, pp. 183-188, 1997.

U.S. Appl. No. 10/289,756 (now U.S. Patent No. 7,351,430)—Notice of Allowance dated Nov. 8, 2007.

U.S. Appl. No. 10/289,756 (now U.S. Patent No. 7,351,430)—Non-Final Office Action dated Jun. 14, 2007.

U.S. Appl. No. 10/289,756 (now U.S. Patent No. 7,351,430)—Advisory Action dated Jan. 29, 2007.

U.S. Appl. No. 10/289,756 (now U.S. Patent No. 7,351,430)—Final Office Action dated Oct. 12, 2006.

U.S. Appl. No. 10/289,756 (now U.S. Patent No. 7,351,430)—Non-Final Office Action dated Apr. 19, 2006.

U.S. Appl. No. 10/289,756 (now U.S. Patent No. 7,351,430)—Final Office Action dated May 17, 2005.

U.S. Appl. No. 10/289,756 (now U.S. Patent No. 7,351,430)—Non-Final Office Action dated Apr. 6, 2004.

U.S. Appl. No. 11/929,531—Non-Final Office Action dated Mar. 19, 2009.

U.S. Appl. No. 11/929,531—Non-Final Office Action dated Jun. 25, 2008.

U.S. Appl. No. 11/929,531—Final Office Action dated Oct. 14, 2009.

Attivi et al. (2005) "Formulation of Insulin-Loaded Polymeric Nanoparticles Using Response Surface Methodology" Drug Development and Industrial Pharmacy 31:179-189.

Jones et al. (2004) "Pharmaceutical Applications of Polymers for Drug Delivery" Sherwebury:Rapra Technology Ltd., eBook, p. 38.

Lanza et al. (1996) "Encapsulated cell technology" Nature Biotechnology 14:1107-1111.

Tauer et al. (2005) "On the preparation of stable poly(2-hydroxyethyl methacrylate) nanoparticles" Colloid Polym. Sci. 283:351-358.

Zhou & Chu (1998) "Synthesis and Volume Phase Transition of Poly(methacrylic acid-*co*-N-isopropylacrylamide) Microgel Particles in Water" J. Phys. Chem. B 102:1364-1371.

U.S. Appl. No. 11/581,049—Non-Final Office Action dated Dec. 15, 2009.

\* cited by examiner

A pHEMA particle aggregate implant 7 days post injection.

The implant in the photograph is the white, half moon-shaped disk at the top center of the open tissue in the mouse.

Size Distributions of pHEMA Nano-particles Determined
By LLS During TFF Concentration of the Particles from
Wet Wts. of [36 mg/mL]$_i$ to [424 mg/mL]$_f$ Effect of Ionic Strength on the Zeta Potential
SDS Stablized pHEMA Nanoparticles

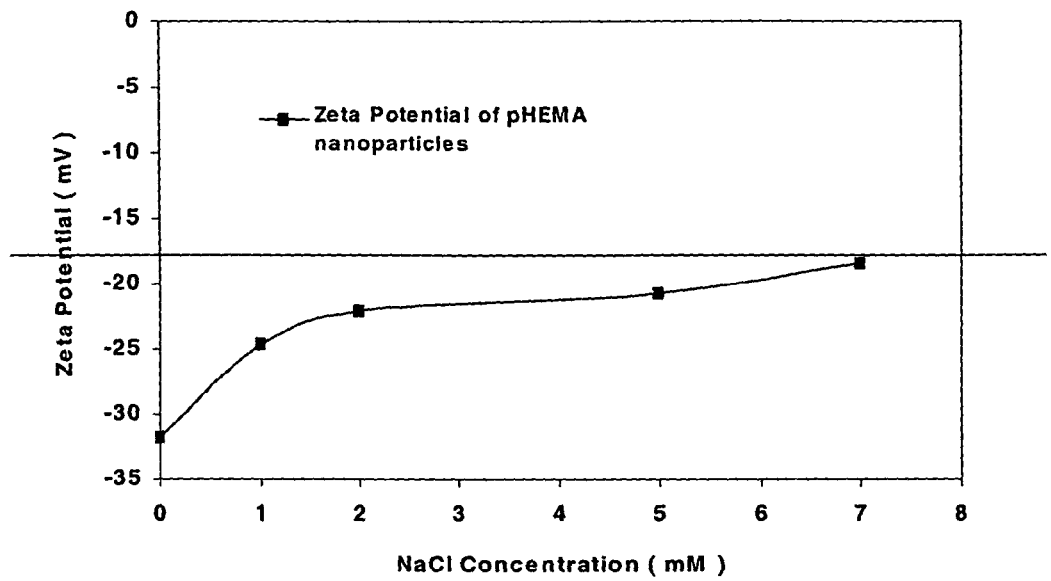
Figure 11.
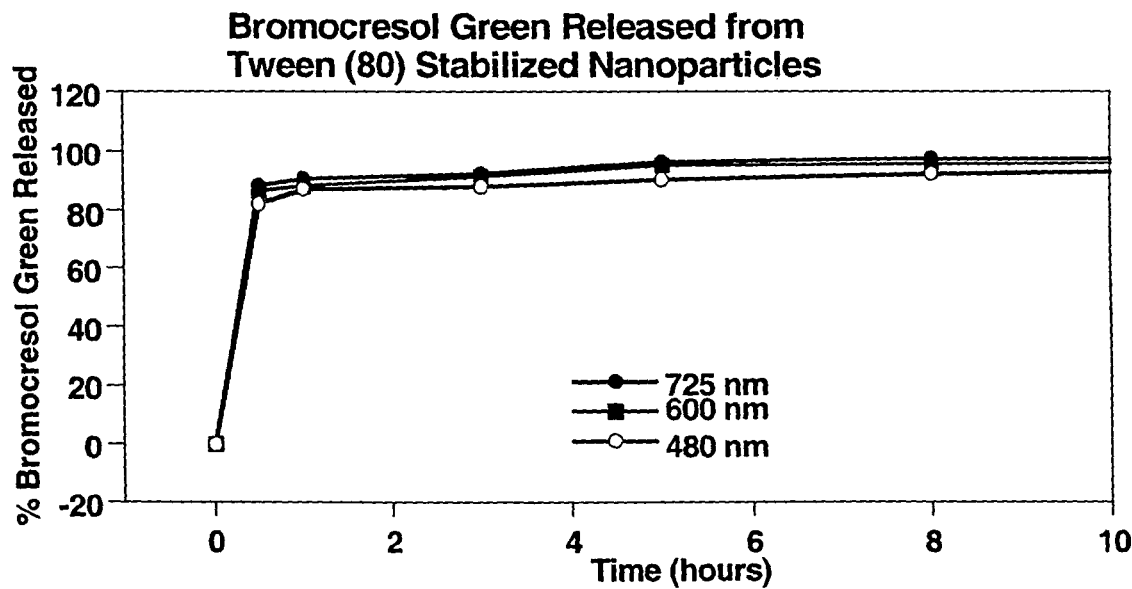

Release Profiles for 5 mg FITC-BSA (72 kDa) from 500 mg pHEMA Nanoparticle Aggregate Depots Formed on Injection into PBS, T = 37 °C Release Profiles for 10 mg FITC-Dextran (2000 kDa) from 500 mg pHEMA Nanoparticle Aggregate Depots Formed on Injection into PBS, T = 37 °C Release Profiles for 20 mg FITC-Dextran (2000 kDa) from 500 mg pHEMA Nanoparticle Aggregate Depots Formed on Injection into PBS, T = 37 °C Release of FITC-BSA (72 kDa) from 500 mg of pHEMA Nanoparticle Aggregates, T = 23 °C Schematic showing hydrogel particle aggregate formation.

Hydrogel Nanoparticles → Nanoparticle Aggregate

METHOD OF FORMATION OF SHAPE-RETENTIVE AGGREGATES OF GEL PARTICLES AND THEIR USES

This application is a continuation-in-part of U.S. patent application Ser. No. 10/289,756, filed Nov. 6, 2002, now U.S. Pat. No. 7,351,430, issued Apr. 1, 2008, which is incorporated by reference, including all drawings, as if fully set forth herein.

FIELD OF THE INVENTION

This invention relates to the fields of organic chemistry, physical chemistry, polymer chemistry, pharmaceutical chemistry, medicine and material science.

BACKGROUND OF THE INVENTION

The discussion that follows is provided as background to aid the reader in understanding the present invention and is not intended, nor is it to be construed, as being prior art to the invention.

A gel is a three-dimensional polymeric network that has absorbed a liquid to form a stable, usually soft and pliable, composition having a non-zero shear modulus. When the liquid absorbed by a gel is water, the gel is called a hydrogel. Water may comprise a significant weight percent of a hydrogel. This, plus the fact that many hydrogel-forming polymers are biologically inert, makes hydrogels particularly useful in a wide variety of biomedical applications.

For example, hydrogels are widely used in soft contact lens. They are also used as burn and wound dressings, with and without incorporated drugs that can be released from the gel matrix to aid in the healing process (e.g., see U.S. Pat. Nos. 3,063,685 and 4,272,518). Hydrogels have been used as coatings to improve the wettability of the surfaces of medical devices such as blood filters (U.S. Pat. No. 5,582,794). They have also found utility as devices for the sustained release of biologically active substances. For example, U.S. Pat. No. 5,292,515 discloses a method of preparing a hydrophilic reservoir drug delivery device. The '515 patent discloses that drug release rates can be controlled by changing the water content of the hydrogel subcutaneous implant, which directly affects its permeability coefficient.

In all the above applications, the gel or hydrogel is in bulk form, that is, it is an amorphous mass of material with no discernable regular internal structure. Bulk hydrogels have slow swelling rates due to the large internal volume relative to the surface area through which water must be absorbed. Furthermore, a substance dissolved or suspended in the absorbed water will diffuse out of the gel at a rate that depends on the distance it must travel to reach the surface of the gel. That is, molecules near the surface of the hydrogel will escape quickly, whereas molecules deeper within the matrix will take a much longer time to reach the outer surface of the gel. This situation can be ameliorated to some extent by using particulate gels. If each particle is sufficiently small, substances dispersed in the particles will diffuse to the surface and be released at approximately the same time.

Particulate gels can be formed by a number of procedures such as direct or inverse emulsion polymerization (Landfester, et al., Macromolecules, 2000, 33:2370) or they can be created from bulk gels by drying the gel and then grinding the resulting xerogel to particles of a desired size. The particles can then be re-solvated to form particulate gels. Particles having sizes in the micro ($10^{-6}$ meters (m)) to nano ($10^{-9}$ m) diameter range can be produced by this means. Molecules of a substance occluded by particles in these size ranges will all have about the same distance to travel to reach the outer surface of the particle and will exhibit near zero-order release kinetics. However, particulate gels have their problems. For instance, it is difficult to control the dissemination of the particles to, and localization at, a selected target site. Furthermore, while bulk hydrogels can be rendered shape-retentive, making them useful as biomaterials in a variety of medical applications, currently available particulate gels, cannot.

U.S. Pat. No. 7,351,430, discloses a shape-retentive aggregate formed from hydrogel particles, thus combining the shape-retentiveness of bulk hydrogels with the substance release control of particulate gels. The '430 Patent discloses a method of forming the shape-retentive aggregate comprising preparing a suspension of hydrogel particles in water and concentrating the suspension until the particles coalesce into a shape-retentive aggregate held together by non-covalent bond physical forces including but not limited hydrophobic/hydrophilic interactions and hydrogen bonds.

It would be useful to have a method of forming shape-retentive gel aggregates in situ, such that the shape of the aggregate would be dictated by the shape of the locus of application. This would be particularly useful where the locus application is in vivo, e.g., biomedical applications such as joint reconstruction, wound repair, drug delivery and cosmetic surgery. The present invention provides such a method.

SUMMARY OF THE INVENTION

Thus, in one aspect the present invention relates to a method for forming a shape-retentive aggregate of gel particles, comprising:

providing a suspension system comprising a plurality of gel particles dispersed in a polar liquid or a mixture of two or more miscible liquids, at least one of which is polar, wherein the gel particles have a first absolute zeta potential; and, introducing the suspension system through an orifice at a selected introduction rate into a receiving medium wherein the gel particles acquire a second absolute zeta potential which is lower (closer to zero) than the first absolute zeta potential whereupon the gel particles coalesce into a shape-retentive aggregate held together by non-covalent bond physical forces comprising hydrophobic-hydrophilic interactions and hydrogen bonds.

In an aspect of this invention, the gel particles are at a concentration of from about 1 to about 500 mg wet weight/mL in the suspension system.

In an aspect of this invention, the gel particles are at a concentration of from about 25 to about 250 mg wet weight/mL in the suspension system.

In an aspect of this invention the plurality of gel particles is of one size, one or more chemical compositions and a narrow polydispersivity.

In an aspect of this invention the plurality of gel particles is of two or more different sizes, the composition of each different size being the same as, or different than, the composition of each of the other different sizes, all sizes being of narrow polydispersivity.

In an aspect of this invention the plurality of gel particles comprises one or more chemical compositions and broad polydispersivity.

In an aspect of this invention the plurality of gel particles are at a concentration in the suspension system that results in cluster formation.

In an aspect of this invention the concentration of gel particles in the suspension system is from about 300 mg wet weight/mL to about 500 mg wet weight/mL.

In an aspect of this invention providing a suspension system comprises:
providing a polymerization system comprising a monomer, or two or more different monomers, wherein the monomer or at least one of the two or more monomers comprise(s) one or more hydroxy and/or one or more ether groups, in a polar liquid or mixture of polar liquids, wherein the polar liquid or at least one of the two or more polar liquids comprise(s) one or more hydroxy groups;
adding from 0.01 to 10 mol percent of a surfactant to the polymerization system; and,
polymerizing the monomer(s) to form a plurality of gel particles, each particle comprising a plurality of polymer strands.

In an aspect of this invention providing a suspension system comprises mixing together preformed dry gel particles, the liquid(s) and the surfactant.

In an aspect of this invention the orifice comprises a hollow needle.

In an aspect of this invention the hollow needle is selected from the group consisting of 10-gauge to 30 gauge needles.

In an aspect of this invention the hollow needle is selected from the group consisting of 15-gauge to 27-gauge needles.

In an aspect of this invention the selected introduction rate is from about 0.05 ml/ minute to about 15 ml/minute.

In an aspect of this invention the selected introduction rate is from about 0.25 ml/minute to about 10 ml/minute.

In an aspect of this invention the receiving medium is an in vivo medium.

In an aspect of this invention the in vivo medium comprises a bodily tissue.

In an aspect of this invention the bodily tissue is selected from the group consisting of epithelium, connective, muscle and nerve.

In an aspect of this invention the connective tissue is selected from the group consisting of blood, bone and cartilage.

In an aspect of this invention the monomer(s) are selected from the group consisting of a 2-alkenoic acid, a hydroxy(2C-4C)alkyl 2-alkenoate, a hydroxy(2C-4C)alkoxy(2C-4C)alkyl 2-alkenoate, a (1C-4C)alkoxy(2C-4C)alkoxy(2C-4C)alkyl 2-alkenoate and a vicinyl epoxy(1C-4C)alkyl 2-alkenoate and a combination of two or more thereof.

In an aspect of this invention the monomer(s) are selected from the group consisting of acrylic acid, methacrylic acid, 2-hydroxyethyl acrylate, 2-hydroxyethylmethacrylate, diethyleneglycol monoacrylate, diethyleneglycol monomethacrylate, 2-hydroxypropyl acrylate, 2-hydroxypropyl methyacrylate, 3-hydroxypropyl acrylate, 3-hydroxypropyl methacrylate, dipropylene glycol monoacrylate, dipropylene glycol monomethacrylate, gylcidyl methacrylate, 2,3-dihydroxypropyl methacrylate, glycidyl acrylate and glycidyl methacrylate and a combination of two or more thereof.

In an aspect of this invention the monomer(s) are selected from the group comprising 2-hydroxyethyl methacrylate, 2-hydroxypropyl methacrylate, 3-hydroxypropyl methacrylate, and a combination of two or more thereof.

In an aspect of this invention the liquid(s) are selected from the group consisting of water, a (1C-10C) alcohol, a (2C-8C) polyol, a (1C-4C)alkyl ether of a (2C-8C)polyol, a (1C-4C) acid ester of a (2C-8C)polyol; a hydroxy-terminated polyethylene oxide, a polyalkylene glycol and a hydroxy(2C-4C) alkyl ester of a mono, di- or tricarboxylic acid.

In an aspect of this invention the liquid(s) are selected from the group consisting of water, methanol, ethanol, isopropyl alcohol, ethylene glycol, diethylene glycol, triethylene glycol, polyethylene glycol 200-600, propylene glycol, dipropylene glycol, 1,4-butanediol, 2,3-butanediol, 1,6-hexanediol, 2,5-hexanediol, ethylene glycol monomethyl ether, ethylene glycol monoethyl ether, methylcellosolve ether, ethylene glycol monoacetate, propylene glycol monomethyl ether, glycerine, glycerol monoacetate, tri(2-hydroxyethyl)citrate, di(hydroxypropyl)oxalate, glycerine, glyceryl monoacetate, glyceryl diacetate, glyceryl monobutyrate and sorbitol.

In an aspect of this invention the liquid is water.

In an aspect of this invention, the method further comprises adding from about 0.1 to about 15% mol percent of a cross-linking agent to the polymerization system which results in cross-linking of the polymer strands.

In an aspect of this invention the cross-linking agent is selected from the group consisting of ethylene glycol diacrylate, ethylene glycol dimethacrylate, 1,4-dihydroxybutane dimethacrylate, diethylene glycol dimethacrylate, propylene glycol dimethacrylate, diethylene glycol dimethacrylate, dipropylene glycol dimethacrylate, diethylene glycol diacrylate, dipropylene glycol diacrylate, divinyl benzene, divinyltoluene, diallyl tartrate, diallyl malate, divinyl tartrate, triallyl melamine, N,N'-methylene bisacrylamide, diallyl maleate, divinyl ether, 1,3-diallyl 2-(2-hydroxyethyl) citrate, vinyl allyl citrate, allyl vinyl maleate, diallyl itaconate, di(2-hydroxyethyl) itaconate, divinyl sulfone, hexahydro-1,3,5-triallyltriazine, triallyl phosphite, diallyl benzenephosphonate, triallyl aconitate, divinyl citraconate, trimethylolpropane trimethacrylate and diallyl fumarate.

In an aspect of this invention the cross-linking agent is selected from the group consisting of a-hydroxy acid esters.

In an aspect of this invention the cross-linked polymer strands have an average molecular weight of from about 3,000 to about 2,000,000.

In an aspect of this invention, the method further comprises adding one or more working substance(s) to the polar liquid(s) of the polymerization system prior to polymerization wherein, after polymerization, a portion of the working substance(s)-containing liquid is occluded by the gel particles to give working substance-containing gel particles.

In an aspect of this invention the working substance-containing gel particles occlude from about 0.1 to about 90 weight percent working substance-containing liquid.

In an aspect of this invention, the method further comprises adding one or more working substance(s) to the suspension system.

In an aspect of this invention, upon formation of the shape-retentive aggregate, from about 0.1 to about 90 weight percent of the working substance(s)-containing-liquid is entrapped within the shape-retentive aggregate.

In an aspect of this invention, the method further comprises:
adding one or more first working substance(s) to the polymerization system to give a first working substance-containing liquid, wherein after polymerization, a portion of the first working substance-containing liquid is occluded by the gel particles;
adding one or more second working substance(s) to the suspension system to give a second working substance-containing liquid, wherein after formation of the shape-retentive aggregate, a portion of the second working substance-containing liquid is entrapped within the shape retentive aggregate: wherein the first working substance(s) may be the same as or different than the second working substance(s) and the liquid of the first working substance-containing liquid may be the same as or different than the liquid of the second working substance-containing liquid.

In an aspect of this invention from 0.1 to 90 weight percent of the first working substance(s)-containing liquid(s) is occluded by the plurality of hydrogel particles and from 0.1 to 90 weight percent of the second working substance(s)-containing liquid(s) is entrapped within the shape-retentive aggregate.

In an aspect of this invention the working substance(s) comprise one or more biomedical agent(s), which may be the same or different.

In an aspect of this invention one or more of the biomedical agent(s) comprise(s) one or more pharmaceutical agent(s).

In an aspect of this invention the pharmaceutical agent(s) further comprises/comprise one or more pharmaceutically acceptable excipient(s).

In an aspect of this invention the pharmaceutical agent(s) comprises/comprise a peptide or a protein.

In an aspect of this invention the pharmaceutical agent(s) is/are useful for the treatment of cancer.

In an aspect of this invention the pharmaceutical agent(s) is/are useful for the treatment of coronary artery disease.

In an aspect of this invention the pharmaceutical agent(s) is/are useful for the treatment of respiratory diseases.

In an aspect of this invention the pharmaceutical agent(s) is/are useful for the treatment of infectious diseases.

In an aspect of this invention the pharmaceutical agent(s) is/are useful for the treatment of ocular disease.

In an aspect of this invention the pharmaceutical agent(s) is/are growth factors.

In an aspect of this invention the biomedical agent(s) comprises/comprise one or more tissue-growth scaffold materials.

In an aspect of this invention the biomedical agent(s) comprises/comprise cosmetic tissue enhancement substances.

In an aspect of this invention the size of the plurality of gel particles is from about 10 to about 75,000 nanometers in diameter.

In an aspect of this invention the size of the plurality of gel particles is from about 10 to about 800 nanometers in diameter.

In an aspect of this invention the gel particles are degradable.

In an aspect of this invention the shape-retentive aggregate is degradable.

In an aspect of this invention the gel particles are degradable and the shape-retentive aggregate is degradable.

In an aspect of this invention the shape-retentive aggregate is elastic.

DETAILED DESCRIPTION OF THE INVENTION

Brief description of the tables

Table 1 shows the effect of reagent concentration on particle size and polydispersity.

Table 2 shows the effect of introduction rate, orifice size and particle concentration on aggregate formation.

Table 3 shows effect of particle size on aggregation using suspensions of pHEMA particles ranging in size from 45 μ to 150 μ.

Table 4 shows the effect of polymer type on the rate of erosion of aggregates composed of hydrogel particles formed from different ratios of HEMA to MM.

Table 5 shows the effect of particle concentration on the formation of particle clusters.

Table 6 shows the zeta potential on different size gel particles.

Table 7 shows the effect of ionic strength on the zeta potential and on the absorbed-water size of pHEMA hydrogel particles.

Table 8 shows the effect of addition of acetone to an aqueous dispersion of PHEMA particles on the size of the particles.

Table 9 shows the effect of addition of ethanol to an aqueous dispersion of pHEMA particles on the size of the particles.

Table 10 shows the effect of particle concentration on zeta potential and particle size in an aqueous dispersion of pHEMA particles.

Table 11 shows the loading efficiency and burst release of FITC-BSA and FITC-dextran from aggregates made from particle dispersions of various particle size when the suspension system comprises water alone and water plus 5% gelatin.

BRIEF DESCRIPTION OF THE FIGURES

FIG. 3 shows the above plot for aggregates composed of particles of different sizes injected into phosphate buffered saline at room temperature.

FIG. 4 shows the above plot for aggregates composed of particles of different sizes injected into phosphate buffered saline at room temperature and 37° C.

FIG. 5 shows the above plot for aggregates composed of particles of different sizes injected into bovine serum at room temperature.

FIG. 6 shows the above plot for aggregates composed of particles injected into hypertonic saline and PBS at room temperature.

FIG. 7 shows the above plot for aggregates composed of particles injected into PBS at room temperature.

FIG. 8 shows the above plot for PHEMA aggregates with either SDS or DSS surfactant at room temperature and 37° C.

FIG. 9 is a plot showing the relationship between particle cluster formation and wet weight of the polymer in suspension.

FIG. 11 is a plot showing the release of bromocresol green dye from aggregates composed of narrow polydispersivity PHEMA particles injected into PBS at room temperature.

DETAILED DESCRIPTION OF THE INVENTION

Definitions

Figure 1:
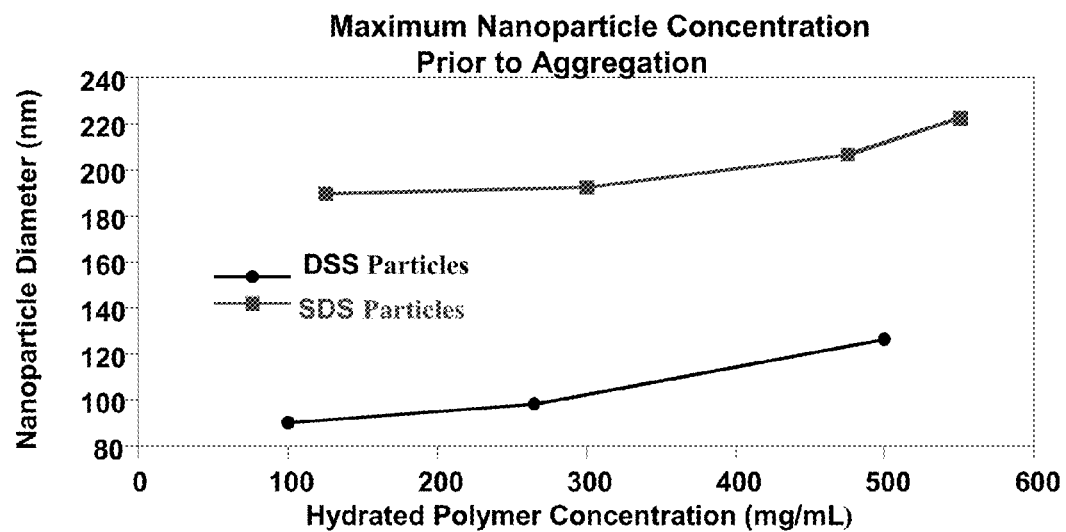
FIG. 1 is a plot showing the relationship of particle diameter in dispersion to the maximum wet weight concentration of particles in suspension before the onset of aggregate formation.

As used herein, the term "gel" refers to a three-dimensional polymeric structure that itself is insoluble in a particular liquid but which is capable of absorbing and retaining large quantities of the liquid to form a stable, often soft and pliable, but always to one degree or another shape-retentive, structure. When the liquid is water, the gel is referred to as a hydrogel. Unless expressly stated otherwise, the term "gel" will be used throughout this application to refer both to polymeric structures that have absorbed a liquid other than water and to polymeric structures that have absorbed water, it being readily apparent to those skilled in the art from the context whether the polymeric structure is simply a "gel" or a "hydrogel."

The term "polar liquid," as used herein has the meaning generally understood by those skilled in the chemical art. In brief, a polar liquid is one in which the electrons are unevenly distributed among the atoms of its molecules and therefore create an electrical dipole. To be polar a molecule must contain at least one atom that is more electronegative than other atoms in the molecule. Examples of polar liquids include, without limitation, water, where the oxygen atom bears a partial negative charge and the hydrogen atoms a partial positive charge, and alcohols, wherein the O—H moiety is similarly polarized.

As used herein, "gel particle" refers to a microscopic or sub-microscopic quantity of a gel in a discrete shape, usually, but not necessarily, spherical or substantially so. As used herein, a "gel particle" includes small clusters of individual particles held together by non-covalent bond physical forces such as hydrophilic/hydrophobic interactions and hydrogen bonding, wherein the clusters do not adversely affect the stability of a gel particle suspension (suspension system) containing them or the performance of the suspension system in the methods of this invention. Clusters result from changes in concentration of gel particles in suspension. That is, at higher concentrations, it is more likely individual particles will get close enough to one another for non-covalent bond forces, which will eventually hold a shape-retentive aggregate of this invention together, to cause them to coalesce.

As used herein, a "suspension" refers to a uniformly distributed, stable dispersion of a solid in a liquid in which the solid is not soluble. A surfactant may be added to the liquid to help stabilize the dispersion. As used herein, a "suspension system" refers to a suspension wherein gel particles of this invention are the dispersed solid. By "stable" is meant that the solid remains uniformly dispersed for at least 24 hours, unless subjected to disrupting external forces such as, without limitation, centrifugation or filtration.

As used herein, a "surfactant" has the meaning generally understood by those skilled in the chemical art. That is, a surfactant is a soluble compound, which may be anionic, cationic, zwitterionic, amphoteric or neutral in charge, and which reduces the surface tension of the liquid in which it is dissolved or that reduces interfacial tension between two liquids or a liquid and a solid.

As used herein, the term "shape-retentive aggregate" refers to a structure composed of a large number of gel particles held together by inter-particle and particle-liquid forces such as, without limitation, hydrophilic/hydrophobic interactions and hydrogen bonding wherein the structure maintains indefinitely whatever shape it may be cut, molded or, in a presently preferred embodiment of this invention, conforms to upon in vivo injection, unless the aggregate or the particles comprising it is/are purposely constructed so as to be degradable.

As used herein, a "degradable" shape-retentive aggregate refers to an aggregate that disintegrates into discrete gel particles (or clusters of particles), upon contact with a selected physical or chemical condition such as, without limitation, temperature, abrasion, pH, ionic strength, electrical voltage and/or current, acidity, basicity, solvent effects and the like.

As used herein, a "degradable" gel particle refers to a gel particle that disintegrates into discrete polymer strands or even partial strands and that loses its spherical or other discrete shape upon contact with a selected physical or chemical condition such as, without limitation, temperature, abrasion, pH, ionic strength, electrical voltage and/or current, acidity, basicity, solvent effects and the like.

As used herein, the term "receiving medium" refers to any medium into which a suspension system of this invention is introduced and in which a shape-retentive aggregate of this invention forms. For the purpose of this invention, the receiving medium is one in which the absolute zeta potential of the individual gel particles is reduced to a level that results in the coalescence of the particles and eventually the formation of a shape-retentive aggregate of this invention.

As used herein, the terms "elastomeric," "elasticity" and "elastic," refer to a shape-retentive aggregate that can be distorted by an external force to at least 150% of its original dimension in any direction and when the force is removed, immediately returns to its approximate original dimension.

As used herein, the term "monomer" has the meaning understood by those skilled in the chemical art. That is, a monomer is a small chemical compound that is capable of forming a macromolecule of repeating units of itself, i.e., a polymer. Two or more different monomers may react to form a polymer in which each of the monomers is repeated numerous times, the polymer being referred to as a copolymer to reflect the fact that it is made up of more than one monomer.

As used herein, the term "size" when used to describe a gel particle of this invention refers to the volume of an essentially spherical particle as represented by its diameter, which of course is directed related to its volume. When referring to a plurality of gel particles, size relates to the average volume of the particles in the plurality as represented by their average diameter.

As used herein, the term "polydispersivity" refers to the range of sizes of the particles in a suspension system. "Narrow polydispersivity" refers to a suspension system in which the size of the individual particles, as represented by their diameters, deviates 10% or less from the average diameter of the particles in the system. If two or more pluralities of particles in a suspension system are both stated to be of narrow polydispersivity, what is meant is that there are two distinct sets of particles wherein the particles of each set vary in diameter by no more than 10% from an average diameter of the particles in that set and the two averages are distinctly different. A non-limiting example of such a suspension system would be one comprising a first set of particles in which each particle has a diameter of 20 nm±10% and a second set of particles in which each particle has a diameter of 40 nm±10%.

As used herein, the term "broad polydispersivity" refers to a suspension system in which the size of the individual particles of a set of particles deviates more than 10% from the average size of the particles of the set.

As used herein, the term "plurality" simply refers to more that one, i.e., two or more.

As used herein, "chemical composition" as it relates to a gel particle of this invention refers to the chemical composition of the monomers that are polymerized to provide the polymer strands of the particle, to the chemical composition and ratios of different monomers if two or more monomers are used to prepare the polymer strands of the particles and/or to the chemical composition and quantity of any cross-linking agent(s) that are used to inter-connect the particle strands.

As used herein, a "particle strand" refers to a single polymer molecule or, if the system in which the strand exists contains a cross-linking agent, two or more inter-connected polymer molecules. The average number of polymer strands that will be cross-linked and the average number of cross-links between any two polymer strands in a particular gel particle will depend on the quantity of cross-linker in the system and on the concentration of polymer strands.

As used herein, the "wet weight" refers to the weight of a gel particle after it has absorbed the maximum amount of a liquid it is capable of absorbing. When it is stated that a particle has occluded from about 0.1 to about 99 weight percent of a working-substance-containing liquid, what is meant is that the working substance-containing liquid makes up from about 0.1 to about 99% of the weight of the particle after occlusion of the substance-containing liquid.

As used herein, a "working substance" refers to any substance that is occluded by a gel particle or entrapped in a shape-retentive aggregate of this invention. Examples of working substances, without limitation, include biomedical agents; biologically active substances such as pharmaceutical agents, genes, proteins, growth factors, monoclonal antibodies, fragmented antibodies, antigens, polypeptides, DNA, RNA and ribozymes; agrichemical agents (herbicides, fungicides, insecticides, plant growth hormones, etc.); radiopaque substances; radioactive substances, pigments; dyes; metals; semiconductors; dopants; chemical intermediates; acids; and, bases.

As used herein, the phrase "pharmaceutical agent" refers to both small molecule and to macromolecular compounds used as drugs. Among the former are, without limitation, antibiotics, chemotherapeutics (in particular platinum compounds and taxol and its derivatives), analgesics, antidepressants, anti-allergenics, anti-arryhthics, anti-inflammatory compounds, CNS stimulants, sedatives, anti-cholinergics, anti-arteriosclerotics, and the like. Macromolecular compounds include, without limitation, monoclonal antibodies (mAbs), Fabs, proteins, peptides, cells, antigens, nucleic acids, enzymes, growth factors and the like. A pharmaceutical agent may be intended for topical or systemic use.

As used herein, a "metal" refers to an element in the Periodic Table of the Elements that is distinguished by its luster, malleability, conductivity and ability to form positive ions. In particular, a metal, for the purposes of this invention, refers to a transition element, i.e., Groups IB, IIB, IIIB (including the rare earth and actinide metals), IVB, VB, VIB, VIIB and VIII of the Period Table.

As used herein, the term "noble metal" refers to gold, silver, platinum, palladium, ruthenium, rhodium and iridium.

As used herein, an "alloy" refers to a substance possessing metallic properties and composed of two or more elements at least one of which must be a metal. Examples of alloys include, but are not limited to, bronze, brass and stainless steel.

As used herein, the term "oxidation state" refers to the charge on a metallic ion, which charge is the result of the loss of electrons by an atom of the element. The "zero oxidation state" or "ground state" is the metal itself with its full complement of electrons. An "oxidation state of one," i.e., usually written as $M^{+1}$, wherein M refers to the metal, connotes a single positive charge equal to the charge on a proton and results from the loss of one electron, an "oxidation state of two," or "$M^{+2}$" connotes a positive charge equal to that of two protons and results from the loss of two electrons, and so on.

As used herein, a "semiconductor" refers to a crystalline element or chemical compound having electrical resistivity values intermediate between those of insulators and those of metals (conductors); i.e., about $10^{-2}$ to $10^9$ ohm-cm. Semiconductors will conduct electricity under some conditions but not others. The best known semiconductor element is silicon. Other examples of semiconductor elements include, but are not limited to, antimony, arsenic, boron, carbon, gemanium, selenium, sulfur and tellurium. Examples, without limitation, of semiconductor compounds include gallium arsenide, indium antimonide and the oxides of most metals.

As used herein "hydroxy" refers to an —OH group.

As used herein, "ether" refers to a chemical compound containing at least one —C—O—C— structural feature.

As used herein, the term "alkyl" refers to a straight or branched chain saturated aliphatic hydrocarbon, i.e., a compound consisting of carbon and hydrogen only. The size of an alkyl in terms of how many carbon atoms it contains is indicated by the formula (aC-bC)alkyl where a and b are integers. For example, a (1C-4C)alkyl refers to a straight or branched chain alkyl consisting of 1, 2, 3 or 4 carbon atoms. An alkyl group may be substituted or unsubstituted.

As used herein, the phrase "voids between the hydrogel particles" refers to the open space generated when essentially spherical gel particles touch at their circumferences when forming shape-retentive aggregates of this invention. The volume of the voids can be approximated as 0.414 times the average radius of the spheres.

As used herein, a "cross-linking agent" refers to a di-, tri-, or tetra-functional chemical entity that is capable of forming covalent bonds with functional groups on polymeric strands resulting in a three-dimensional structure.

A "hydrogen bond" refers to the electronic attraction between a hydrogen atom covalently bonded to a highly electronegative atom and another electronegative atom having at least one lone pair of electrons. The strength of a hydrogen bond, about 23 kJ (kilojoules) $mol^{-1}$, is between that of a covalent bond, about 500 kJ $mol^{-1}$, and a van der Waals attraction, about 1.3 kJ $mol^{-1}$. Hydrogen bonds have a marked effect on the physical characteristics of a composition capable of forming them. For example, ethanol has a hydrogen atom covalently bonded to an oxygen atom, which also has a pair of unshared (i.e., a "lone pair") electrons and, therefore, ethanol is capable of hydrogen bonding with itself. Ethanol has a boiling point of 78° C. In general, compounds of similar molecular weight are expected to have similar boiling points. However, dimethyl ether, which has exactly the same molecular weight as ethanol but which is not capable of hydrogen bonding between molecules of itself, has a boiling point of −24° C., almost 100 degrees lower than ethanol. Hydrogen bonding between the ethanol molecules has made ethanol act as if it were substantially higher in molecular weight.

As used herein, a "charged" gel particle refers to a particle that has a localized positive or negative charge due to ionic content of the monomers making up the polymer strands of the particle and the environment in which these particles find themselves. For example, without limitation, hydrogel particles comprising acrylic acid as a co-monomer will, under basic conditions, exist in a state in which some or all of the acid groups are ionized, i.e., —COOH becomes —COO⁻. Another example is the amino (—$NH_2$) group, which, in an acidic environment, will form an ammonium (—$NH_3^+$) ion.

As used herein, "zeta potential" as used herein had the meaning generally understood by those skilled in the chemical art. Briefly, when a charged particle is suspended in an electrolytic solution, a layer of counter-ions (ions of charge opposite that of the particle) forms at the surface of the particle. This layer of particles is strongly adhered to the surface of the particle and is referred to as the Stern layer. A second, diffuse layer of ions of the same charge as the particle (and opposite the charge of the counter-ions that form the Stern layer, often referred to as co-ions) then forms around the strongly absorbed inner layer. The attached counter-ions in the Stern layer and the charged atmosphere in the diffuse layer are referred to as the "double layer," the thickness of which depends on the type and concentration of ions in solution. The double layer forms to neutralize the charge of the particle. This causes an electrokinetic potential between the surface of the particle and any point in the suspending liquid. The voltage difference, which is on the order of millivolts (mV) is referred to as the surface potential. The potential drops off essentially linearly in the Stern layer and then exponentially in the diffuse layer.

A charged particle will move with a fixed velocity in a voltage field, a phenomenon that is called electrophoresis. Its mobility is proportional to the electrical potential at the boundary between the moving particle and the surrounding liquid. Since the Stern layer is tightly bound to the particle and the diffuse layer is not, the preceding boundary is usually defined as being the boundary between the Stern layer and the diffuse layer, often referred to as the slip plane. The electrical potential at the junction of the Stern layer and the diffuse layer is related to the mobility of the particle. While the potential at the slip plane is an intermediate value, its ease of measurement by, without limitation, electrophoresis and it direct relationship with stability renders it an ideal characterizing feature of the dispersed particles in suspension. It is this potential that is called the zeta potential. The zeta potential can be positive or negative depending on the initial charge on the particle. The term "absolute zeta potential" refers to the zeta potential of a particle absent the charge sign. That is, actual zeta potentials of, for example, +20 mV and −20 mV would both have an absolute zeta potential of 20.

Charged particles suspended in a liquid tend to remain stably dispersed or to agglomerate depending primarily on the balance between two opposing forces, electrostatic repulsion, which favors a stable dispersion, and van der Waals attraction, which favors particle coalescense or "flocculation" as it is sometimes referred to when the particles initially come together. The zeta potential of the dispersed particles is related to the strength of the electrostatic repulsion so a large absolute zeta potential favors a stable suspension. Thus, particles with an absolute zeta potential equal to or greater than about 30 mV tend to form stable dispersions, since at this level the electrostatic repulsion is sufficient to keep the particles apart. On the other hand, when the absolute value of the zeta potential is less than about 30, then van der Walls forces are sufficiently strong to overcome electrostatic repulsion and the particles tend to flocculate.

The zeta potential of a particle of a particular composition in a particular solvent may be manipulated by modifying, without limitation, the pH of the liquid, the temperature of the liquid, the ionic strength of the liquid, the types of ions in solution in the liquid, and the presence, and if present, the type and concentration of surfactant(s) in the liquid.

As used herein, an "excipient" refers to an inert substance added to a pharmaceutical composition to facilitate its administration. Examples, without limitation, of excipients include calcium carbonate, calcium phosphate, various sugars and types of starch, cellulose derivatives, gelatin, vegetable oils and polyethylene glycols. A "pharmaceutically acceptable excipient" refers to an excipient that does not cause significant irritation to an organism and does not abrogate the biological activity and properties of the administered compound.

As used herein, the phrase "useful in the treatment of" means that the pharmaceutical agent is known to either directly or indirectly inhibit, preferably destroy or deactivate, the causal agent of the disease indicated or to at least ameliorate, preferably eliminate, the symptoms of that disease. With regard to cancer, the agent is known to at least increase the average lifespan of affected individuals.

As used herein, the term "cancer" refers to malignant neoplasms, which, in turn relate to a large group of diseases that can arise in virtually any tissue composed of potentially dividing cells. The basic characteristic of cancer is a transmissible abnormality of cells that is manifested by reduced control over growth and function leading to serious life-threatening effects on the host through invasive growth and metastases.

As used herein, "coronary artery disease" refers to a narrowing of the coronary arteries cause by atherosclerosis that, when sufficiently severe, limits, or, in its most serious form completely occludes, the flow of blood to the myocardium (heart muscle).

As used herein, "respiratory disease" refers to a disease in which the lungs do not work properly so that breathing is affected. Examples of respiratory diseases include, without limitation, asthma, tuberculosis, cystic fibrosis and pneumonia. Examples of pharmaceutical agents useful in the treatment of a respiratory disease include, without limitation.

As used herein, "ocular disease" refers to a disease in which the eyes do not function properly so that vision is affected. Examples of ocular diseases include, without limitation, glaucoma, macular degeneration, diabetic retinopathy, and cataracts. Examples of pharmaceutical agents useful in the treatment of ocular diseases include, without limitation.

As used herein, an "infectious disease" refers to any disease transmitted by a microorganism such as, without limitation, a bacterium, a virus, a prion, a fungus, an amoeba or a protozoon. In general, infectious diseases are communicable in nature and may be transmitted from one individual to another and are capable of producing serious illness in the other individual. Examples of pharmaceutical agents useful in the treatment of infectious diseases include, without limitation.

The shape-retentive aggregates of this invention may be manipulated using the disclosures herein so as to be capable of occluding and/or entrapping virtually any pharmaceutical agent presently known, or that may become known, to those skilled in the art as being effective in the treatment and/or prevention of any of the above diseases and all such pharmaceutical agents are within the scope of this invention.

As used herein, the term "about" means±15% of the value modified with the term.

As used herein, the term "ex vivo" refers to any process or procedure being performed outside of a living organism, for instance, without limitation, in a Petri dish, in soil, in surface water, in a liquid organic medium and the like.

As used herein, the term "in vivo" refers to any process or procedure performed within a living organism, which may be a plant or an animal, in particular, in a human being.

As used herein, the term "hydrophilic/hydrophobic interactions" refers to the inter-or intra-molecular association of chemical entities through physical forces, whereby hydrophilic compounds or hydrophilic regions of compounds tend to associate with other hydrophilic compounds or hydrophilic regions of compounds, and hydrophobic compounds or hydrophobic regions of compounds tend to associate with other hydrophobic compounds or hydrophobic regions of compounds.

As used herein, an "orifice" has the meaning generally understood by those skilled in the arts, that is, an opening, in particular with respect to this invention, an opening through which a suspension system of this invention may be passed to control its rate of introduction into another medium.

As used herein, the term "gauge" has the generally understood meaning of those skilled in the medical arts; that is, it refers to the outside diameter of a hollow needle wherein the outside diameter is directly related to the diameter of the lumen of the needle. The higher the gauge, i.e., the larger the number, e.g. "38 gauge," the smaller the outside diameter of the needle and, therefore, the smaller the lumen.

As used herein, the term "occlude" has the meaning generally understood by those skilled in the chemical art, that is, to absorb and retain a substance for a period of time. With regard to this invention, substances may be absorbed by and retained in, i.e. occluded by, gel particles of this invention during their formation.

As used herein, the term "entrapped" refers to the retention for a period of time of a substance in the voids between the gel particles comprising shape-retentive aggregates of this invention.

As used herein, the term "average molecular weight" refers to the weight of individual polymer strands or cross-linked polymer strands of this invention. For the purpose of this invention, average molecular weight is determined by gel permeation chromatography with laser light scattering detection.

As used herein, "growth factors" refer to certain polypeptides that, when bound by growth factor receptors on the surface of cells, stimulate the cells to grow in size and to divide. Growth factor receptors are specific to each growth factor so that only cells that express the exact receptor for a particular growth factor will be stimulated by that growth factor. Examples of growth factors include, without limitation, vascular endothelial growth factor (VEGF), insulin-like growth factor (IGF), fibroblast growth factor (FGF), epidermal growth factor (EGF), hepatocyte growth factor (HGF) and platelet-derived growth factor (PDGF).

As used herein, "tissue scaffold" refers to a highly porous, artificial, three-dimensional extra-cellular matrix that is used in vivo as a framework to which cells can attach and grow to regenerate tissues lost through injury or disease.

As used herein, "cosmetic tissue enhancement" refers to any bodily feature reconstruction or enhancement such as, without limitation, breast reconstruction or enhancement, lip enhancement, wrinkle removal, facial tissue reconstruction, etc.

Discussion

The shape-retentive aggregates of this invention are formed by preparing a suspension system comprising discrete gel particles dispersed in a liquid or mixture of miscible liquids wherein the particles have an absolute zeta potential and then introducing the suspension system into a receiving medium in which the absolute zeta potential of the particles is reduced to the point that the dispersion of particles in the suspension is destabilized and the particles agglomerate into an aggregate of particles. To achieve the reduction in zeta potential to the point where aggregation occurs, the receiving medium may be at a different ionic strength or a different pH than the suspension system and/or it may dilute the effect of a surfactant added to the suspension system to help stabilize the suspension. While the change in zeta potential results in the initial coalescence of the gel particles of this invention, it is their unique physical and chemical characteristics causes them to be held together in a shape-retentive aggregate. That is, the particles of this invention, once coalesced, are held together by strong inter-particle and particle-liquid interactions such as, without limitation, hydrophobic-hydrophilic interactions and hydrogen bonding, the latter by virtue of the face that the at least one of the monomers that is used to create the polymer strands that make up the gel particle of this invention must comprise one or more hydoxy groups and/or one or more ether groups and at least one of the liquid(s) used in the suspension system must comprise at least one hydroxy group.

The chemical composition of the polymers making up the individual gel particles can be manipulated such that the resulting aggregates are stable and do not readily degrade under a wide range of environmental or physiological conditions. On the other hand, the chemical composition of the particles or the chemical environment of the aggregates can be such that the particles or the aggregates or both, will degrade under selected conditions in a predictable and controllable fashion. For example, without limitation, by selecting the appropriate gel particle composition, aggregates that decompose at certain temperatures, pHs, ionic strengths, electric currents and the like, can be constructed. Or additives can be entrapped in the aggregate matrix as it is being formed such that the resulting aggregates will degrade as the additive(s) change(s) structure, composition and/or reactivity upon exposure to variety of environmental and/or physiological conditions.

The gel particles are prepared in a polymerization system that consists of one or more monomers selected generally from those monomers that, on polymerization, provide a polymer that is capable of hydrogen bonding. General classes of monomers that have this capability include, without limitation, hydroxyalkyl 2-alkenoates such as the hydroxy(2C-4C)alkyl methacrylates and the hydroxy(2C-4C)alkyl acrylates; the hydroxy((2C-4C)alkoxy(2C.-4C)alkyl) alkenoates such as 2-hydroxyethoxyethyl acrylate and methacrylate; the (1C-4C)alkoxy(1C-4C)alkyl methacrylates, e.g., ethoxyethyl methacrylate; the 2-alkenoic acids, such as acrylic and methacrylic acid; the (1C-4C)alkoxy(2C-4C)alkoxy(2C-4C)alkyl) alkenoates such as ethoxyethoxyethyl acrylate and methacrylate; the N-vinylpyrrolidones such as the N-mono- and di-(1C-4C)alkyl vinyl pyrrolidones; the 2-alkenamides such as the N-( C-4C) alkyl-2-alkenamides and N,N-di(1C-4C)alkyl-2-alkenamides, for example, the N-(1C-4C)alkylacrylamides, the N-(1C-4C)alkylmethacrylamides, the N,N-di(1C-4C)alkylacrylamides and the N,N-di(1C-4C)alkylmethacrylamides; the dialkylaminoalkyl 2-alkenoates, e.g., diethylaminoethyl acrylate and methacrylate; the vinylpyridines; the vicinal-epoxyalkyl 2-alkenoates such as the vicinal epoxy(1C-4C)alkyl)methacrylates and the vicinal epoxy(1C-4C)alkyl acrylates, and combinations thereof.

Presently preferred monomers include 2-hydroxyethyl acrylate, 2-hydroxyethyl methacrylate, diethylene glycol monoacrylate, diethylene glycol monomethacrylate, 2-hydropropyl acrylate, 2-hydroxypropyl methacrylate, 3-hydroxypropyl acrylate, 3-hydroxypropyl methacrylate, dipropylene glycol monomethacrylate, dipropylene glycol monoacrylate, glycidyl methacrylate, 2,3-dihydroxypropyl methacrylate, N,N-dimethylaminoethyl methacrylate N,N-dimethylaminoethyl acrylate, and mixtures thereof. A presently particularly preferred monomer is 2-hydroxyethyl methacrylate (HEMA).

Co-monomers that are not capable of hydrogen bonding may be added to the polymerization system to modify the physical and chemical characteristics of the resulting gel particles. Examples of co-monomers that may be used in conjunction with the above monomers are, without limitation, acrylamide, N-methylmethacrylamide, N,N-dimethacrylamide, methylvinylpyrrolidone, N,N-dimethylaminoethyl methacrylate N,N-dimethylaminoethyl acrylate, acrylic acid and methacrylic acid.

In addition, non-polymerizing additives such as, without limitation, alkyl alkanoates as exemplified by methyl butyrate, butyl acetate, etc. may be added to the polymerization reaction to further modify the physical and chemical characteristics of the resulting gel particles.

A cross-linking agent also may be added to the polymerization system to strengthen the three-dimensional structure of the resulting gel particles. The cross-linking agent can be non-degradable, such as, without limitation, ethylene glycol diacrylate or dimethacrylate, 1,4-butylene dimethacrylate, diethylene glycol dimethacrylate, propylene glycol dimethacrylate, diethylene glycol dimethacrylate, dipropylene glycol dimethacrylate, diethylene glycol diacrylate, dipropylene glycol diacrylate, divinyl benzene, divinyltoluene, triallyl melamine, N,N'-methylene bisacrylamide, diallyl maleate, divinyl ether, diallyl monoethylene glycol citrate, vinyl allyl citrate, allyl vinyl maleate, divinyl sulfone, hexahydro-1, 3,5-triallyltriazine, triallyl phosphite, diallyl benzene phosphonate, a polyester of maleic anhydride with triethylene glycol, diallyl aconitrate, divinyl citraconate, trimethylolpropane trimethacrylate and diallyl fumarate. Other non-degradable cross-linking agents will become apparent to those skilled in the art based on the disclosures herein and are within the scope of this invention.

On the other hand, a cross-linking agent may be selected that will decompose under selected conditions thus providing a means of preparing degradable gel particles; that is, as the cross-linker degrades, the stability of the polymer strands making up the gel matrix is compromised to the point that the particles simply fall apart. Examples of degradable cross-linking agents include, without limitation, diallyl tartrate, allyl pyruvate, allyl maleate, divinyl tartrate, diallyl itaconate and the ethylene glycol diester of itaconic acid.

Presently preferred degradable cross-linking agents are provided in co-pending U.S. pat. app. Ser. No. 09/338,404, which is incorporated by reference, including any drawings, as if fully set forth herein. These cross-linkers are monomers or oligomers comprised of a molecule having at least two carboxyl groups and at least two cross-linking functional groups. Between at least one of the cross-linking functional groups and one of the carboxyl groups is a biodegradable poly(hydroxyalkyl acid ester) sequence of 1-6 repetitions.

In another embodiment of this invention, rather than preparing the gel particles of this invention ab initio, that is, by polymerizing monomer(s) under appropriate conditions, shape-retentive aggregates may be prepared from bulk polymers. The bulk polymers may be commercial polymers or they may be prepared by conventional polymerization techniques such as, without limitation, solution, suspension and aqueous polymerization. In the latter case, the polymer may then be treated to remove residual monomer and any other undesirable materials before being dried. The prepared or commercial dry, brittle bulk polymer is then broken up by grinding, micro-pulverizing and the like and the fragments are sieved using techniques known in the art to separate particles of different size. Particles in a desired size range are stirred in a selected liquid or combination of liquids, with or without an added surfactant, until they have absorbed as much of the liquid as they can, that is, they have reached their wet weight. The particles are then ready for introduction into a receiving medium to form a shape-retentive aggregate of this invention.

The presently preferred liquid for use in both the polymerization system and the suspension system of this invention is water, in which case, the particles are hydrogel particles.

Certain organic liquids may also be used in the methods of this invention. In general, it is preferred that they have boiling points above about 60° C., preferable above about 200° C. The use of these liquids results in the formation of intricate, tough aggregates. Organic liquids that are particularly useful in forming the aggregates of this invention are water-miscible oxyalkylene polymers, e.g., the polyalkylene glycols, especially those characterized by a plurality of oxyethylene ($—OCH_2CH_2—$) units in the molecule and a boiling point above about 200° C.

Presently preferred organic liquids that may be used in the methods of this invention are biologically inert, non-toxic, polar, water-miscible organic liquids such as, without limitation, ethylene glycol, propylene glycol, dipropylene glycol, butanediol-1,3, butanediol-1,4, hexanediol-2,5, 2-methyl-2,4-pentanediol, heptanediol-2,4, 2-ethyl-1,3-hexanediol, diethylene glycol, triethylene glycol, tetraethylene glycols, and the higher polyethylene glycols and other water-soluble oxyalkylene homopolymers and copolymers having a molecular weight up to about 2000, preferably up to about 1600. For example, without limitation, hydroxy-terminated polymers of ethylene oxide having average molecular weights of 200-1000, water-soluble oxyethyleneoxypropylene polyol (especially glycol) polymers having molecular weights up to about 1500, preferably up to about 1000, propylene glycol monoethyl ether, monoacetin, glycerine, tri(hydroxyethyl) citrate, ethylene glycol monomethyl ether, ethylene glycol monoethyl ether, di(hydroxypropyl) oxalate, hydroxypropyl acetate, glyceryl triacetate, glyceryl tributyrate, liquid sorbitol ethylene oxide adducts, liquid glycerine ethylene oxide adducts, diethylene glycol monomethyl ether, diethylene glycol monoethyl ether, and ethylene glycol diacetate, may be used.

In an embodiment of this invention, hydrogel particles, having nominal sizes in the $10^{-9}$ meters to the $10^{-6}$ m range are produced by redox, free radical or photo-initiated polymerization in water containing a surfactant. In this manner, particles of relatively narrow polydispersivity can be produced. If, for particular application, such as, without limitation, release of a biologically active substance over a long period of time is desired, particles of broad polydiversity may be formed.

If, on the other hand, the goal is sequential release of a drug or burst release at different times rather than continuous release, two or more groups of particles of different sizes but narrow polydispersivity within each size may be used. For example, without limitation, gel particles of different sizes but narrow polydispersivity may be formed using the techniques described herein in separate polymerization systems that contain a particular biologically active substance. The substance-containing particles may then be combined in a single suspension system. Due to the difference in size of the particles, the biologically active substance will be burst-released as different times. Using the same technique but adding a first biologically active substance to one of the polymerization systems and a different biologically active substance to the second polymerization system will result in a suspension system that contains particles that will release their particular active substance at different times, i.e., sequential release.

Prior to introducing a suspension system into a receiving medium, it may be desirable to treat the suspension system to remove unreacted monomer(s), surfactant and non-occluded biologically active substance from the liquid of the suspension system and/or to remove unreacted monomer(s) and surfactant from the water absorbed by the particles. Techniques such as, without limitation, dialysis, extraction or tangential flow filtration may be used to clean up the particles and the suspension system. The suspension system may then be concentrated, if required, prior to aggregate formation. It is presently preferred that the concentration of particles is a suspension system ready for introduction into a receiving system be in the range of about 1 to about 500 mg/mL, more preferably from about 25 to 150 mg/mL. Rather than removing surfactant from the suspension system, it may be desirable to exchange it for a more pharmaceutically acceptable one that the one used during polymerization and initial suspension system formation.

The suspension of purified particles containing the biologically active substance(s) is then introduced into a medium in which the absolute zeta potential of the particles is reduced with the result that the particles coalesce to form a shape-retentive aggregate of this invention, the shape of the aggregate conforming to the shape of the location, where the medium into which the suspension system is introduced, is found.

In general, for in vivo applications such as drug delivery, the location into which the suspension system is introduced will be a bodily tissue which comprises a bodily fluid, for example without limitation, plasma, extracellular, extravascular, dentinal, interstitial, intraocular, transcellular and synovial fluid, blood, serum, and the like. While it is possible to measure the zeta potential of particles intended for a particular application in a representative sample of bodily fluid from the site of that application to be certain that the particles will agglomerate into a shape-retentive aggregate, such should in general not be necessary. That is, suspension systems of this invention will generally be prepared so as to be stable under selected storage conditions but when subjected to physiological conditions of ionicity, pH and the like, will undergo a reduction in zeta potential and subsequent coalescence and aggregation.

Numerous factors will affect the chemical and physical characteristics of the aggregates of this invention. One is the molecular weight of the polymer used to form the individual hydrogel particles. It has been found that hydrogel particles consisting of low molecular weight polymers will generally not form stable, strong aggregates. Thus, higher molecular weight polymers are presently preferred. While the use of cross-linking agents can ameliorate some of the problems associated with low molecular weight polymers, too much cross-linking agent may be detrimental. If the hydrogel particles contain a large amount of cross-linking agent and/or if the cross-linking agent is highly hydrophobic, the resulting polymeric network may not permit optimal absorption of liquid resulting in less desirable aggregates. It is presently preferred that the polymers that comprise the gel particles of this invention have molecular weights in the range of about 3,000 to about 2,000,000 Da. This may be accomplished by selecting an appropriate commercial polymer, by using a polymerization system that gives polymers of in the desired molecular weight range or by including a cross-linker in the polymerization system to join together short polymer strands to reach the desired molecular weight range.

Particle size will also affect the characteristics of aggregates. It has been determined that smaller gel particles will generally absorb liquid more easily and will give a more resilient matrix. Gel particles having sizes, again as characterized by their average diameters, in the range of about 10 to about 75,000 nm, more preferably from about 10 to about 800 nm, are presently preferred.

If a cross-linking agent is used, its chemical composition and the amount used, i.e., the resulting cross-linking density, will affect the characteristics of the particles as previously discussed and thereupon will affect the characteristics of the aggregates formed. The amount of cross-linking agent used in preparing gel particles of this invention is preferably in the range of about 0.001 to about 10, preferably about 0.1 to about 2 mol percent of monomer.

The molecular weight and chemical composition of the suspension liquids used will also affect the resulting aggregates since some liquid is occluded by the particles and some is entrapped in the aggregate. For instance, as noted previously, water is the presently preferred liquid both for the polymerization system and the suspension system. If 5% glycerin or 20% polyethylene glycol is added to the water, the rate of release of occluded or entrapped FITC-BSA and FITC-Dex is substantially altered as shown in the Examples, below.

The concentration of gel particles in the suspension system will affect the characteristics of the resulting aggregate, primarily due to the fact that at higher concentrations the gel particles tend to coalesce into particle clusters that then coagulate into shape retentive aggregates. As noted above, the presently preferred concentration of gel particles in the suspension medium is from about 1 to about 500, more preferably 25 to 150 mg/mL.

Figure 8:
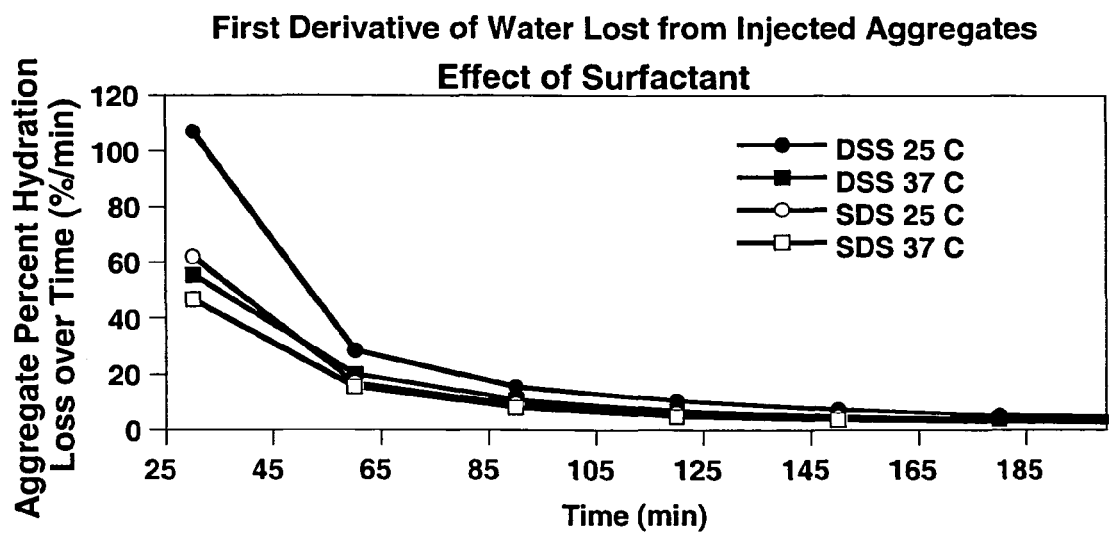

The chemical composition and amount of surfactant used will affect the physical and chemical characteristics of aggregates of this invention. For example, FIG. 8 shows the effect of surfactant choice on the rate of aggregation, which in turn will affect the incorporation of working substances in to the aggregates and the subsequent magnitude of burst release of the incorporated substance(s).

The orifice size and rate of introduction through it of the suspension system into a receiving system will also affect the physical characteristics of the resulting aggregate. In general, using a slow introduction rate and a large aperture will result in the immediate formation of a dense, pliable aggregate with little associated flocculation. A presently preferred means of introduction of a suspension system into a receiving medium is to use a hollow needle of from 10 to 30 gauge, preferably from 15 to 27 gauge, as the aperture and to introduce the suspension system into the receiving medium at a rate of from about 0.05 to about 15 ml/min, more preferably at present from about 0.25 to about 10 ml/min.

The various parameters discussed above are, of course, inter-dependent. For example, without limitation, the physical characteristics of an aggregate are directly proportional to the concentration of hydrogel particles in suspension at a given introduction speed and aperture size. Hydrogel particles at a higher concentration produce a denser, immediate aggregate upon introduction into an aggregation medium as compared to a lower concentration of hydrogel particles in suspension which produce a more diffuse aggregate with associated flocculation. However, too high a concentration can be counterproductive since the particles may no longer be uniformly suspended. Also, maintaining the concentration and size of hydrogel particles in the suspension system, the rate of introduction speed and the aperture size constant, the type and amount of surfactant used affects the aggregation time and quality of the resulting aggregate.

In a presently preferred embodiment of this invention, hydrogel particles are produced by polymerizing non-ionic monomers in water containing a surfactant. The suspension of hydrogel particles is treated to remove unreacted monomer and other impurities. Aggregates are then formed by injecting the suspension into a receiving medium of higher ionic strength, e.g. PBS, serum or other bodily fluid, such that the absolute zeta potential of the particles is lowered and the particles self-assemble into a compact elastic, shape-retentive aggregate. If the medium is in vivo, that is, if it is a bodily tissue, then the shape-retentive aggregate assumes and retains the shape of the region of the body into which it is injected. If the receiving medium is ex vivo, it may be, without limitation, be further pressure-shaped, extruded, or molded into a desired shape, which it will retain so long as the aggregate is maintained in the hydrated state.

In another embodiment of the present invention, monomers having various degrees of ionic character are co-polymerized with non-ionic monomers to form hydrogel particles that are subsequently coalesced into aggregates as above. These aggregates will degrade under appropriate environmental conditions, desirable characteristic for certain applications such as in vivo drug release systems that degrade and clear through the kidneys. That is, the ionic character of the individual hydrogel particles will render them susceptible to degradation depending on the pH, temperature, ionic strength, electric current, etc. of their immediate environment. Breakdown of the individual particles leads to disintegration, or at least loss of structural integrity of the aggregate.

Breakdown of the individual gel particles and thereby breakdown of the aggregate may also be accomplished by using degradable cross-linking agents in the formation of the gel particles. The resulting aggregate will dissemble under environmental conditions that cause degradation of the cross-linker. Cross-linking agents can be prepared that will degrade under selected conditions of, without limitation, pH, temperature, ionic strength, electric current, electromagnetic radiation, radiation and in bodily fluids.

The aggregates of this invention have many uses including, without limitation, delivery of a biologically active substance or substances to a predetermined location. The application may be agricultural, such as, without limitation, the delivery of a fungicide, insecticide or herbicide to a commercial crop; e.g. corn, cotton, soy beans, wheat, etc. Or, the target may be the growth medium, e.g., the soil, in which the crop is growing and may involve the delivery of nutrients and the like. The target may be environmental contaminants in soil, which contaminants may be controllably degraded using aggregates of this invention. The target may be veterinary, involving delivery of medicaments to animals such as reptiles, mammals and birds. In particular, the target may be a human involving the controlled, directed delivery of pharmaceutical agents to the patient.

In an embodiment of this invention, the biologically active agent is dissolved or suspended in an aqueous suspension of hydrated hydrogel particles, which is then introduced into a receiving medium of higher ionic strength to reduce the zeta potential and create an aggregate. While a water-soluble substance is presently preferred to ensure homogeneity of the bulk liquid before injection, such is not necessarily the case. Adjuvants such as surfactants can be added to render a suspension of a limited solubility biologically active substance relatively homogeneous. As the suspension is introduced into the receiving medium and the aggregate forms, the biologically active substance is entrapped in the liquid that fills the voids between the particles of the aggregate.

If produced ex vivo, the resulting resilient, shape-retentive aggregate can be washed to remove any biologically active substance loosely adhered to its surface. The aggregate can then be further shaped for an intended use, if desired. For example, without limitation, if the contemplated use is treatment of an infection, the aggregate could be shaped to fit directly into a wound and to release an antibiotic therein. Likewise, if the use is delivery of a chemotherapeutic, such as, without limitation, paclitaxel or cisplatin, to a target organ in a cancer patient, the aggregate could be shaped to facilitate implantation at the afflicted site.

If the aggregate is produced in vivo, a certain amount of biologically active substance will be entrapped, depending upon the type and size of the biologically active substance and the rate of aggregate formation. The rate of aggregate formation is a function of the particle size and concentration in the suspension system, the absolute zeta potential of the particles in the suspension system and after introduction into the receiving medium, the type and amount of surfactant or combination of surfactants used, the receiving medium, the temperature of the receiving system, the rate of introduction of the suspension system into the receiving medium and the aperture size of the device through which the suspension system is introduced into the receiving medium.

If the in vivo application is delivery of a pharmaceutical agent to a human or animal patient, the presently preferred method of introduction of the suspension system into the receiving medium, that is, a bodily tissue comprising a bodily fluid, is injection using a hypodermic needle. The size of the aperture in the needle may vary and is related to the rate of injection. Presently preferred hypodermic needle sizes are from 10 to 30 gauge, more preferably, 15 to 27 gauge and the rate of injection is from about 0.05 to about 15 milliliters (mL)/minute (min.), more preferably about 0.25 to about 10 ml/min.

The above procedure will result in the formation of a shape-retentive aggregate at the site of injection, the shape-retentive aggregate entrapping the pharmaceutical agent as it is formed and then releasing it over time depending on the properties of the aggregate and active compound.

Another embodiment of this invention involves dissolving or suspending the biologically active agent in the polymerization system prior to polymerization. As the polymerization reaction proceeds and hydrogel particles form, liquid containing the biologically active substance is occluded by the forming particles. Un-occluded biologically active agent is then removed when the particles are treated to remove excess monomer and surfactant. The suspension of biologically active substance-containing particles may then be introduced either ex vivo or in vivo, in the latter case introduction preferably being by injection, into a receiving medium whereupon the particles coalesce into a shape-retentive aggregate.

A combination of the above approaches is an embodiment of this invention. That is, rather than removing the biologically active substance with the excess monomer and surfactant before introduction into the receiving medium, the biologically active agent can be left in the suspension liquid or reintroduced into the suspension system once monomer and surfactant have been removed, so that, upon introduction into the receiving medium, additional active agent will be entrapped in the voids between the particles forming the shape-retentive aggregate.

It is also an embodiment of this invention to remove non-occluded biologically active agent from the suspension system along with the excess monomer and with the surfactant and then add an entirely different biologically active substance to the suspension medium prior to aggregate formation so as to entrap the latter during aggregate formation. The substance entrapped in the voids in the aggregate will normally be released at a very different rate from the substance occluded by the particles. In this manner, a broad range of delivery rates can be achieved. Diversity in delivery profile can also be achieved by varying the chemical composition of the individual hydrogel particles of the aggregate.

If no degradation-inducing chemical modification is incorporated into the individual gel particles and no environmentally activated adjuvant is entrapped in the aggregate, the aggregate formed will be essentially impervious to normal environmental conditions. This type of aggregate will generally display release rates similar to monolithic matrix devices, that is, an initial burst of agent followed by an exponential drop off with time. However, if the gel particles are designed such that they degrade under the environmental conditions encountered at the delivery site and if the biologically active agent will be released from the aggregate only upon disintegration of the particles, extremely fine control of delivery rate is possible. Active agent release only upon disintegration of the gel particles can be achieved by using particles of a size that will result in an aggregate having pores too small for the entrapped active agent to traverse when the aggregate is intact. Similarly, individual particles can be formed such that active substance occluded by them cannot escape unless the particles disintegrate.

In addition to the above, other water soluble substances may be added to a hydrogel particle suspension of this invention to alter the aggregation and disintegration rate of the shape-retentive aggregate formed on introduction into a receiving medium and, therefore, the amount and subsequent release rate of the active agent can be further controlled. Particles comprising cationic and/or anionic charges can be mixed with non-ionic hydrogel particles to provide controlled disintegration of the aggregates under a variety of conditions including the ionic character of the environs or the existence of an external electric charge. The inclusion of charged species may also increase aggregation efficiency due to electrostatic charge interaction.

Using one or more of the above procedures, zero-order, or at least pseudo-zero order, release rates should be attainable for a wide range of biologically active agents.

The type and amount of an agent that can be occluded by a gel particle or entrapped in a shape-retentive aggregate of this invention depends upon a variety of factors. First and foremost, the agent cannot interfere, due to its size, surface charges, polarity, steric interactions, etc., with the formation of discrete gel particles or the coalescence of the gel particles into a shape-retentive aggregate after introduction into a receiving medium, either of which would defeat the purpose of this invention. Once it is determined that the foregoing is not a problem, the size of the hydrogel particles most directly affects the quantity of substance that can be incorporated. The size of the particles themselves will dictate the maximum amount of agent that can be occluded while the polydispersivity of the particles in the suspension solution will affect aggregate pore size. Relatively small agents, such as individual antibiotic molecules, may be entrapped in aggregates formed from small gel particles while substantially larger agents such as monoclonal antibodies, proteins, peptides and other macromolecules will require aggregates made from much larger particles.

Using the methods herein, precise control of delivery kinetics can be achieved. That is, gel particles of differing sizes and chemical compositions can be loaded with a particular agent and, depending on the degradation characteristics of the various particles, the agent can be released over virtually any desired timeframe. In addition, some of the substance might be occluded in the gel particles and some might be entrapped in the voids between particles of the shape-retentive aggregate to provide even more delivery flexibility.

Using the above methods, different agents, even normally incompatible agents, can be loaded into gel particles of this invention and sequentially or simultaneously released. Sequential release will prevent incompatible agents from encountering one another. Simultaneous release permits delivery of two or more non- or minimally bioactive agents that, when combined, form a potent drug. In this manner, the formation of the active species can be postponed until an aggregate containing the precursors has been formed at the site of intended drug activity thereby minimizing side effects.

In another aspect of this invention, gel particles of two or more different sizes and narrow polydispersivity with regard to each different are used at a suspension system concentration in the vicinity of 400 mg wet weight/ml to form shape-retentive aggregates of this invention. The trapping efficiency of substances and their subsequent release rate are substantially different than those of aggregates formed using single size narrow polydispersivity particles. Without being held to any particular theory, it is believed that, upon concentration of a gel particle dispersion to from about 300 to about 500 mg wet weight/ml, preferably from about 400 to about 500 mg wet weight/mL, the particles tend to come close enough to one another for forces favoring coalescence to overcome the forces favoring dispersion. Clusters of particles form in a secondary structure that is still a relatively stable suspension. When a first suspension system comprising a secondary structure of clusters of particles of a first size is mixed with another secondary structure suspension system formed from different size particles and the mixture is introduced into a receiving medium, an intricate and complex shape-retentive aggregate is formed. The shape-retentive aggregate so formed appears to be capable of trapping substances more efficiently than aggregates prepared from single size gel particles. Without being held to any particular theory, it is believed that this may be due to the possibility that, during aggregation in the presence of a substance to be entrapped, the voids between the particles comprising the aggregate are more efficiently filled by mixed polydispersivity particles preventing premature leakage. The examples which follow demonstrate that, for a specific agent of a given size, the size and ratio of sizes of particles comprising an aggregate dramatically affect a forming aggregate's efficiency in trapping an agent and its subsequent release rate. Using this approach, the release rate of a particular substance might be tailored to approach pseudo-zero order kinetics using appropriate particle sizes and ratio of sizes.

Thus, the present invention provides an extremely versatile substance delivery platform, in particular with regard to biologically active agent delivery and most particularly with regard to pharmaceutical agent delivery. A pharmaceutical agent or combination of agents may be delivered continuously over an extended time period, in bursts at specific time intervals, simultaneously after a predetermined delay time so that two or more agents can interact synergistically only after placement of the aggregate containing them at a desired target site, or sequentially so that one agent can act at a target site before the next agent is released or so that two or more agents can synergistically interact.

Another embodiment of this invention is the application of the shape-retentive aggregates of this invention in orthopedic applications such as tissue scaffolding. The macroporous structure of the shape-retentive aggregates of this invention provides a composition that should permit substantial ingrowth, a property not found in typical microporous bulk hydrogels. In addition, the aggregates of this invention exhibit physical properties, such as elastic, shear and bulk moduli, that are significantly improved over those of conventional bulk hydrogels and that, in some cases, approach the properties of articular cartilage. The ability to mold and layer the aggregates of this invention might be used to optimize the release of growth factor at specific locations within a tissue scaffold. Possible orthopedic applications of the methods of this invention include, without limitation, cartilage and bone repair, meniscus repair/replacement, artificial spinal discs, artificial tendons and ligaments, and bone defect filler.

The shape retentive property of the aggregates of this invention and their ability to be formed in and retain water suggest numerous other in vivo uses. For example, a medicated or unmedicated aggregate could be molded into a soft contact lens. A soft, pliable, biocompatible drug delivery device to treat serious eye diseases could be formed by injecting a suspension system of hydrogel particles in which an ocular pharmaceutical agent has been occluded behind the eye. Wound dressings or skin donor site dressings, with or without incorporated antibiotics or other drugs, could be fabricated ex vivo or produced in vivo directly by injection into or onto a wound using the shape-retentive aggregates and methods of this invention. A shape retentive aggregate could be formed in a periodontal pocket by injection of a suspension system of hydrogel particles in which a bone growth factor is either occluded by the particles or entrapped in the forming aggregate. The aggregate might also have within it occluded or entrapped antibiotic for control of infection by sustained delivery of the antibiotic while bone regeneration is being stimulated through the controlled release of the bone growth factor. As an added benefit, the soft, biocompatible shape-retentive aggregate would provide comfort at the site due to its inherent softness and conformability. An aggregate could be formed into an in-dwelling medicated or non-medicated catheter or stent.

Other applications of shape-retentive aggregates prepared by the methods of this invention include using a mixture of particles, some of which will degrade over a predetermined time interval, in applications that require a change in material morphology with time. Also, aggregates composed of a mixture of gel particles with other types of particles, such as metals, semiconductors, non-gel-forming polymers, ceramics, sugars, starches, celluloses and the like can also be produced following the methods of this invention.

The aggregates of this invention produced by the methods hereof might be used as carriers for a host of materials other than biomedical agents. For example, without limitation, metals could be occluded in the gel particles, entrapped by the aggregate or both. The metals would confer varying degrees of conductivity on the aggregates that should have numerous uses. The metals may also be incorporated as ions, that is, metals in oxidation states other than zero. These ions would also confer degrees of conductivity on the aggregates. The gel particles or aggregates of this invention might be infused with semiconductor metals or compounds. Semi-conducting shape-retentive aggregates or even aggregates consisting of some semi-conducting gel particles and some conducting particles should find use as MEMS (MicroElectro-Mechanical System) and NEMS (NanoElectroMechanical System) devices. Occlusion and/or entrapment of magnetic materials such as magnetic polymers or magnetic metal particles could afford a three-dimensional computer memory device. An aggregate containing occluded and/or entrapped metallic materials or metallic ions could be used as a proton exchange membrane for use in a fuel cell. Occlusion of polynucleotide segments in the particles of an aggregate might provide three-dimensional array analytical tools for use in the biotechnology industry. These and may other uses for the shape-retentive aggregates of this invention will become apparent to those skilled in the art based on the disclosures herein. Such uses are within the scope of this invention.

EXAMPLES

Example 1

Hydrogel Particle Preparation using Tween 80 Surfactant

A stock solution of Tween 80 in Milli-Q $H_2O$ was prepared by dissolving 27 g of Tween (80) with 100 g of Milli-Q $H_2O$. A stock solution of potassium persulfate was prepared by dissolving 2 g in 30 mL of Milli-Q $H_2O$. A 1 L media bottle was equipped with a stir bar and charged with 1.74 g HEMA containing 3.6 mg ethylene glycol dimethacrylate, 1.07 g of the Tween 80 stock solution, 571 mL of $N_2$ purged Milli-Q $H_2O$, and 0.952 mL of the potassium persulfate stock solution. The solution was stirred until all of the solids dissolved. The bottle was covered with foil and immersed in a 65° C. bath for 16 hours. The resulting suspension of hydrogel particles had a milky-white to opaque blue opalescence and the particles were found to have an average diameter of 466 nm by dynamic light scattering. The suspension was concentrated and purified by tangential flow filtration and was found to be stable against flocculation at a wet weight concentration approaching 70 mg/mL.

Example 2

Hydrogel Particle Preparation using Dioctyl Sodium Succinate Surfactant

A 500 mL media bottle equipped with a stir bar was charged with 4.25 g HEMA monomer containing 8.8 mg ethylene glycol dimethacrylate, 290.18 mg dioctyl sodium succinate (DSS), 135 mg potassium persulfate, and 500 mL of $N_2$-purged Milli-Q $H_2O$. The bottle was capped and the solution was stirred for 3 hrs at room temperature. The bottle was transferred to a 50° C. water bath and incubated for 12 hrs. The resulting suspension of hydrogel particles had an opalescent blue color. The particles were analyzed by dynamic light scattering and found to have an average diameter of 241 nm. The suspension of particles contained 25 mg of hydrated polymer per mL of solution. The suspension was concentrated and purified using tangential flow filtration and was found to be stable against flocculation at a wet weight concentration approaching 150 mg/mL.

Example 3

Hydrogel Particle Preparation Using Sodium Dodecyl Sulfate Surfactant

A 100 mL media bottle equipped with a stir bar was charged with 4.25 g HEMA monomer containing 8.8 mg ethylene glycol dimethacrylate, 267.91 mg sodium dodecyl sulfate (SDS), 135 mg potassium persulfate, and 500 mL of $N_2$-purged Milli-Q $H_2O$. The bottle was capped and the solution was stirred for 3 hrs at room temperature. The bottle was transferred to a 50° C. water bath and incubated for 12 hrs. The resulting suspension of hydrogel particles had an opalescent blue color. The particles were analyzed by dynamic light scattering and found to have an average diameter of 110 nm. The suspension of particles contained 78 mg of hydrated polymer per mL of solution. The suspension was concentrated and purified using tangential flow filtration and was found to be stable against flocculation at a wet weight concentration approaching 200 mg/mL.

Example 4

Variation in Particle Size with Changes in Monomer Concentration

Changes in the concentration of reagents in solution affect particle size and polydispersity. For particles synthesized according to the procedure in Example 2, particle size and polydispersity was varied by changing the solution volume during polymerization as shown in Table 1:

TABLE 1

| HEMA Mass (g) | DSS Mass (g) | Solution Volume (mL) | Particle Size (nm) | Polydispersity (PDI) |
| --- | --- | --- | --- | --- |
| 4.25 | 0.29 | 100 | 204.1 | 0.185 |
| 4.25 | 0.29 | 250 | 108.6 | 0.154 |
| 4.25 | 0.29 | 500 | 96.4 | 0.030 |
| 4.25 | 0.29 | 1000 | 68.3 | 0.005 |

The above trends show that for a given ratio of HEMA monomer to DSS surfactant during particle synthesis, the particle size and polydispersity both decrease as the solution volume is increased.

Example 5

Exchange of Surfactant and Concentration

A suspension of discrete particles with an average diameter of 110 nm containing a wet weight of 33 mg/mL and a SDS concentration of 0.535 mg/ml was subjected to tangential flow filtration using a Millipore Pellicon® Biomax tangential flow filtration membrane with a 300,000 Daltons cutoff. The filtration was performed at constant volume using a 5% (w/v) Tween 80 solution in Milli-Q $H_2O$ as the make-up. A total of 6×500 mL permeate volumes were collected during the filtration to exchange the SDS surfactant for the Tween 80. The suspension of particles had an average diameter of 318 nm after surfactant exchange, and over a 6 month period showed minimum evidence of sedimentation and aggregation. Particles were concentrated using tangential flow filtration by removing a specific volume of permeate while retaining the particles.

Example 6

Determination of Maximum Concentration of Particles Affording Stable Dispersions as a Function of Particle Size Two series of particles were formed: 1) SDS stabilized particles formed according to Example 3 with 100, 265, and 500 nm diameters respectively, and 2) DSS stabilized particles formed according to Example 2 with 125, 300, 475, and 550 nm diameters respectively. The starting hydrated polymer mass of each sample was determined by weighing a sample after centrifugation. 6 mL of each dispersion was placed into 15 mL graduated centrifuge tubes. Using an analytical evaporator, a stream of Argon gas was passed over the surface of the dispersions in each centrifuge tube while temperature was maintained at 37° C. using a water bath. The samples were inspected for the onset of aggregation of the dispersed particles as their concentrations increased. The change in volume of the sample at the onset of aggregation was recorded and a new concentration was calculated. The effect of particle size on the concentration in which each dispersion began to aggregate for particles of different sizes using SDS and DSS surfactants is graphically represented in FIG. 1.

Example 7

The Effect of Injection Rate, Needle Gauge and Particle Concentration on Aggregate Formation Portions of a stock dispersion of gel particles, synthesized according to Examples 1-3 and concentrated according to Example 3 to a wet weight concentration of 109 mg/mL, were loaded into 20 separate 3 mL disposable syringes. An even number of syringes was equipped with 27, 26, 23 and 18 gauge needles. One milliliter from each syringe was injected into 10 mL of phosphate buffered saline. Flow rates from 0.1 mL/min to 2 mL/min were controlled by a Harvard Apparatus (Model #4400) syringe pump. Qualitative observations were made after each injection and the resulting aggregates were classified into four types as shown in Table 2. Several dilutions of the stock dispersion above were prepared with reduced concentrations and studied using the same procedure.

TABLE 2

| Needle Gauge | Flow Rate (mL/min) | | | | |
|---|---|---|---|---|---|
| | 0.1 | 0.25 | 0.5 | 1 | 2 |
| Dispersion Concentration: 109 mg/mL | | | | | |
| 27 | a | a | a | b | c |
| 26 | a | a | a | b | b |
| 23 | a | a | a | a | a |
| 18 | a | a | a | a | a |
| Dispersion Concentration: 76 mg/mL | | | | | |
| 27 | a | c | c | c | d |
| 26 | a | b | b | c | d |
| 23 | a | a | b | b | c |
| 18 | a | a | a | a | b |
| Dispersion Concentration: 55 mg/mL | | | | | |
| 27 | b | c | c | c | d |
| 26 | a | b | c | c | d |

TABLE 2-continued

| Needle Gauge | Flow Rate (mL/min) | | | | |
|---|---|---|---|---|---|
| | 0.1 | 0.25 | 0.5 | 1 | 2 |
| 23 | a | a | b | c | d |
| 18 | a | a | a | a | b |
| Dispersion Concentration 33 mg/mL | | | | | |
| 27 | d | d | d | d | d |
| 26 | d | d | d | d | d |
| 23 | d | d | d | d | d |
| 18 | d | d | d | d | d | a Immediate formation of dense, pliable material
b Immediate formation of dense, pliable material with moderate associated flocculation.
c Flocculation with subsequent formation of dense, pliable material in <15 min.
d Flocculation with subsequent formation of dense, pliable material in >15 min.

Example 8

Aggregation Types Using Larger Particles

Bulk, dry PHEMA was ground and sieved into three different particle size ranges: less than 45 μm, larger than 45 μm but smaller than 75 μm and larger than 75 μm but smaller than 150 μm. Suspensions for each particle type were prepared using MilliQ water containing 0.015 wt % DSS as the suspending medium. Each suspension was prepared so that the wet weight of particles was 150 mg/mL. One milliliter of each suspension was injected into 15 mL of PBS using 3 mL disposable syringes equipped with 18 gauge needles. Flow rate of each injection was approximately 1 mL/min. Qualitative observations were made of each injection, and the aggregates were classified into different types as shown in Table 3.

TABLE 3

| Particle Size Range | Aggregation Type |
|---|---|
| Less than 45 μm | a |
| Between 45 μm and 75 μm | b |
| Between 75 μm and 150 μm | d | a Immediate formation of dense, pliable material
b Immediate formation of dense, pliable material with moderate associated flocculation.
c Flocculation with subsequent formation of dense, pliable material in <15 min.
d Flocculation with subsequent formation of dense, pliable material in >15 min.

Example 9

Formation of Shape-Retentive Aggregate In Vivo

Figure 2:
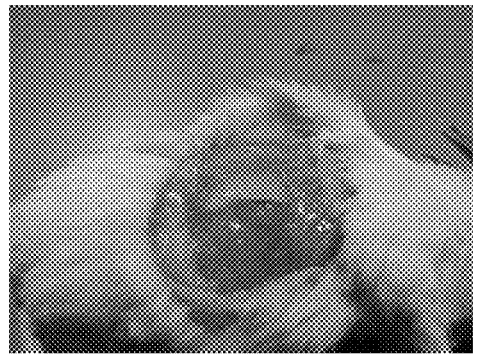
FIG. 2 is a photograph of a pHEMA particle aggregate formed in vivo using the method of this invention.

Hydrogel particles were suspended in a solution of isotonic glucose. The suspension contained 110 mg/mL of hydrated polymer. One suspension (A) contained pure PHEMA particles. The second suspension (B) contained a mixture of 50:50 pHEMA:(95:5 PHEMA:MAA) by weight. Injections that contained 100 mg of hydrated polymer were made subcutaneously above the dorsal fascia of mice. Animals were sacrificed at 24 hrs and 7 days. The implants were excised and observed. Both implants were present beneath the site of injection 1 and 7 days post implantation. Both implants formed circular disks of elastic hydrogel material and showed little evidence of local irritation. The implant weights were slightly higher than the centrifuged hydrated weight of polymer; this higher weight likely due to the infiltration of tissue into the body of the aggregate. The implant containing a mixture of pHEMA and 95:5 pHEMA:MAA particles was more opaque than the pure pHEMA implant and showed extensive tissue infiltration after 7 days. FIG. 2 shows an aggregate formed in this manner in vivo. Implants formed in vivo using pHEMA particles dispersed in solutions of Tween 80 surfactant and dioctyl sodium sulfate (DSS) surfactant showed no evidence of irritation or erosion over 14 days.

Example 10

Loss of Absorbed Water Weight During Aggregation for Different Particle Sizes

Figure 3:
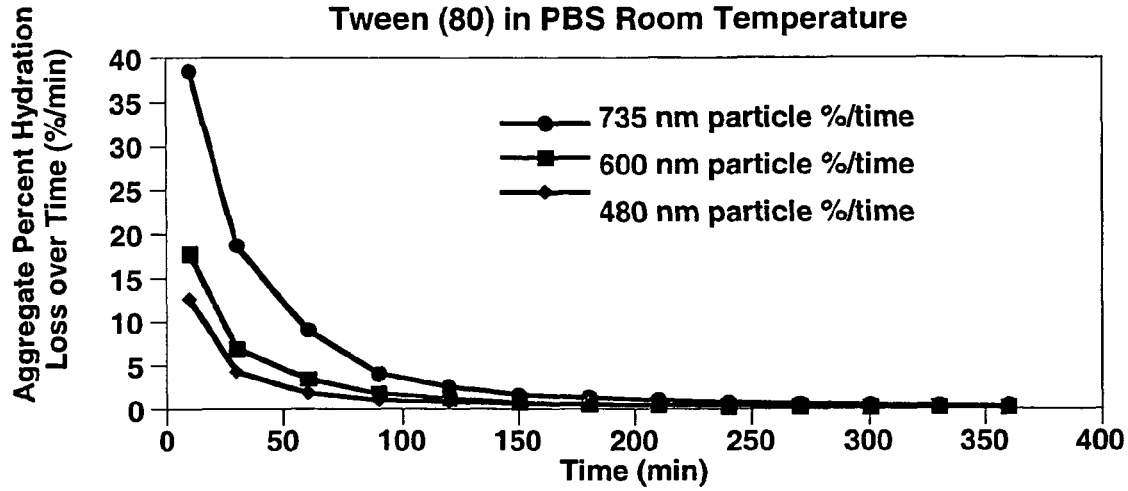
FIGS. 3-9 show plots of first derivatives calculated from the slope at various times of a curve generated by measuring water loss at incremental times by gel particle aggregates as they proceed from initial coalescence to their final shape-retentive form. The first derivative provides the rate of water loss per unit time at the points of measurement.

Injection of particles into a solution in which the particles have a lower swelling rate, such as a solution of higher ionic strength, forms a hydrogel particle aggregate. The rate of aggregate formation can be quantified by determining the loss of water mass for the aggregate over time after injection. For a given surfactant at a given concentration, pHEMA particles dispersed in water at a given concentration show different rates of aggregate formation when injected into phosphate buffered saline at physiological pH and ionic strength at room temperature. In a typical experiment, 2 mL of a dispersion of hydrogel particles 680 nm in diameter in an aqueous solution of 0.5 wt. % Tween 80 surfactant with a centrifuged wet polymer weight of 37 mg/mL determined by centrifugation was injected into 100 mL of PBS. The resulting aggregate was allowed to form undisturbed for 10-15 minutes and was subsequently filtered through a screen, weighed, and returned to the PBS solution. The mass was reported as a percentage of the centrifuged wet polymer mass that shows the amount of water both within and between the particles comprising the aggregate as it collapses. FIG. 3 shows a plot of the rate of aggregation over time from the initial injection to the point at which the aggregate has reached a steady state mass. The plot shows that larger particles exhibit a more rapid initial change in the rate of aggregation, however, both sizes reach an equilibrium hydration content between 150 and 200 minutes. Larger particles with the same surface charge as smaller particles have a different Gaussian charge to surface area ratio, which imparts less stability even though the overall charge is identical. Because the particles are slightly less stable even with identical zeta potential, they reach the steady state aggregate state faster than corresponding smaller particles. This shows that variation in the particle size with uniform surfactant and particle concentration results in different rates of aggregate formation.

Example 11

Loss of Absorbed Water Weight During Aggregation at Different Temperatures

Figure 4:
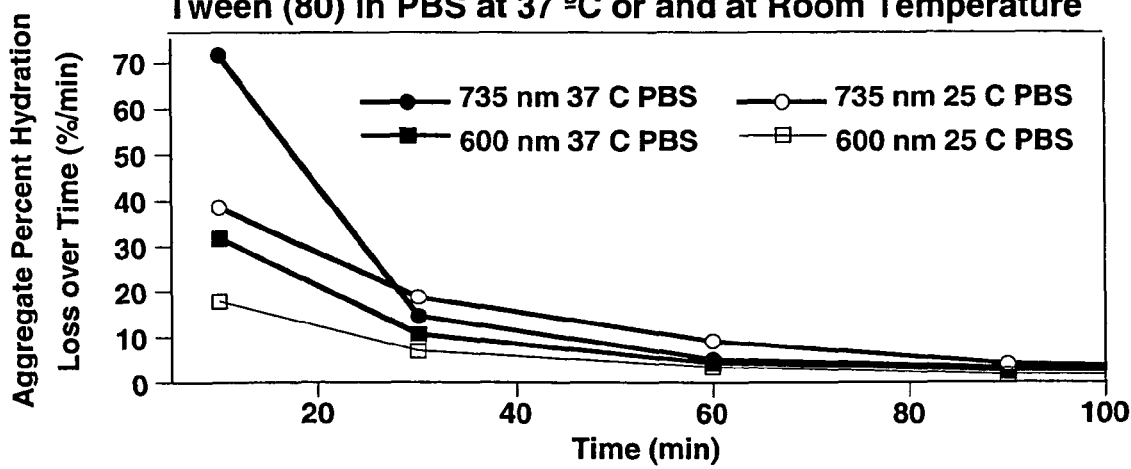

Temperature has an effect on the rate of aggregate formation for a given suspension. In a typical experiment, 2 mL of a dispersion of hydrogel particles 735 nm in diameter in an aqueous solution of 0.5 wt. % Tween 80 surfactant with a wet polymer weight of 37 mg/mL as determined by centrifugation was injected into 100 mL of PBS at 37° C. The resulting aggregate was allowed to form undisturbed for 10-15 minutes and was subsequently filtered through a screen, weighed, and returned to the PBS solution. The mass was reported as a percentage of the centrifuged wet polymer mass that shows the amount of water both within and between the particles comprising the aggregate as it collapses. A comparison of the rates of aggregate mass loss over time for particle dispersions injected into PBS at 25° and 37° C. shows that the rate of aggregate formation is faster at a higher temperature. FIG. 4 shows the rate of aggregation over time from the initial injection to the point at which the aggregate has reached an equilibrium weight in PBS at two different temperatures. The data indicates that for a given particle size, the rate of aggregate formation indicated by the weight loss over time is faster initially at higher temperatures.

Example 12

Loss of Absorbed Water Weight During Aggregation in Serum

Figure 5:
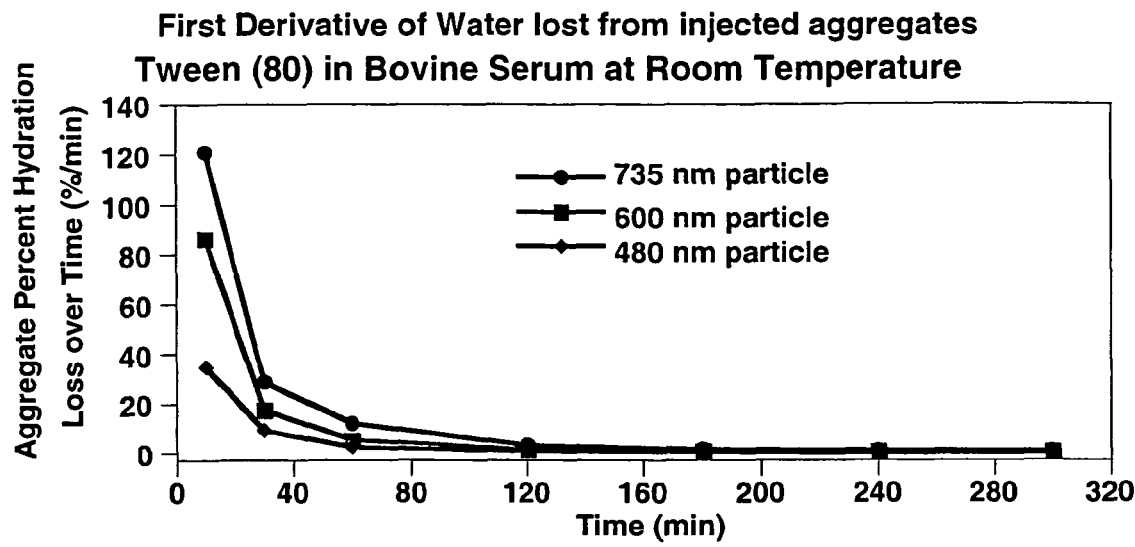

Particle aggregates were formed in bovine serum. In a typical experiment 2 mL of a dispersion of hydrogel particles in an aqueous solution of 0.5 wt. % Tween 80 surfactant with a wet polymer weight of 37 mg/mL as determined by centrifugation was injected into 100 mL of bovine serum at 25° C. The resulting aggregate was allowed to form undisturbed for 10-15 minutes and was subsequently filtered through a screen, weighed, and returned to the PBS solution. The mass was reported as a percentage of the centrifuged wet polymer mass which shows the amount of liquid both within and between the particles comprising the aggregate as it collapses. FIG. 5 shows the rate of aggregation over time from after the initial injection to the point at which the aggregate has reached a steady state mass in serum. Again, larger particles with the same surface charge as smaller particles have a different Gaussian charge to surface area which imparts less stability though the overall charge is identical. Because the particles are slightly less stable even with identical zeta potential, they reach the steady state aggregate state faster than corresponding smaller particles.

Example 13

Loss of Absorbed Water Weight During Aggregation in Hypertonic Saline

Figure 6:
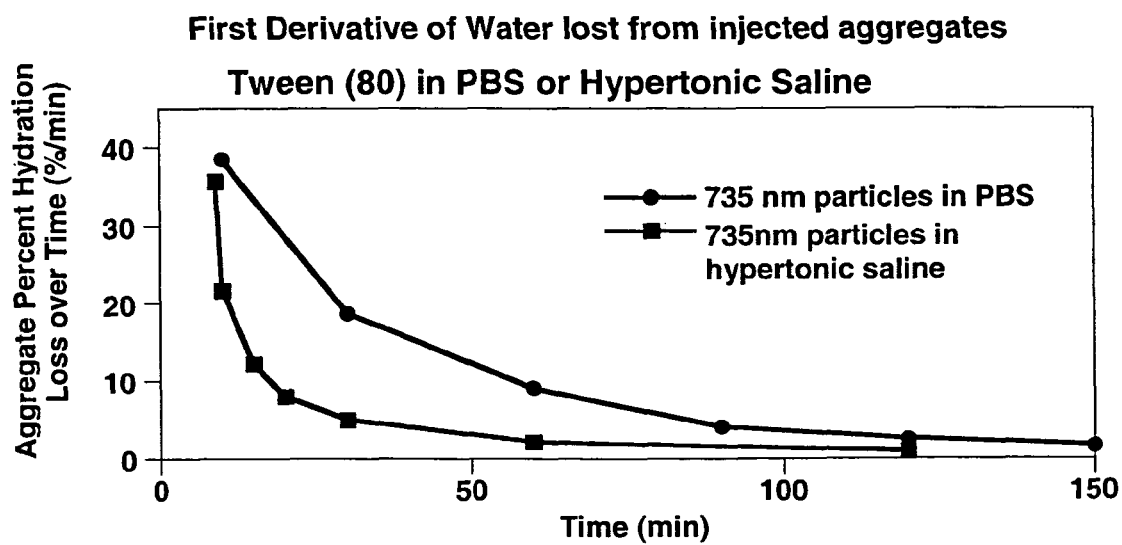

Particle aggregates were formed in a solution of hypertonic saline. In a typical experiment, 2 mL of a dispersion of hydrogel particles 680 nm in diameter in an aqueous solution of 0.5 wt. % Tween 80 surfactant with a wet polymer weight of 37 mg/mL as determined by centrifugation was injected into 100 mL of saturated sodium chloride solution. The resulting aggregate formed immediately at the surface of the solution, and returned to the PBS solution. The mass was reported as a percentage of the centrifuged wet polymer mass that shows the amount of water both within and between the particles comprising the aggregate as it collapses. FIG. 6 shows a plot of the rate of aggregation over time from the initial injection to the point at which the aggregate has reached a steady state mass. The plot shows that larger particles show a more rapid initial change in the rate of aggregation, however, both aggregates composed of various particle sizes reached a steady state between 150 and 200 minutes. This shows that changing the ionic strength of a solution has an effect on the rate of aggregation and that the change in zeta potential can be shown in solutions of varying ionic strength.

Example 14

Figure 7:
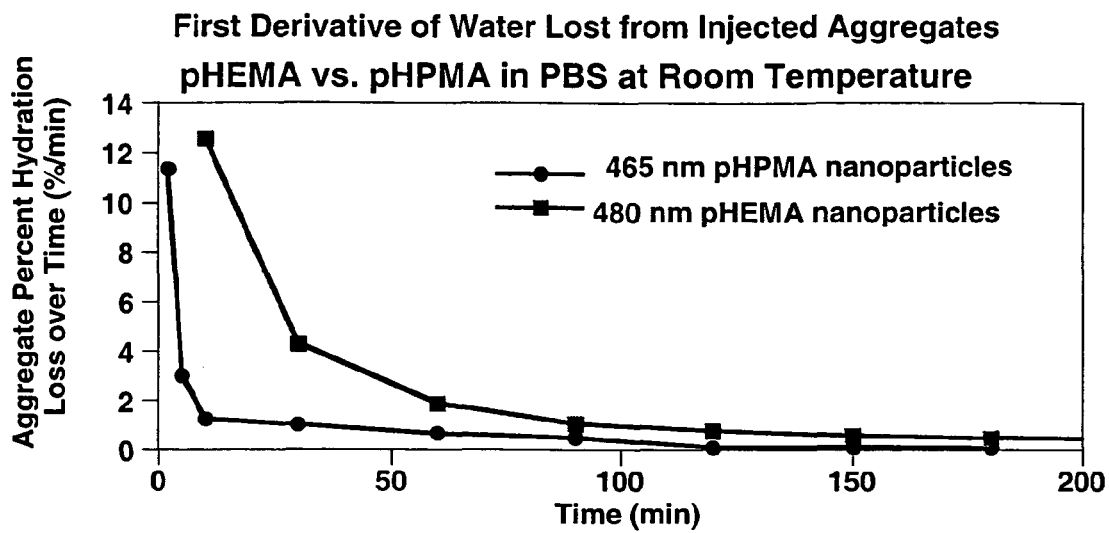

Loss of Absorbed Water Weight During Aggregation of Hydrogel Particles of Different Chemical Composition The polymer composition of hydrogel particles has an effect on the rate of aggregate formation in a given solution. In a typical experiment, 2 mL of a dispersion of hydrogel particles with a wet polymer weight of 37 mg/mL as determined by centrifugation which had a composition of either poly(2-hydroxyethylmethacrylate) or poly(2-hydroxypropyl-methacrylate) with average diameters of 480 or 465 nm respectively was injected into 100 mL of phosphate buffered saline at room temperature. The resulting aggregate was allowed to form undisturbed for 2 minutes for the p(HPMA) particles or 10-15 minutes for the p(HEMA) particles and was subsequently filtered through a screen, weighed, and returned to the PBS solution. The mass was reported as a percentage of the centrifuged wet polymer weight that shows the amount of water both within and between the particles comprising the aggregate as it collapses. A comparison of the rates of aggregate mass loss over time for particle dispersions injected into PBS at 25° C. shows that the rate of aggregate formation is faster for pHPMA particles of a given size. This means that even with identical surfactant and surface charge, putting particles of different chemical composition into a different ionic strength will result in different rates of aggregation which again is an indirect determination of the stability of the zeta potential. FIG. 7 shows the rate of aggregation over time from the initial injection to the point at which the aggregate has reached a steady state mass in PBS at two different temperatures. The data indicates that for a given particle size, the rate of aggregate formation indicated by the water weight loss over time is faster initially for PHPMA than for PHEMA.

Example 15

Loss of Absorbed Water Weight During Aggregation of Hydrogel Particles with Different Surfactants The surfactant used to stabilize hydrogel particles has an effect on the rate of aggregate formation in a given solution. In a typical experiment, 2 mL of a dispersion of pHEMA particles with a wet polymer weight of 37 mg/mL as determined by centrifugation with average diameters of 175 nm and stabilized with either 0.5 w/v % of SDS or DSS surfactants was injected into 25 mL of PBS at room temperature or 37° C. The resulting aggregate was allowed to form undisturbed for 2 minutes for the 10-15 minutes and was subsequently filtered through a screen, weighed, and returned to the PBS solution. The mass was reported as a percentage of the centrifuged wet polymer weight that shows the amount of water both within and between the particles comprising the aggregate as it collapses. A comparison of the rates of aggregate mass loss over time for particle dispersions injected into PBS at 25° C. shows that the rate of aggregate formation is faster for DSS-stabilized particles. FIG. 8 shows the rate of aggregation over time from after the initial injection to the point at which the aggregate has reached a steady state mass in PBS at two different temperatures. The data indicates that for a given particle size, the rate of aggregate formation indicated by the water weight loss over time is faster initially for DSS stabilized particles than for those stabilized by SDS.

Example 16

Formation of Particle Aggregates that Undergo Erosion or Partial Erosion

Injection of particles composed of copolymers of HEMA and methacrylic acid (MAA) in a solution of physiological pH and ionic strength results in either the formation of an aggregate that slowly erodes or does not form at all. In a typical experiment, 2 mL of a suspension of 95:5 pHEMA:MAA particles 155 nm in diameter containing 110 mg/mL of hydrated polymer was injected into phosphate buffered saline. The aggregate showed an initial loss of water weight similar to aggregates in Example 12. Following the initial aggregation, the aggregate gradually erodes as the methacrylic acid part of the particle copolymer is ionized. Table 4 shows the time for erosion after the initial aggregation for particles with different amounts of MM in the HEMA:MAA copolymer.

TABLE 4

| HEMA:MAA Ratio | Time to erosion after initial aggregation |
|---|---|
| 100:0 | Indefinite |
| 99:1 | Indefinite |
| 98:2 | Over one month |
| 97:3 | 21 days |
| 95:5 | 10-12 days |
| 90:10 | 2-3 days |
| 80:20 | No aggregate formed |
| 70:30 | No aggregate formed |

Example 17

Particle Clustering

At wet weight concentrations greater than 50 mg/mL, discrete pHEMA particles have a propensity to agglomerate into larger but still dispersible clusters. The clustering process has been documented by sampling aliquots of the dispersion during TFF purification and monitoring the particle size and polydispersity while concentrating a 2 L dispersion of 53 nm (PDI 0.098) pHEMA particles having a wet weight concentration of 36.2 mg/mL down to a volume of 235 mL and a final wet weight concentration of 424 mg/mL. The results are presented in Table 5:

TABLE 5

| Particle Conc. (mg/mL) | Range In Particle Size (nm) | Ave. Peak or Peak Sizes (nm) | PDI |
|---|---|---|---|
| 36.2 | 24-122 | 53 | 0.098 |
| 39.2 | 14-122 | 53 | 0.112 |
| 42.5 | 33-106 | 54 | 0.085 |
| 45.2 | 28-122 | 54 | 0.106 |
| 48.2 | 18-164 | 55 | 0.110 |
| 51.7 | 33-142 | 57 | 0.053 |
| 55.6 | 24-122 | 57 | 0.078 |
| 60.3 | 18-164 | 57 | 0.103 |
| 65.8 | 28-142 | 57 | 0.098 |
| 72.3 | 28-122 | 59 | 0.092 |
| 80.4 | 16-122 | 60 | 0.098 |
| 90.4 | 21-190 | 61 | 0.060 |
| 103 | 38-122 | 64 | 0.066 |
| 121 | 38-190 | 67 | 0.103 |
| 145 | 28-164 | 80 | 0.098 |
| 181 | 33-190 | 100 | 0.104 |
| 241 | 33-220 | 100 | 0.102 |
| <424 | 28-220 | 99 | 0.111 |
| 424 | 91-955 | 154, 563 | 0.307 |

Figure 9:
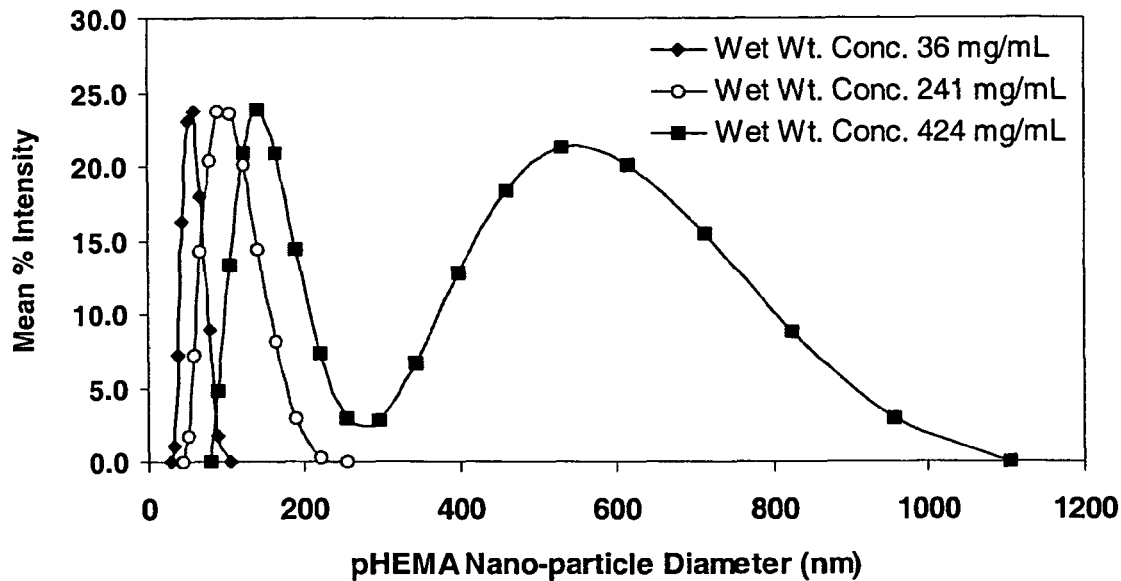

The above trend demonstrates that the average PHEMA particle peak size increases after the polymer wet weight concentration exceeded 50 mg/mL. Also observed was an increase in the viscosity of the dispersion (approaching that of a true sol without aggregating to a solid mass). Changes in the peak shape or distribution of particle sizes about the average peak value as well as changes in the peak modality and base line widths of the distributions about the peak average were also observed. The change from discrete pHEMA particles to the pHEMA cluster distributions is shown FIG. 9.

Example 18

Change the Zeta Potential by Removing Surfactant Induces Particle Aggregation

A particle dispersion was prepared as described in Example 3 to give particles 60 nm in diameter. 100 mL of the dispersion was subjected to tangential flow filtration to remove SDS surfactant. The filtration was performed at constant volume using Milli-Q $H_2O$ as the make-up. Zeta potential determination and size analysis were performed on the sample after 100 mL, 150 mL and 200 mL of permeate were collected. As surfactant was removed, the magnitude of zeta potential of the particles decreased causing clustering of the particles. This is shown in Table 6. After 250 mL of permeate was collected, aggregation of the particles occurred within the sample.

TABLE 6

| Zeta Potential (mV) | Particle Size (nm) |
|---|---|
| −28.94 | 60 |
| −24.32 | 65.58 |
| −24.21 | 70.33 |
| −20.81 | 138.2 |

Example 19

Effect of Changing Ionic Strength (Salt Concentration) of the Dispersing Medium on the Size of SDS-Stabilized PHEMA Particles pHEMA particles with diameters of about 92 nm were prepared using the surfactant SDS as described in Example 1. The wet weight concentration of the dispersion was approximately 30 mg/mL. Five drops (105 uL) of pHEMA particle dispersions were placed in 3 mL of MilliQ water and in 3 ml of 1, 2, 3, 4, 5, 6, 7 and 10 mM NaCl salt solutions. The sizes and zeta potentials of the suspended particles were determined using a Malvern Instrument, Nano ZS Zetasizer. The results indicated that as the ionic strength of the suspending medium increases, the zeta potential of the particles decreases with a concomitant decrease in particle size. When the salt concentration is below 2 mM NaCl, the particles are still relatively stable as the absolute surface charge is still significant and the particles tend to repel each other. However, as the ionic strength increases, the absolute surface charge begins to decrease and the particles tend to form clusters to reduce the surface area exposed to the suspending liquid and will continue to cluster until they flocculate into larger agglomerates of particles and finally settle into a solid aggregate.

Example 20

Effect of Changing Ionic Strength of the Dispersing Medium on the Size of Individual SDS-Stablized pHEMA Particles PHEMA particles (with diameters of ca. 60, 92, 250 nm) were prepared using the surfactant SDS as previously described. The wet weight concentration of each dispersion was about 30 mg/mL. Five drops (105 uL) of 92 and 250 nm, pHEMA particle dispersions were placed in each of 3 mL of 2 mM NaCl solutions. The size and zeta potential of the suspended particles were determined. After these measurements, the media were diluted with 1 volume equivalent of MilliQ water to decrease the salt content by 50% in such a manner that a serial dilution was carried to give readings for zeta potential and size in 2, 1, 0.5, 0.25, 0.125 mM NaCl solutions. The results are shown in Table 7 below.

TABLE 7

Effect of ionic strength on particle size

| NaCl Conc (mM) | Particle Size Diameter (nm) | Zeta Potential (mV) |
|---|---|---|
| 2.0 | 250.94 | −26.468 |
| 1.0 | 251.20 | −36.153 |
| 0.5 | 254.40 | −42.177 |
| 0.3 | 255.43 | −44.588 |
| 0.1 | 262.07 | −47.173 |
| 2.0 | 96.38 | −21.840 |
| 1.0 | 98.37 | −25.993 |
| 0.5 | 98.74 | −29.030 |
| 0.3 | 99.59 | −29.667 |
| 0.1 | 99.68 | −30.553 |
| 1.0 | 59.54 | −22.913 |
| 0.5 | 59.94 | −25.287 |
| 0.3 | 60.56 | −29.253 |
| 0.1 | 60.66 | −32.013 |

Figure 10:
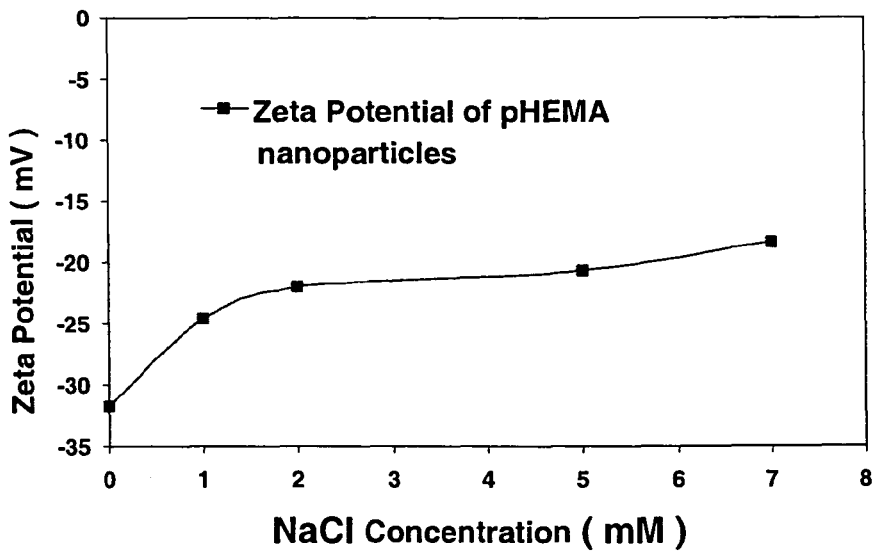
FIG. 10 is a plot showing the effect of ionic strength on the zeta potential of SDS-stabilized pHEMA particles.

Table 7 shows that, for each PHEMA particle size (ca. 250, 100, and 60 nm, respectively), as the salt content is decreased (i.e., the ionic strength of the suspending medium is decreased), the corresponding particle diameters increased. As the ionic strength of the suspending medium is decreased, the absolute value of the zeta potential on the particles increases. The results are also shown in FIG. 10.

Example 21

Particle Size Change with Dilution of Dispersion Medium Using a Miscible Co-Dispersant Discrete pHEMA particles in a stable aqueous dispersion can undergo changes in size and can aggregate when the aqueous solution is diluted with a non-aqueous, miscible co-dispersion medium. In a typical example, a dispersion of pHEMA particles with a wet weight concentration of 63 mg/mL and a diameter of 68 nm is diluted using acetone. The ratio of Milli-Q to acetone in the final solution was varied from 100% to 5%. The particle size initially decreased with the addition of the co-dispersion medium but later increased as aggregation occurred, and multiple particle size peaks formed. The results are shown in Table 8.

TABLE 8

| Dispersion medium Ratio Milli-Q/Acetone (v/v) | Average Particle Diameter(s) (nm) |
|---|---|
| 100/0 | 68 |
| 95:5 | 59 |
| 90:10 | 52 |
| 80:20 | 120 |
| 70:30 | 68, 160 |
| 50:50 | 54, 230, 439 |
| 30:70 | 48, 225, 430 |

TABLE 8-continued

| Dispersion medium Ratio Milli-Q/Acetone (v/v) | Average Particle Diameter(s) (nm) |
|---|---|
| 20:80 | 480, aggregate |
| 90:10 | Aggregate |
| 95:5 | Aggregate |

A similar experiment was performed on the same series of particles using ethanol as a co-dispersant. Ethanol is a solvent which provides some solubility for PHEMA. The results of the co-dispersion experiment are shown in Table 9.

TABLE 9

| Dispersion medium Ratio Milli-Q/Ethanol (v/v) | Average Particle Diameter (nm) |
|---|---|
| 100/0 | 68 |
| 95:5 | 72 |
| 90:10 | 76 |
| 80:20 | 78 |
| 70:30 | 74 |
| 50:50 | 78 |
| 30:70 | 74 |
| 20:80 | 76 |
| 90:10 | 74 |
| 95:5 | 78 |

The above results demonstrate that the nature of a co-dispersion medium can affect the stability of a particle dispersion and the onset of aggregation, again by changing the magnitude of the zeta potential on the particles.

Example 22

Formation of a Gelatinous Aggregate by Introduction of a Hydrophobic Solvent into a Particle Dispersion A stable aqueous dispersion of discrete particles exhibits unique properties when a non-miscible solvent is mixed with the dispersion medium. In a typical example, a dispersion of PHEMA particles with a wet weight concentration of 63 mg/mL and a diameter of 68 nm is combined with an equivalent volume of hexane. The clear hexane layer showed no evidence of mixing with the opalescent particle dispersion over 5 days at room temperature. Vigorous mixing of the solution resulted in the formation of a gelatinous mass suspended above the aqueous particle dispersion. Separation of the aqueous solution from the hydrophobic layer from the aqueous particle dispersion with subsequent vacuum evaporation of the hexane resulted in the formation of a stable particle aggregate.

Example 23

Dilution of PHEMA Particle Dispersion

Discrete PHEMA particles in a stable aqueous dispersion undergo very limited changes in size and zeta potential when diluted with the dispersion medium, and do not aggregate. In a typical example, a dispersion of PHEMA particles with a wet weight concentration of 63 mg/mL and a diameter of 68 nm was diluted with Milli-Q H$_2$O in a serial dilution. The effects of the dilution on particle size and zeta potential are shown in Table 10.

TABLE 10

| Particle Concentration (mg/mL) | Average Particle Diameter (nm) | Zeta Potential (mV) |
|---|---|---|
| 63 | 68 | −28 |
| 31.5 | 69 | −30 |
| 15.8 | 73 | −31 |
| 7.9 | 71 | −30 |
| 3.9 | 74 | −29 |
| 2.0 | 75 | Not detectable |

At very low particle concentrations (<2 mg/mL), the zeta potential of the particles was below the limits of detection for the instrument.

Example 24

Entrapment and Release of a Small Molecule from Particle Aggregates

Figure 12:
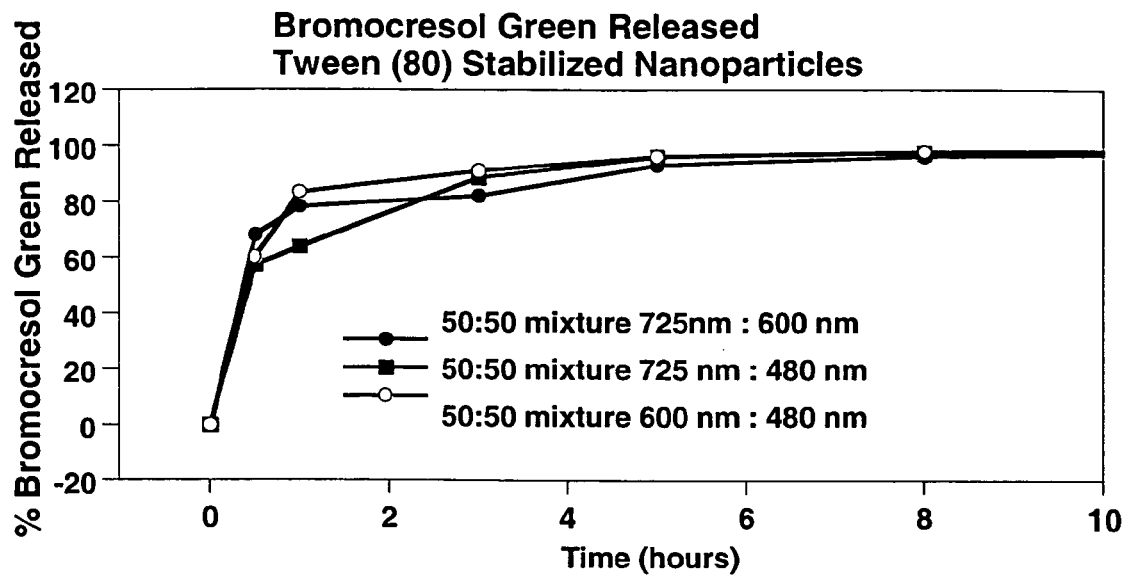
FIG. 12 is a plot showing the release of bromocresol green dye from aggregates composed of broad polydispersivity pHEMA particles injected into PBS at room temperature.
Figure 13:
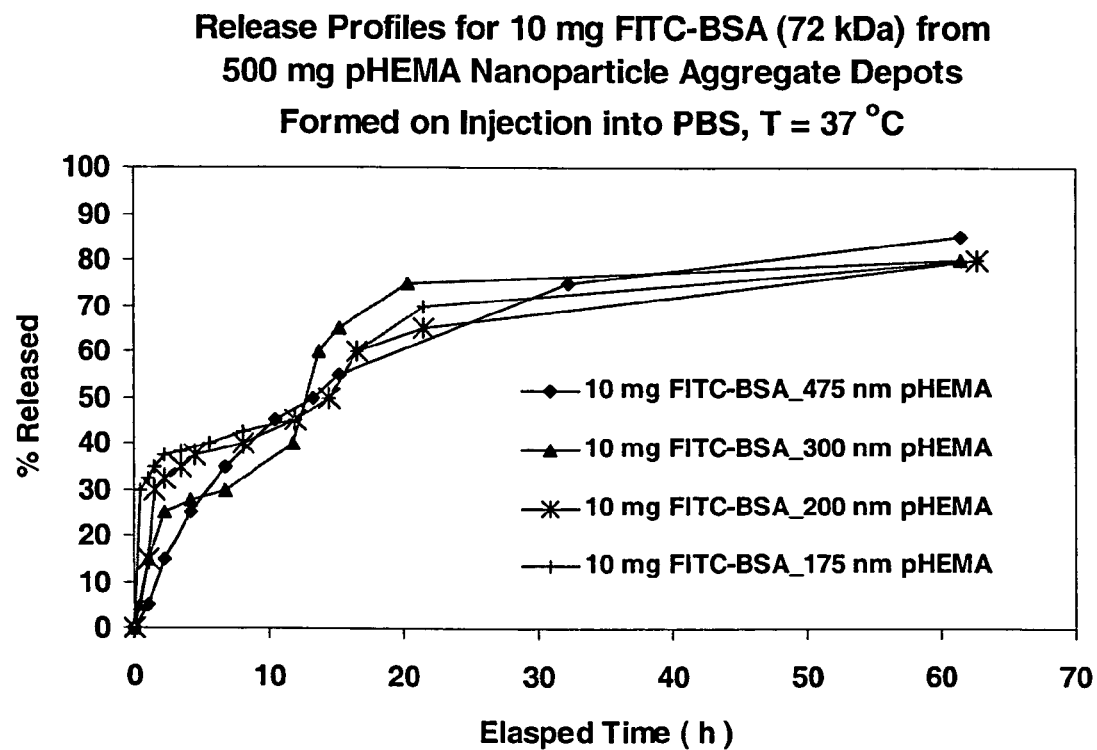
FIG. 13 is a plot showing the release of 10 mg FITC-BSA (72 kDA) from a series of 500 mg aggregates made from pHEMA particles of various diameters injected into PBS at room temperature.

Injection of a dispersion of particles with a small molecule dissolved in the suspension medium forms an aggregate that traps some of the small molecule. In a typical experiment, 1 mg of bromocresol green dye was dissolved into 2 mL of a suspension of Tween 80 stabilized pHEMA particles (725 nm in diameter) with a hydrated polymer mass of 36 mg/mL. The dispersed particles and dye were injected into a solution of phosphate buffered saline. After 10 minutes of aggregation, the solution was shaken at 10 cycles per second to insure adequate mixing. 2 mL samples of supernatant were taken and characterized by UV-Visible absorption spectroscopy. FIG. 11 shows the percent of bromocresol green released in the solution over time from aggregates formed of discrete particles. FIG. 12 shows the percent of bromocresol green released in the solution over time from 50:50 mixtures by mass of two different particle sizes. In both cases, most of the small molecule is released within the first 3-5 hours, however, the burst effect is smaller in the mixed aggregate system.

Example 25

Co-Dispersant Acceleration of Aggregate Formation 50 mg of poly(ethylene glycol) (Mw=400 g/mol) as a co-dispersant was added to 1 mL of a 115 mg/mL, 300 nm HEMA particle dispersion. The dispersion was mixed thoroughly and placed into a 1 mL syringe. The dispersion was injected into 15 mL of PBS at a rate of about 4 mL per minute using a 27 gauge needle. The injected material collapsed quickly into an aggregate with very little flocculation.

When 1 mL of a 115 mg/mL, 300 nm HEMA particle dispersion without. added poly(ethylene glycol) added was injected into 15 mL of PBS at a rate of about 4 mL per minute with a 27 gauge needle, flocculation occurred. However, an aggregate formed after about 30 minutes. Both aggregates were allowed to stand in PBS for 24 hours. The aggregate formed from the PEG co-dispersant system appeared denser and mechanically robust that the aggregate formed without the co-dispersant.

Example 26

Loading Efficiency and Release of FITC Labeled BSA and FITC Labeled Dextran from PHEMA Particle Aggregates Composed of Different Particle Sizes and Amounts of Labeled Compound pHEMA particles having diameters of 475, 300, 200 and 175 nm were used to produce pHEMA particle aggregates. The effect on loading and release of two different sized macromolecules; i.e., FITC-BSA (72 kDa) and FITC-Dextran (2000 kDa) was assessed as a function of particle size. Using a Harvard Model 4400 Syringe Pump, a 10 mL syringe, 16 gauge needle an infusion rate of 2 mL/min, 2 sets of 8-500 mg PHEMA particle aggregates standards containing 10, 7, 5, 3, 2,1, 0.5 and 0 mg of FITC-BSA (Standard Set 1) and 20, 15, 10, 6, 4, 2,1 and 0 mg FITC-Dex (Standard Set 2) were prepared. Five milliliters of a 475 nm PHEMA particle dispersion were mixed with a pre-weighed aliquot of the FITC-labeled macromolecule and the dispersion was injected into PBS at room temperature. Upon injection into PBS, the discrete particle dispersions aggregated and entrapped the macromolecule. The supernatant was removed and the FITC label provided a gradient of yellow hues for each of the aggregates containing the two macromolecules at varying concentrations, allowing one to contrast the observed hue exhibited by the standard to that of a sample prepared in an identical manner.

Five-hundred milligram sample aggregates were prepared by injecting a 5 mL aliquot (100 mg/mL) of each of the above particle dispersions containing either 5 or 10 mg of FITC-BSA or 10 or 20 mg of FITC-Dex in PBS at 37.4° C. The loading and release profiles of the macromolecules were determined by comparing the observed hue at a given time to that of the standard set of aggregates. These results are shown in FIGS. 13-26.

Loading for both macromolecules was very efficient (i.e., >95%). At 10 mg FITC-BSA (roughly 2 wt % of the aggregate), a large burst release (nearly 40%) was observed within the first 5 hours particularly in the aggregates composed of the smaller particles. This was not observed to the same extent at lower loading (5 mg FITC-BSA). The aggregates constructed with the two smaller particle sizes (200 and 175 nm) showed a near zero order release for the first twenty hours.

Thus, larger macromolecules diffuse out of the aggregates at slower rates as shown in the release profiles for the two macromolecules. Also, the release profiles from aggregates prepared using increasing amounts of smaller particles show slower release than from aggregates formed from larger particles.

Example 27

Figure 18:
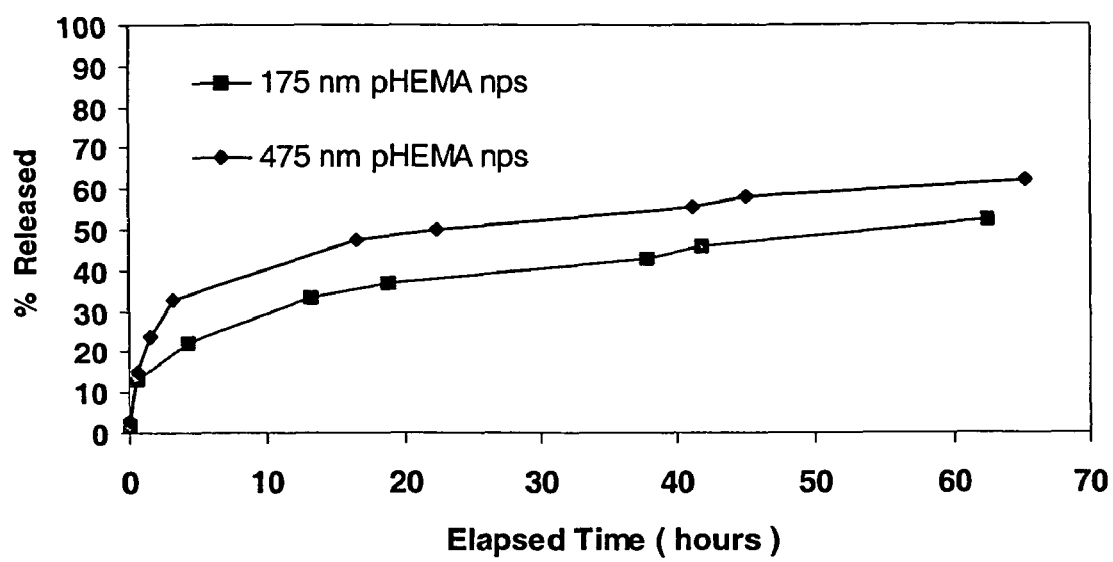
FIG. 18 is a plot showing the release of FITC-Dextran (2000 kDa) from aggregates produced from dispersions of SDS-stabilized particles of various sizes injected in PBS at room temperature.
Figure 19:
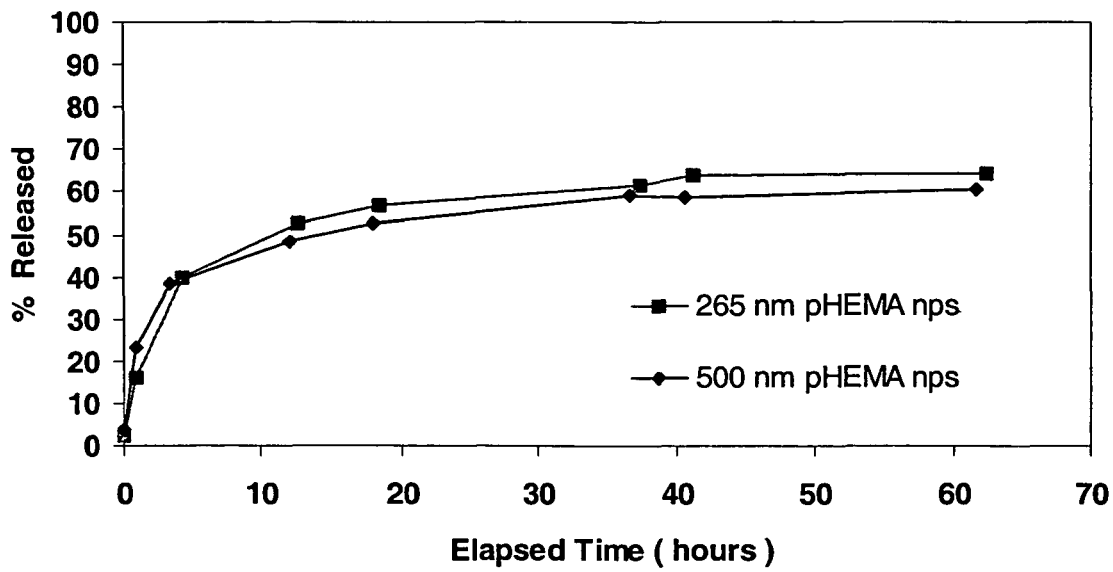
FIG. 19 is a plot showing the release of FITC-BSA (72 kDa) from aggregates produced from dispersions of DSS-stabilized particles of different sizes injected in PBS at room temperature.

Release of Macromolecules from pHEMA Particle Aggregates Composed of 175 and 475 nm Particles Made Using SDS A detailed study was performed to follow the release of macromolecules from pHEMA particle aggregates as a function of macromolecule size. PHEMA particles (with diameters of 475 nm and 175 nm) were prepared using the surfactant SDS as previously described. Using a Harvard Model 4400 Syringe Pump, a 10 mL syringe, 22-gauge needle, an infusion rate of 1 mL/min, 500 mg PHEMA particle aggregates containing either 10 mg FITC-BSA or 10 mg FITC-Dex were prepared. Five milliliters of 100 mg/mL (475 nm or 175 nm) pHEMA particle dispersion were mixed with a pre-weighed aliquot of the FITC-labled macromolecule and the dispersion was injected into PBS at room temperature. The rate of release of the FITC labeled macromolecules was determined using UV-Vis analysis (FITC-BSA $\lambda_{max}$ 486 nm, FITC-Dex $\lambda_{max}$ 492 nm); FITC concentrations were determined relative to standard Beers Law calibration curves for FITC-BSA and FITC-Dex. The results are shown in FIGS. 18 and 19.

FITC-BSA shows a 30% and a 40% burst release from the aggregates composed of 475 and 175 nm pHEMA particles. After the initial burst release, both aggregates composed of the 475 nm and 175 nm particles exhibit a slow release of the macromolecule after approximately 50% of the FITC-BSA has been released.

The larger of the two macromolecules shows a much smaller burst release. It was also found that aggregates composed of smaller particles are more effective at entrapment and prolonged release than those made from larger particles. The burst release from the 175 nm aggregate was <25% after 5 hours, while the aggregate constructed with 475 nm particles showed a burst release of 35% of the loaded FITC-Dex over the same time period. This shows a correlation between particle sizes used in the construction of the aggregate relative to the size of macromolecule that is subsequently released.

Example 28

Figure 20:
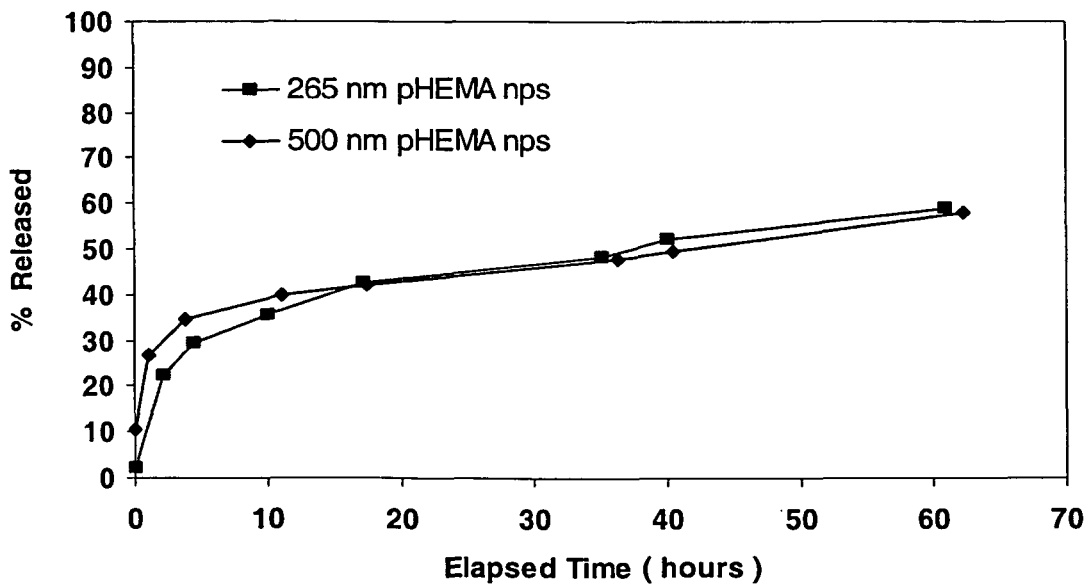
FIG. 20 is a plot showing the release of FITC-Dextran (2000 kDa) from aggregates produced from dispersions of DSS-stabilized particles of different sizes injected in PBS at room temperature.

Release of Macromolecules from PHEMA Particle Aggregates Composed of 265 and 500 nm Particles Made Using DSS pHEMA particles (with diameters of 500 nm and 265 nm) were prepared using the surfactant DSS as previously described. Using a Harvard Model 4400 Syringe Pump, a 10 mL syringe, 22-gauge needle, an infusion rate of 1 mL/min, 500 mg PHEMA particle aggregates containing either 10 mg FITC-BSA or 10 mg FITC-Dex were prepared. Five milliliters of 100 mg/mL (500 nm or 265 nm) PHEMA particle dispersion were mixed with a pre-weighed aliquot of the FITC-labled macromolecule and the dispersion was injected into PBS at room temperature. The rates of release of the FITC labeled macromolecules were determined using UV-Vis analysis and concentrations were determined as above. The results are shown in FIGS. 19 and 20. The larger macromolecule was released at a slower rate and the aggregate produced using 265 nm particles shows a pseudo zero order release with a slightly larger burst than that observed for the aggregate composed of 175 nm particles, previously described. The FITC-BSA shows a burst of nearly 40% from either system within the first 5 hours. This would indicate that this particular macromolecule is very sensitive to the size of the particles used in the aggregate and therefore a much smaller particle diameter may be required.

Example 29

Release of Macromolecules from PHEMA Particle Aggregates Composed of a Mixture of 175 and 475 nm Particles Made Using SDS pHEMA particle aggregates were prepared from mixtures of 475 nm and 175 nm PHEMA particles. The particles were prepared using the surfactant SDS as previously described.

Figure 21:
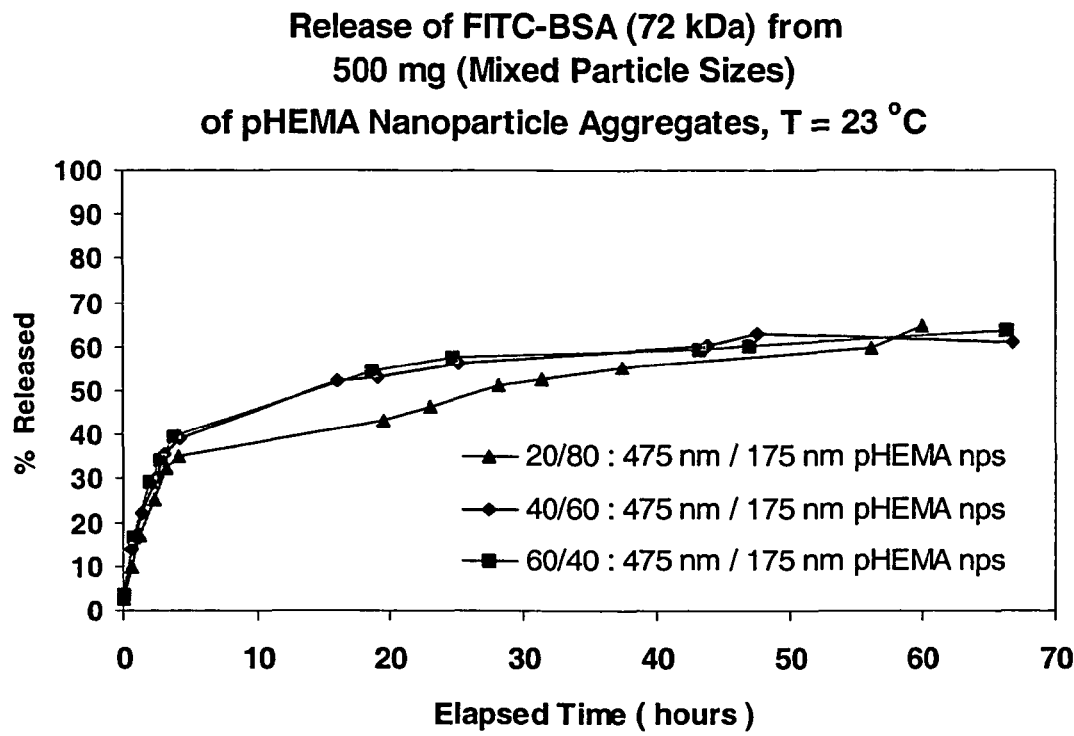
FIG. 21 is a plot showing the release of FITC-BSA (72 kDa) from aggregates produced from dispersions of SDS-stabilized pHEMA particles of different sizes injected in PBS at room temperature.
Figure 22:
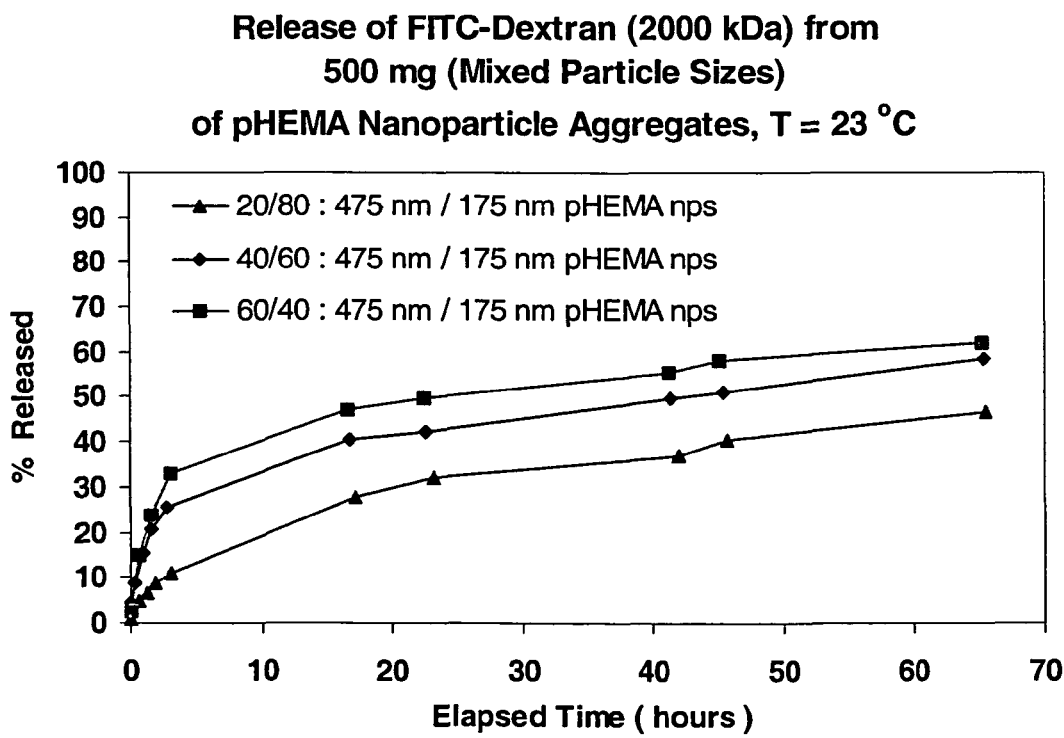
FIG. 22 is a plot showing the release of FITC-Dextran (2000 kDa) from aggregates produced from dispersions of SDS-stabilized pHEMA particles of different sizes injected in PBS at room temperature.

Using a Harvard Model 4400 Syringe Pump, a 10 mL syringe, 22-gauge needle, an infusion rate of 1 mL/min, 500 mg of PHEMA particle aggregates with compositions of 20/80, 40/60 and 60/40 : 475 nm and 175 nm pHEMA particles (respectively) containing either 10 mg FITC-BSA or 10 mg FITC-Dex were prepared. Five milliliters of the 100 mg/mL PHEMA particle dispersion mixture were combined with a pre-weighed aliquot of the FITC-labled macromolecule and the dispersion was injected into. PBS at room temperature. The rates of release and concentrations of the FITC labeled macromolecules were determined as above. The results are shown in FIGS. 21 and 22.

Figure 23:
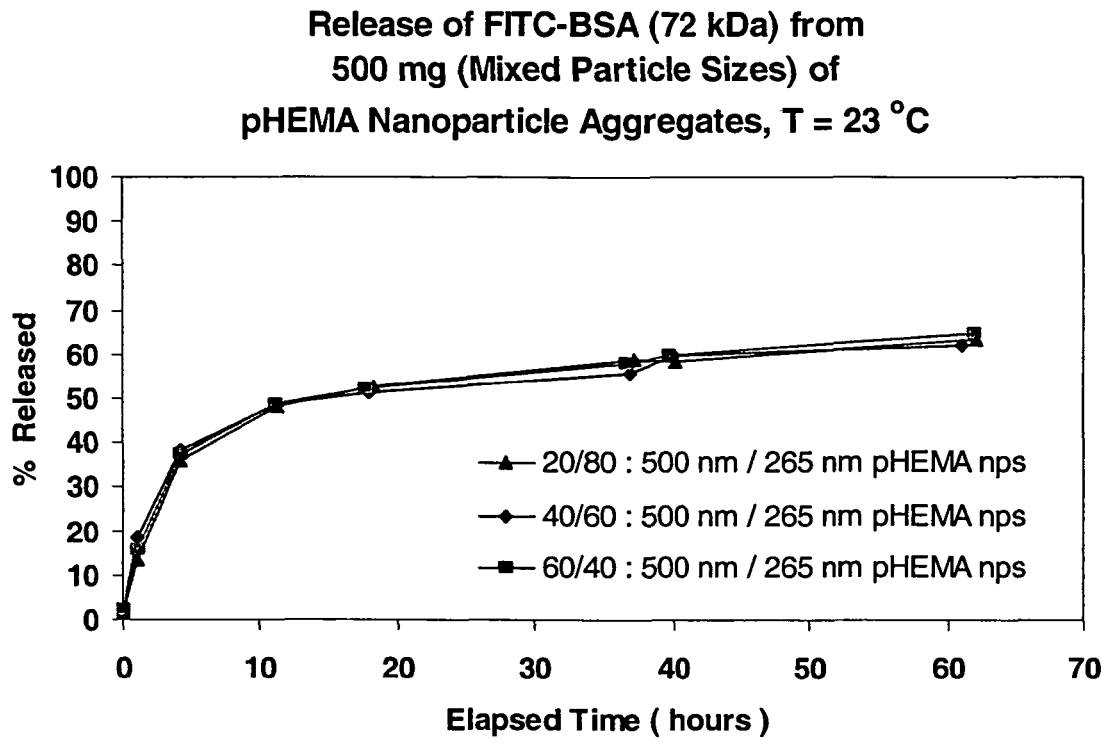
FIG. 23 is a plot showing the release of FITC-BSA (72 kDa) from aggregates produced from dispersions of DSS-stabilized PHEMA particles of different sizes injected in PBS at room temperature.
Figure 25:
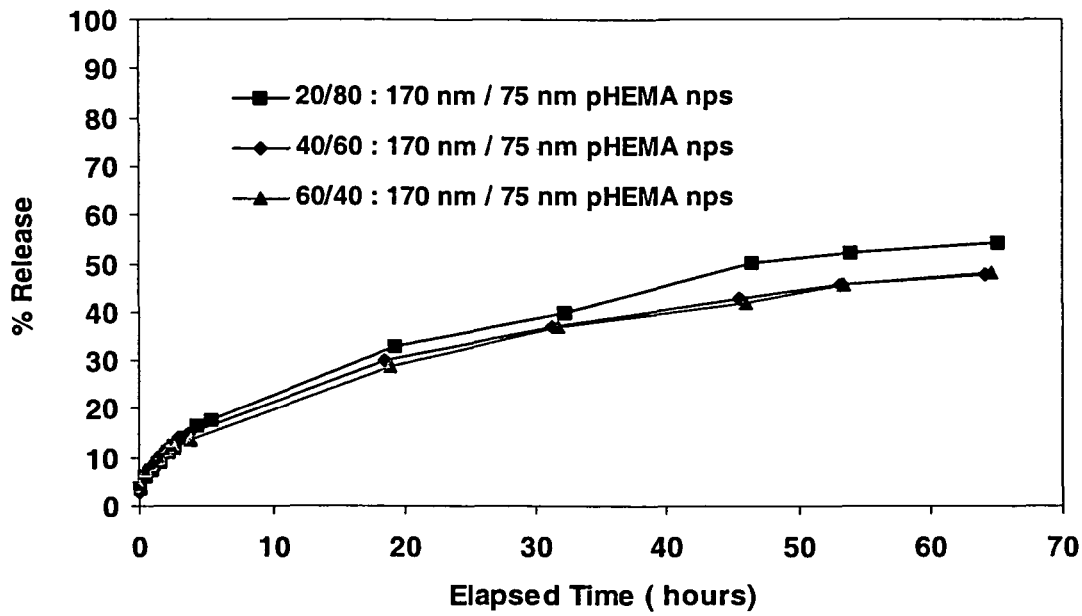
FIG. 25 is a plot showing the release of FITC-BSA (72 kDa) from aggregates produced from dispersions of SDS-stabilized pHEMA particles of different sizes injected in PBS at room temperature.
Figure 26:
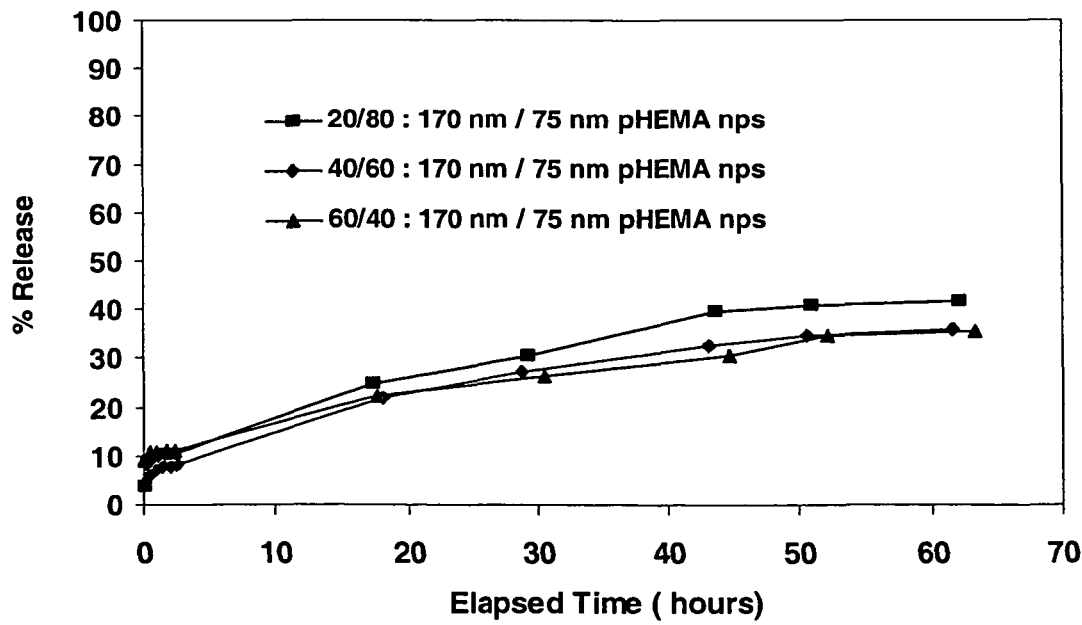
FIG. 26 is a plot showing the release of FITC-Dextran (2000 kDa) from aggregates produced from dispersions of SDS-stabilized pHEMA particles of different sizes injected in PBS at room temperature.

The FITC-Dex shows differences in release profiles relative to the three mixtures of particles utilized in making the hydrogel aggregates. The relative release rates for this macromolecule is in descending order, 60/40>40/60>20/80. The rate of release of FITC-Dex from the aggregate composed of a 20/80 mixture of pHEMA particles is slower than that observed for the pHEMA particle aggregates produced using one size of particles as shown in FIGS. 23 and 25. Each of the aggregates produced using mixtures of particles shown in FIG. 22 exhibit a slower release profile for FITC-Dex than the smaller FITC-BSA. FIG. 21 shows a large burst release for FITC-BSA regardless of the mixture of-particles used in making the aggregates and there is little difference in the release profile between the three mixtures used, indicating that the size of the particles used in making the aggregates were too large for this particular macromolecule.

Example 30

Figure 24:
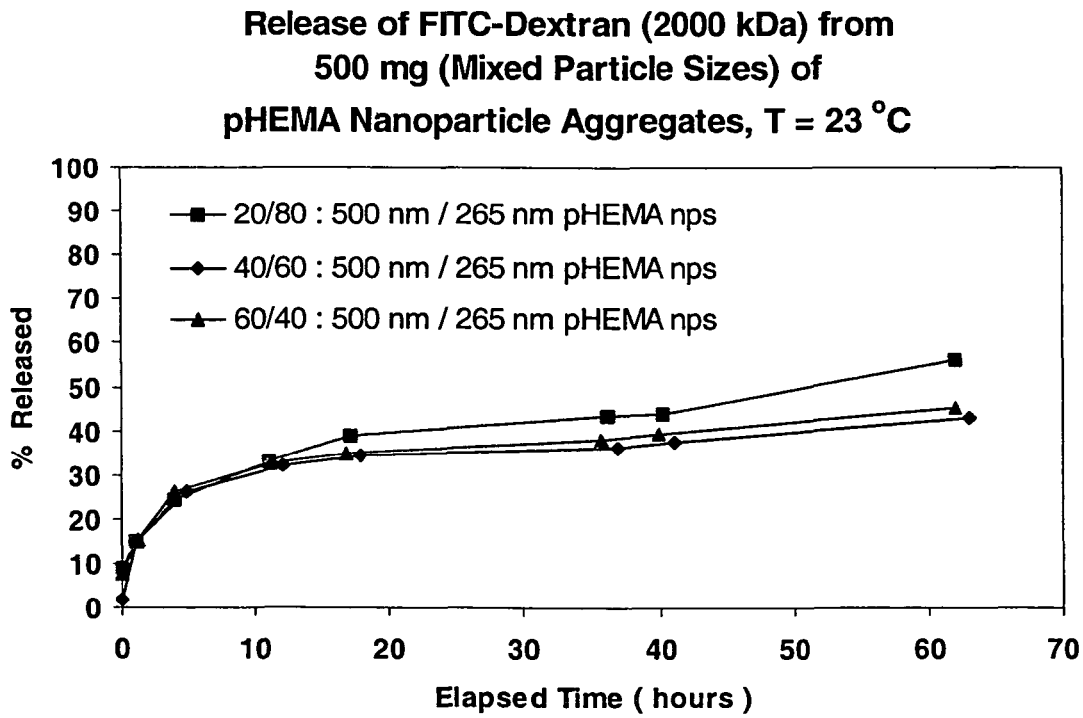
FIG. 24 is a plot showing the release of FITC-Dextran (2000 kDa) from aggregates produced from dispersions of DSS-stabilized pHEMA particles of different sizes injected in PBS at room temperature.

Release of Macromolecules from PHEMA Particle Aggregates Composed of a Mixture of 265 and 500 nm Particles Made Using DSS pHEMA particle aggregates were prepared from mixtures of 500 nm and 265 nm pHEMA particles. The particles were prepared using the surfactant DSS as previously described. Using a Harvard Model 4400 Syringe Pump, a 10 mL syringe, 22-gauge needle, an infusion rate of 1 mL/min, 500 mg PHEMA particle aggregates with compositions of 20/80, 40/60 and 60/40 500 nm and 265 nm PHEMA particles containing either 10 mg FITC-BSA or 10 mg FITC-Dex were prepared. Five milliliters of a 100 mg/mL (500 nm or 265 nm) pHEMA particle dispersion mixture were combined with a pre-weighed aliquot of the FITC-labeled macromolecule and the dispersion was injected into PBS at room temperature. The rates of release and concentrations for the FITC labeled macromolecules were determined as above. The results are shown in FIGS. 23 and 24.

The release profiles for FITC-BSA show little difference from one aggregate to another. All three mixtures used in the aggregate gave a 40% burst release of FITC-BSA within the first 5 to 6 hours and then slowing to pseudo zero order release from 20 through 60 hours. Again, FITC-Dex was released at a slower rate than FITC-BSA.

Example 31

Figure 27:
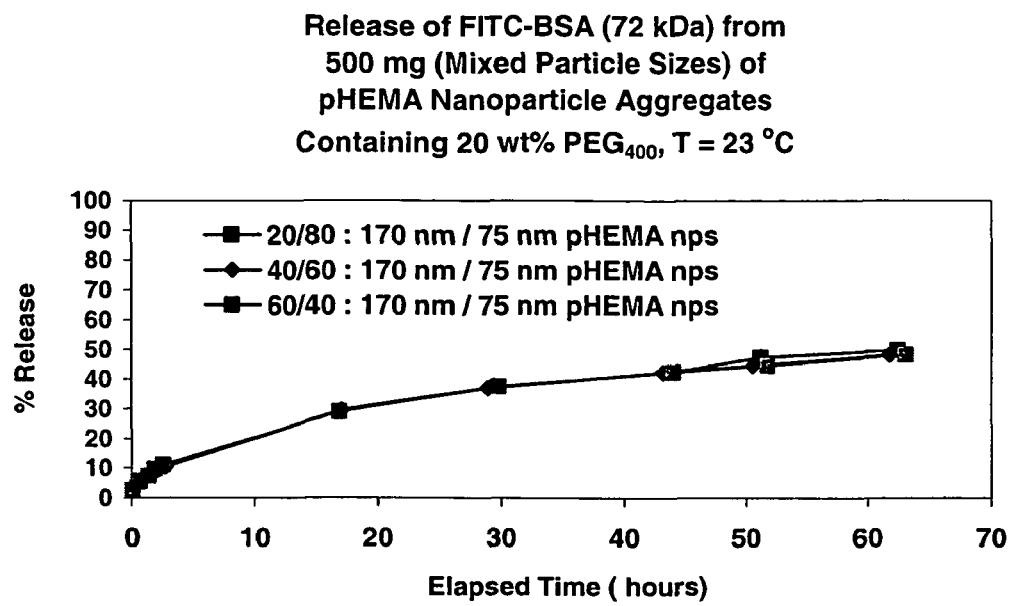
FIG. 27 is a plot showing the release of FITC-BSA (72 kDa) from aggregates produced from dispersions of SDS-stabilized pHEMA particles of different sizes containing 20 wt % polyethylene glycol 400 injected in PBS at room temperature.
Figure 28:
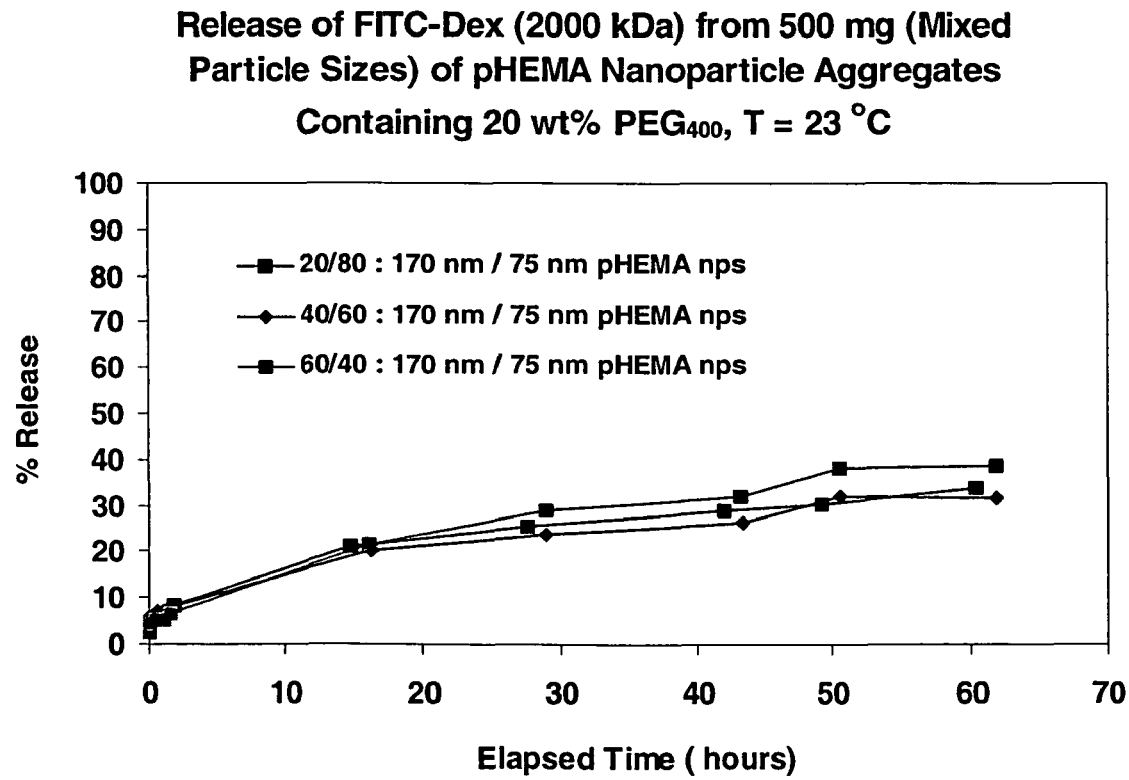
FIG. 28 is a plot showing the release of FITC-Dextran (2000 kDa) from aggregates produced from dispersions of SDS-stabilized pHEMA particles of different sizes containing 20 wt % polyethylene glycol 400 injected in PBS at room temperature.
Figure 29:
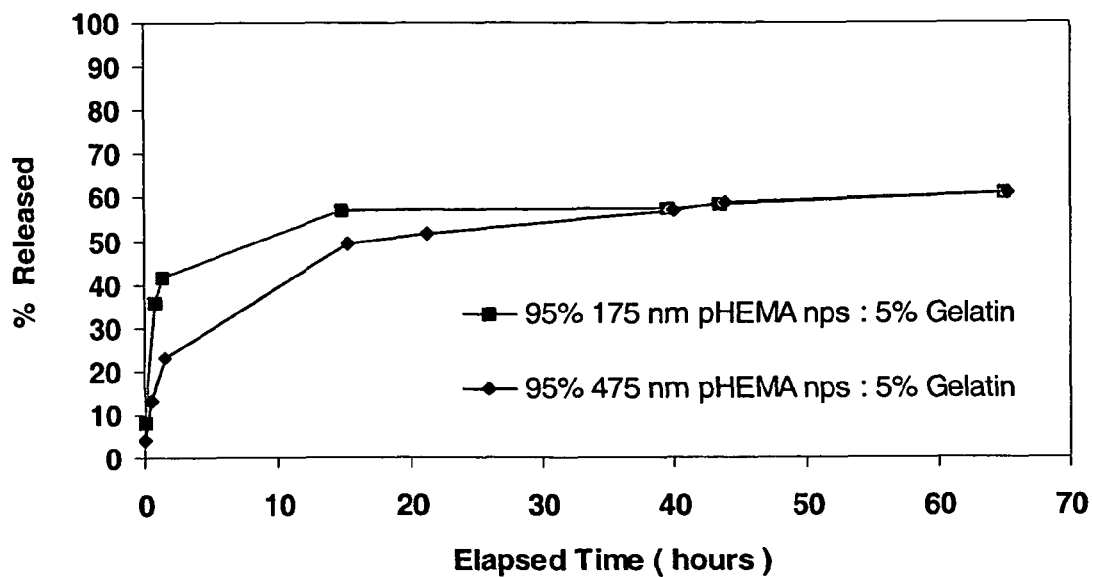
FIG. 29 is a plot showing the release of FITC-BSA (72 kDa) from aggregates produced from dispersions of SDS-stabilized pHEMA particles of different sizes containing 5 wt % gelatin injected in PBS at room temperature.

Release of Macromolecules from pHEMA Particle Aggregates Composed of a Mixture of 170 nm and 75 nm pHEMA Particles Made Using SDS pHEMA particle aggregates were prepared from mixtures of 170 nm and 75 nm pHEMA particles. The particles were prepared using the surfactant SDS as previously described. Using a Harvard Model 4400 Syringe Pump, a 10 mL syringe, 22-gauge needle, an infusion rate of 0.5 mL/min, 500 mg PHEMA particle aggregates with compositions of 20/80, 40/60 and 60/40: 170 nm and 75 nm pHEMA particles containing either 10 mg FITC-BSA or 10 mg FITC-Dex were prepared. Six and eight tenths milliliters of 74 mg/mL (170 nm or 75 nm) pHEMA particle dispersion mixtures were combined with a pre-weighed aliquot of the FITC-labeled macromolecule and the dispersion was injected into PBS at room temperature. The rate of release of the FITC labeled macromolecules was determined using UV-Vis analysis and concentrations were determined as above. The results are shown in FIGS. 27 and 28.

Figure 14:
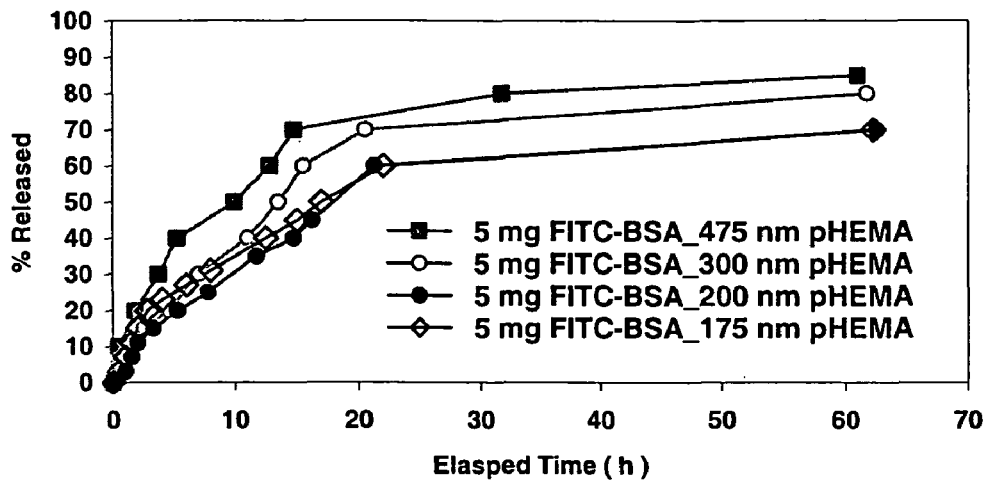
FIG. 14 is a plot showing the release of 5 mg FITC-BSA (72 kDA) from a series of 500 mg aggregates made from PHEMA particles of various diameters injected into PBS at room temperature.
Figure 15:
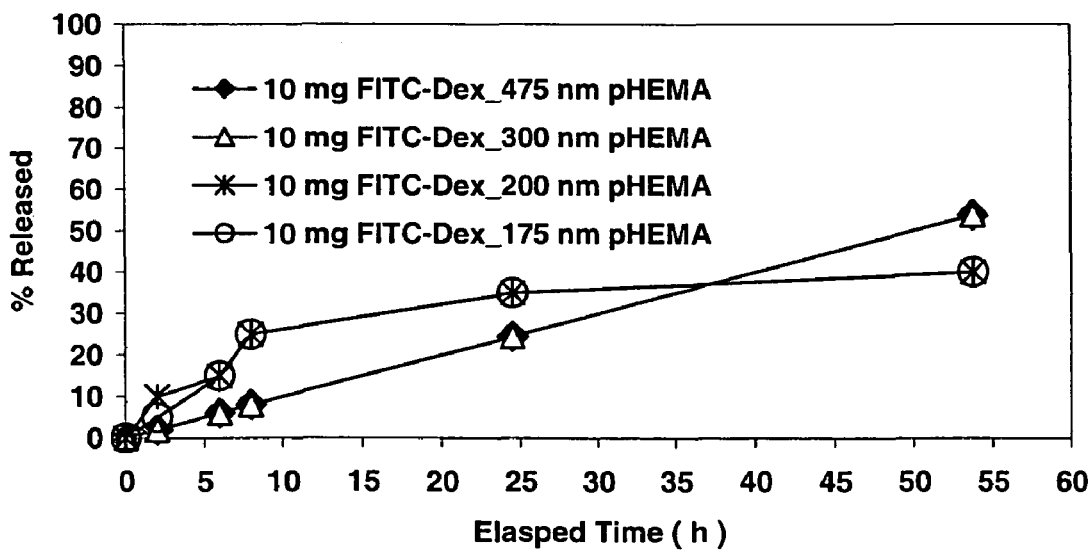
FIG. 15 is a plot showing the release of 10 mg FITC-Dextran (2000 kDa) from a series of 500 mg aggregates made from PHEMA particles of various diameters injected into PBS at room temperature.
Figure 16:
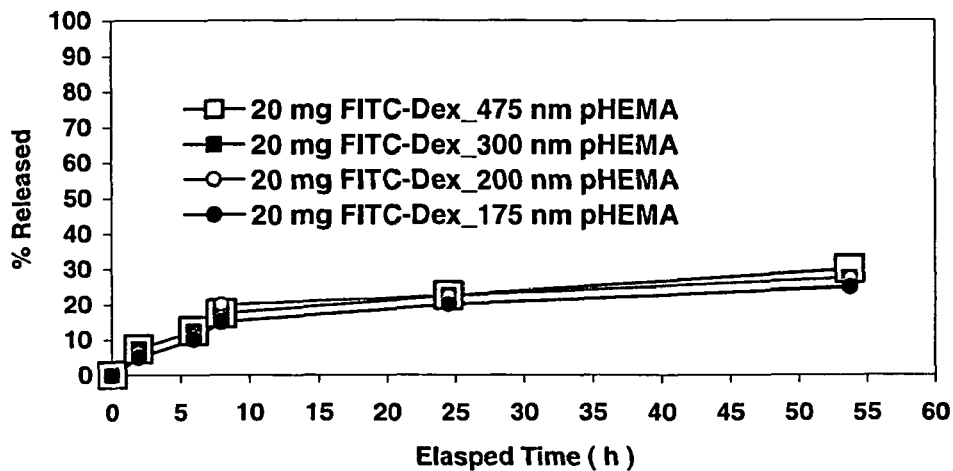
FIG. 16 is a plot showing the release of 20 mg FITC-Dextran (2000 kDa) from a series of 500 mg aggregates made from pHEMA particles of various diameters injected into PBS at room temperature.
Figure 17:
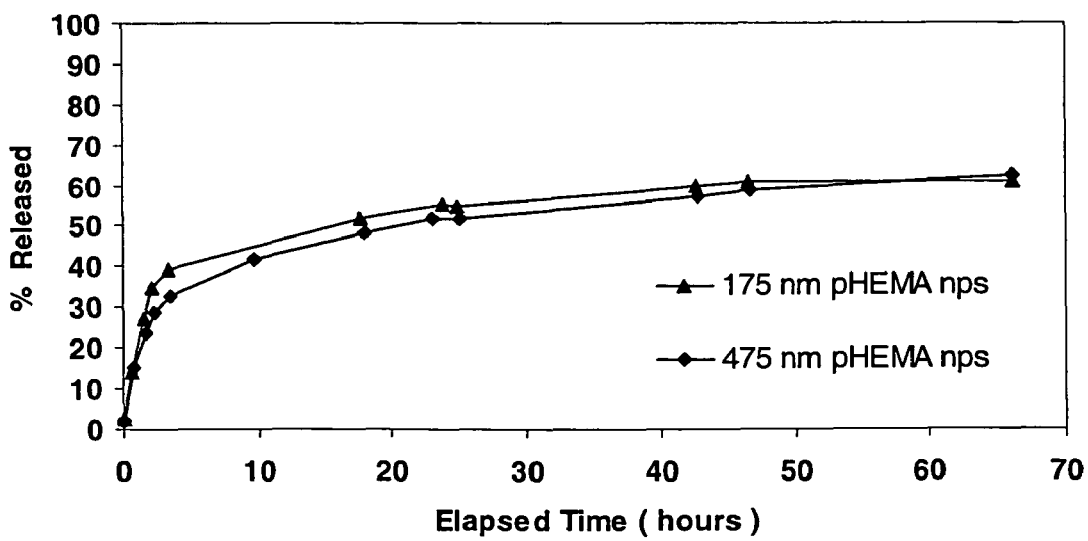
FIG. 17 is a plot showing the release of FITC-BSA (72 kDa) from aggregates produced from dispersions of SDS-stabilized particles of various sizes injected in PBS at room temperature.

The FITC-BSA shows differences in release profiles relative to the three mixtures of particles used to make the aggregates. The relative release rates for this macromolecule is in descending order, 20/80>40/60>60/40. The rate of release of FITC-BSA from the aggregate composed of a 60/40 mixture of 170 nm and 75 nm PHEMA particles is slower than that observed for the PHEMA particle aggregates produced using one size of particles as shown in FIG. 14 (i.e., 175 nm particles). Further, the burst release over the first six hours was less and the release profile was slower from the aggregates composed of a mixture of 170 nm and 75 nm particles than the burst release and the release profiles from the aggregates produced using a mixture of 475 and 175 nm particles and a mixture of the 500 and 265 nm particles shown in FIGS. 19 and 20, respectively. Similarly, the FITC-Dex exhibits a lower burst release (Table 11) and slower release profile from the aggregates composed of a mixture of the relative small sized particles compared to the aggregates produced using mixtures of larger particles. However, the release rates follow a different trend with respect to the weight ratio compositions of the relative sizes used in preparing the injected dispersions than that previously (Example 29).

Example 32

Release of Macromolecules from PHEMA Particles Aggregates Containing Polyethylene Glycol 400 pHEMA particle aggregates were prepared with 20 wt % polyethylene glycol 400 in the particle dispersions prior to injection. The particles were prepared using the surfactant SDS as previously described. Using a Harvard Model 4400 Syringe Pump, a 10 mL syringe, 16-gauge needle, an injection rate of 0.5 mL/min, 500 mg PHEMA particle aggregates composed of 20/80, 40/60 and 60/40 170 nm and 75 nm pHEMA particles containing either 10 mg FITC-BSA or 10 mg FITC-Dex and 100 mg of polyethylene glycol 400 were prepared. Six and eight tenths milliliters of 74 mg/mL (170 nm or 75 nm) pHEMA particle dispersion mixtures were combined with a pre-weighed aliquot of FITC-labeled macromolecule and polyethylene glycol 400 and the dispersion was injected into PBS at room temperature. The release rates of FITC labeled macromolecules were determined using UV-VIS analysis and concentrations were determined as above. The results are shown in FIGS. 27 and 28.

The aggregates containing the polyethylene glycol showed a much smaller burst release of FITC-BSA and FITC Dex (<12%) in the first six hours compared to the other aggregates containing a water-soluble adjuvant shown in the following example. The FITC-Dex was released at a slower rate than the FITC-BSA. However, very little differences in the release rates for both FITC-BSA and FITC-Dex were observed for each set of aggregates composed of different ratios of two particle sizes.

Example 33

Figure 30:
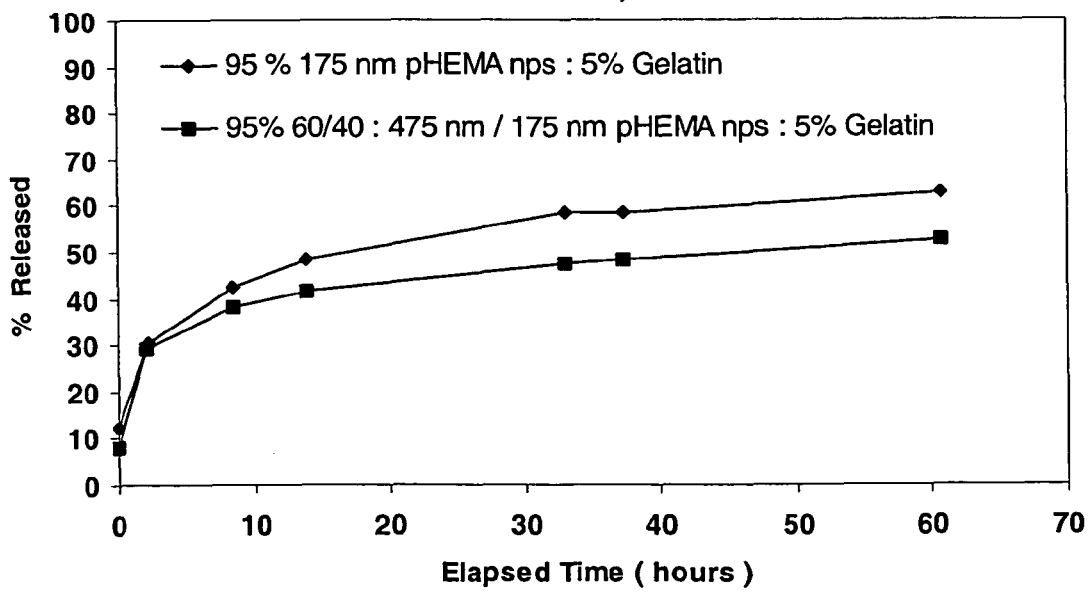
FIG. 30 is a plot showing the release of FITC-Dextran (2000 kDa) from aggregates produced from dispersions of SDS-stabilized pHEMA particles of different sizes and mixtures of sizes containing 5 wt % gelatin injected in PBS at room temperature.
Figure 31:
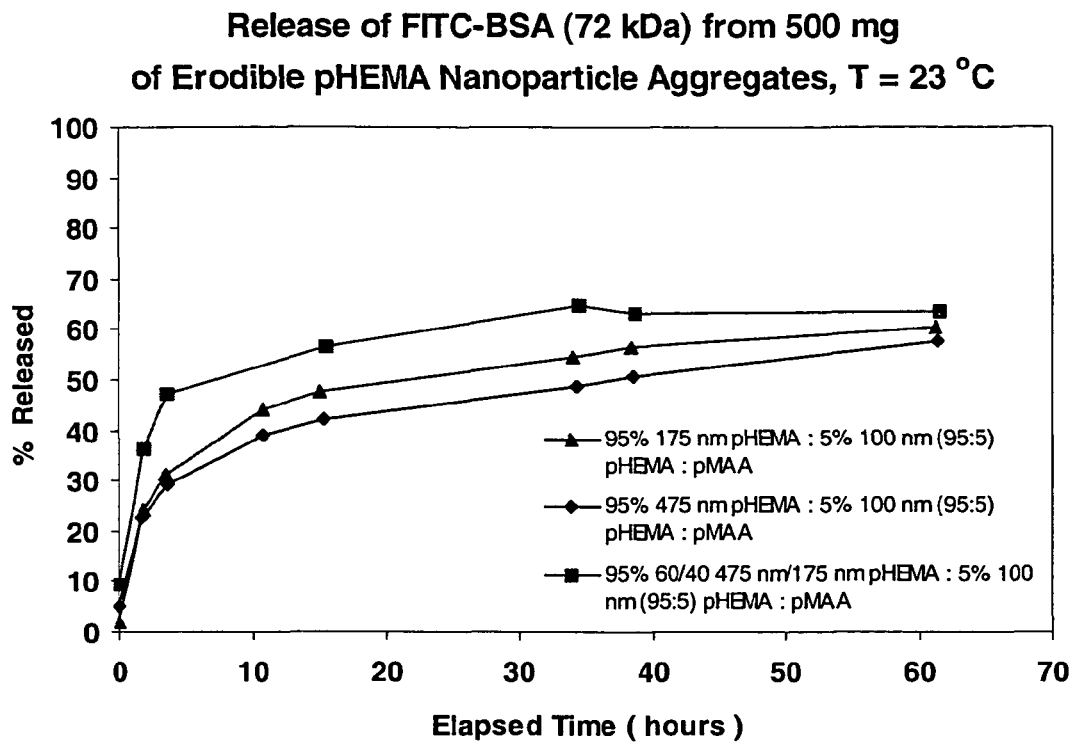
FIG. 31 is a plot showing the release of FITC-BSA (72 kDa) from degradable aggregates produced from dispersions of SDS-stabilized particles of different sizes containing 5 wt % (95:5) pHEMA/pMAA particles injected in PBS at room temperature.

Release of Macromolecules from PHEMA Particle Aggregates Composed of 5% Gelatin and 175 and 475 nm Particles Made Using SDS pHEMA particle aggregates were prepared using 5 wt % gelatin in the suspension system. The particles were prepared using the surfactant SDS as previously described. Five milliliters of a 100 mg/mL (475 nm or 175 nm) pHEMA particle dispersion mixture and 25 mg (5 wt % gelatin) were combined with a pre-weighed aliquot of the FITC-labeled macromolecule and the dispersion was injected into PBS at room temperature at a fixed rate. The rates of release and concentrations of the FITC labeled macromolecules were determined as above. The results are shown in FIGS. 30 and 31.

The aggregate containing the water-soluble gelatin provided a large burst release of FITC-BSA (>45%) in the first five hours. The FITC-Dex was released at a slower rate than the FITC-BSA, however, the rate of release of FITC-Dex was much faster than that observed with aggregates that did not contain a water-soluble additive.

Example 34

Figure 32:
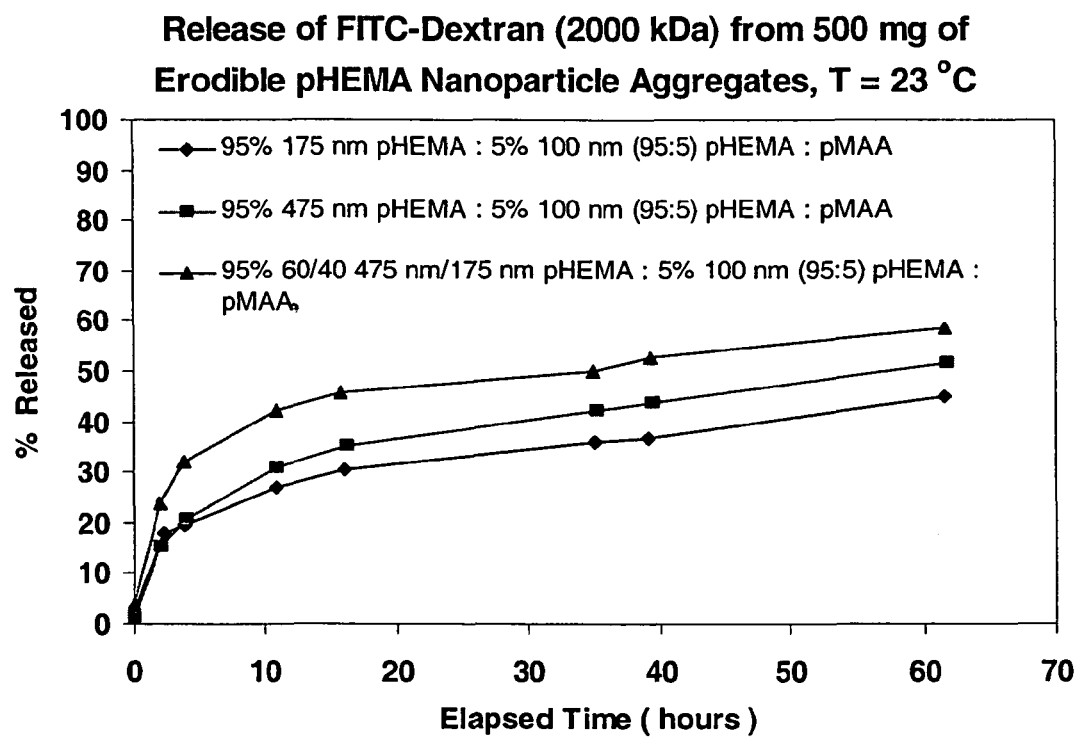
FIG. 32 is a plot showing the release of FITC-Dextran (2000 kDa) from degradable aggregates produced from dispersions of SDS-stabilized Particles of different sizes and mixtures of sizes containing 5 wt % (95:5) pHEMA/pMM particles injected in PBS at room temperature.
Figure 33:
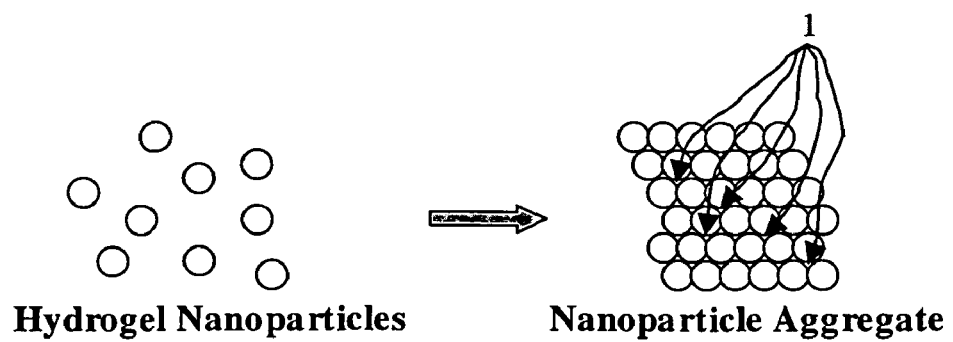
FIG. 33 is a schematic showing hydrogel particle aggregate formation.

Release of Macromolecules from Partially Erodible Aggregates Composed of 175 and 475 nm Particles Made Using SDS Aggregates composed of a mixture of 95% PHEMA and 5% pHEMA/pMAA particles were produced. MAA ionizes at physiological pH and the charged particles repel each other and dislodge from the aggregate over time. The rate of partial erosion is a function of the number of ionizing groups present in the aggregate. During partial erosion, the aggregate becomes more porous and the rate of release of an entrapped macromolecule is affected. The particles were prepared using the surfactant SDS as previously described. Five milliliters of a 100 mg/mL pHEMA particle dispersion mixture were combined with a pre-weighed aliquot of the FITC-labeled macromolecule and the dispersion was injected into PBS at room temperature at a fixed rate. The rates of release and concentrations for the FITC labeled macromolecules were determined as above. The results are shown in FIGS. 32 and 33.

Both FITC-BSA and FITC-Dex exhibit faster release profiles from the partially erodible aggregates than from non-erodible aggregates. Again, FITC-Dex is released at a slower rate because of its size. All the release profiles for both FITC-BSA and FITC-Dex show pseudo zero order release kinetics.

Example 35

Loading Efficiency and Burst Release from Macromolecules Incorporated into Particle Aggregates as a Function of Aggregate Composition Changes in the composition of particle dispersions effect how macromolecules are subsequently released from the subsequently formed aggregates. The rate of macromolecules release from the particle aggregates was found to be dependent on the size of the macromolecule, the size of the particles prior to the formation of the aggregates, particle sizes used in making the aggregates, the presence of additives which change the porosity of the aggregate, the surfactant present in the dispersion prior to injection as it effects the rate at which the aggregate forms, and whether the aggregate is erodible. Each of the above parameters and any combination of them will have a significant impact on the release of these materials. Table 11 summarizes the results for the previous examples.

TABLE 11

Comparisons of loading efficiency and burst release of macromolecules from pHEMA particle aggregates described in previous examples

| Composition of the 500 mg particle aggregate | % Loading of the 10 mg of FITC-BSA (72 kDa) | [1] % Release FITC-BSA Within the First 6 (h) | % Loading of the 10 mg FITC-Dex (2000 kDa) | [2] % Release FITC-Dex Within the First 6 (h) |
|---|---|---|---|---|
| [3] 475 nm pHEMA | 98% | 35% | 97% | 35% |
| [3] 175 nm pHEMA | 97% | 40% | 98% | 23% |
| [4] 500 nm pHEMA | 96% | 40% | 89% | 26% |
| [4] 265 nm pHEMA | 97% | 40% | 98% | 32% |
| [3] 20/80 Mix 475:175 nm pHEMA | 97% | 35% | 99% | 13% |
| [3] 40/60 Mix 475:175 nm pHEMA | 97% | 40% | 96% | 29% |
| [3] 60/40 Mix 475:175 nm pHEMA | 96% | 41% | 97% | 35% |
| [4] 20/80 Mix 500:265 nm pHEMA | 98% | 42% | 91% | 19% |
| [4] 40/60 Mix 500:265 nm pHEMA | 98% | 43% | 98% | 28% |
| [4] 60/40 Mix 500:265 nm pHEMA | 98% | 43% | 93% | 22% |
| [3] 20/80 Mix 170:75 nm pHEMA | 97% | 14% | 96% | 10% |
| [3] 40/60 Mix 170:75 nm pHEMA | 97% | 16% | 96% | 8% |
| [3] 60/40 Mix 170:75 nm pHEMA | 96% | 13% | 91% | 5% |
| [3] 20/80 Mix 170:75 nm pHEMA, 20% PEG$_{400}$ | 98% | 13% | 97% | 10% |
| [3] 40/60 Mix 170:75 nm pHEMA, 20% PEG$_{400}$ | 97% | 12% | 94% | 6% |
| [3] 60/40 Mix 170:75 nm pHEMA 20% PEG$_{400}$ | 98% | 13% | 96% | 6% |
| [3] 475 nm pHEMA 5 wt % Gelatin | 96% | 32% | N/A | N/A |
| [3] 175 nm pHEMA & 5 wt % Gelatin | 92% | 41% | 88% | 33% |
| [3] 60/40 Mix 475:175 nm pHEMA & 5 wt % Gelatin | N/A | N/A | 92% | 26% |

TABLE 11-continued

Comparisons of loading efficiency and burst release of macromolecules from pHEMA particle aggregates described in previous examples

| Composition of the 500 mg particle aggregate | % Loading of the 10 mg of FITC-BSA (72 kDa) | [1] % Release FITC-BSA Within the First 6 (h) | % Loading of the 10 mg FITC-Dex (2000 kDa) | [2] % Release FITC-Dex Within the First 6 (h) |
|---|---|---|---|---|
| [3] 95% 175 nm pHEMA:5% (95:5) 100 nm pHEMA pMAA | 98% | 36% | 97% | 20% |
| [3] 95% 475 nm pHEMA:5% (95:5) 100 nm pHEMA pMAA | 95% | 29% | 99% | 25% |
| [3] 95% 60/40 475:175 nm pHEMA:5% (95:5) 100 nm pHEMA pMAA | 91% | 43% | 96% | 33% |

[1] This data represent the normalized release of FITC-BSA (release of loaded FITC-BSA) from the aggregate to the supernatant (PBS) at 25 Celsius.
[2] This data represents the normalized release of FITC-Dex (release of loaded FITC-Dex) from the aggregate to the supernatant (PBS) at 25 Celsius.
[3] The pHEMA particles were synthesized using SDS as the surfactant.
[4] The pHEMA particles were synthesized using DSS as the surfactant.

Table 11 shows a comparison of the relative loading efficiencies observed with the various PHEMA particle aggregates as well as the initial burst release observed within the first 6 hours. In general, larger macromolecules show a correlation between its size and release profiles for the given systems relative to particle sizes used in the study. FITC-BSA was found to be released at faster rates from aggregates prepared using various particle sizes used and this would indicate that for smaller molecular weight compounds, smaller particles should be used to achieve long term release profiles.

CONCLUSION

Those skilled in the art will recognize that, while specific embodiments and examples have been described, various modifications and changes may be made without departing from the scope of this invention.

For example, it will be appreciated that this invention relates to methods of formation of shape-retentive aggregates and to uses of the aggregates so formed. The methods involve complex interactions of a wide range of factors that may affect the chemical and physical characteristics of the shape-retentive aggregate formed. In addition to those factors expressly discussed herein, other such factors may become apparent to those skilled in the art based on the disclosures herein. The application of such additional factors of variations in the factors and of combinations of factors are all within the scope of this invention.

Similarly, the methods of this invention will have a vast range of applications. While a number of such applications have been described above, other applications will become apparent to those skilled in the art based on the disclosures herein. All such applications that involve the methods of this invention to form a shape-retentive gel aggregate are within the scope of this invention.

Other embodiments are contained within the claims that follow.

What is claimed:

1. A method for forming a shape-retentive aggregate of gel particles, comprising:
providing a suspension system comprising a plurality of gel particles, the particles having an average diameter of less than about 955 nanometers, wherein the gel particles have a first absolute zeta potential and are made in a polymerization system by adding from 0.1 to 10 mol percent of a surfactant to a monomer, or two or more different monomers, wherein the monomer(s) are selected from the group consisting of a 2-alkenoic acid, a hydroxy(2C-4C)alkyl 2-alkenoate, a hydroxy(2C-4C)alkoxy(2C-4C)alkyl 2-alkenoate, a (1C-4C)alkoxy(2C-4C)alkoxy(2C-4C)alkyl 2-alkenoate and a vicinyl epoxy(1C-4C)alkyl 2-alkenoate and a combination of two or more thereof, in a polar liquid or a mixture of polar liquids, wherein the polar liquid or at least one of the two or more polar liquids comprise(s) one or more hydroxyl groups; and,
introducing the suspension system into a receiving medium, which after introduction, the gel particles acquire a second absolute zeta potential which is lower (closer to zero) than the first absolute zeta potential whereupon the gel particles coalesce into a shape-retentive aggregate that maintains indefinitely a shape and the particles of the aggregate are held together by non-covalent bond physical forces comprising hydrophobic-hydrophilic interactions and hydrogen bonds.

2. The method of claim 1, wherein the gel particles are at a concentration of from about 1 to about 500 mg wet weight/mL in the suspension system.

3. The method of claim 2, wherein the gel particles are at a concentration of from about 25 to about 250 mg wet weight/mL in the suspension system.

4. The method of claim 1 wherein the plurality of gel particles is of one size, one or more chemical compositions and a narrow polydispersivity.

5. The method of claim 1, wherein the plurality of gel particles is of two or more different sizes, the composition of each different size being the same as, or different than, the composition of each of the other different sizes, all sizes being of narrow polydispersivity.

6. The method of claim 1, wherein the plurality of gel particles comprises one or more chemical compositions and broad polydispersivity.

7. The method of claim 5, wherein the plurality of gel particles are at a concentration in the suspension system that results in cluster formation.

8. The method of claim 7, wherein the concentration of gel particles in the suspension system is from about 300 mg wet weight/mL to about 500 mg wet weight/mL.

9. The method of claim 1, wherein providing a suspension system comprises mixing together preformed dry gel particles, the liquid(s) and the surfactant.

10. The method of claim 1, wherein the suspension is introduced into the receiving medium through an orifice.

11. The method of claim 10, wherein the orifice comprises a hollow needle selected from the group consisting of 10 gauge to 30 gauge needles.

12. The method of claim 11, wherein the hollow needle is selected from the group consisting of 15 gauge to 27 gauge needles.

13. The method of claim 1, wherein the selected introduction rate is from about 0.05 ml/minute to about 15 ml/minute.

14. The method of claim 13, wherein the selected introduction rate is from about 0.25 ml/minute to about 10 ml/minute.

15. The method of claim 1, wherein the receiving, medium is an in vivo medium.

16. The method of claim 15, where the in vivo medium comprises a bodily tissue.

17. The method of claim 16, wherein the bodily tissue is selected from the group consisting of epithelium, connective, muscle and nerve.

18. The method of claim 17, wherein the connective tissue is selected from the group consisting of blood, bone and cartilage.

19. The method of claim 1, wherein the monomer(s) are selected from the group consisting of acrylic acid, methacrylic acid, 2-hydroxyethyl acrylate, 2-hydroxyethylmethacrylate, diethyleneglycol monoacrylate, diethyleneglycol monomethacrylate, 2-hydroxypropyl acrylate, 2-hydroxypropyl methyacrylate, 3-hydroxypropyl acrylate, 3-hydroxypropyl methacrylate, dipropylene glycol monoacrylate, dipropylene glycol monomethacrylate, gylcidyl methacrylate, 2,3-dihydroxypropyl methacrylate, glycidyl acrylate and glycidyl methacrylate and a combination of two or more thereof.

20. The method of claim 19, wherein the monomer(s) are selected from the group comprising 2-hydroxyathyl methacrylate, 2-hydroxypropyl methacrylate, 3-hydroxypropyl methacrylate, and a combination of two or more thereof.

21. The method of claim 1, wherein the liquid(s) are selected from the group consisting of water, a (1C-10C) alcohol, a (2C-8C)polyol, a (1C-4C)alkyl ether of a (2C-8C) polyol, a (1C-4C)acid ester of a (2C-8C)polyol; a hydroxy-terminated polyethylene oxide, a polyalkylene glycol and a hydroxy(2C-4C)alkyl ester of a mono, di- or tricarboxylic acid.

22. The method of claim 21, wherein the liquid(s) are selected from the group consisting of water, methanol, ethanol, isopropyl alcohol, ethylene glycol, diethylene glycol, triethylene glycol, polyethylene glycol 200-600, propylene glycol, dipropylene glycol, 1,4-butanediol, 2,3-butanediol, 1,6-hexanediol, 2,5-hexanediol, ethylene glycol monomethyl ether, ethylene glycol monoethyl ether, methylcellosolve ether, ethylene glycol monoacetate, propylene glycol monomethyl ether, glycerine, glycerol monoacetate, tri(2-hydroxyethyl)citrate, di(hydroxypropyl)oxalate, glycerine, glyceryl monoacetate, glyceryl diacetate, and glyceryl monobutyrate.

23. The method of claim 22, wherein the liquid is water.

24. The method of claim 1, comprising adding from about 0.1 to about 15% mol percent of a cross-linking agent to the polymerization system which results in cross-linking of the polymer strands.

25. The method of claim 24, wherein the cross-linking agent is selected from the group consisting of ethylene glycol diacrylate, ethylene glycol dimethacrylate, 1,4-dihydroxybutane dimethacrylate, diethylene glycol dimethacrylate, propylene glycol dimethacrylate, diethylene glycol dimethacrylate, dipropylene glycol dimethacrylate, diethyleneglycol diacrylate, dipropylene glycol diacrylate, divinyl benzene, divinyltoluene, diallyl tartrate, diallyl malate, divinyl tartrate, triallyl melamine, N,N'-methylene bisacrylamide, diallyl maleate, divinyl ether, 1,3-diallyl 2-(2-hydroxyethyl) citrate, vinyl ally) citrate, allyl vinyl maleate, diallyl itaconate, di(2-hydroxyethyl) itaconate, divinyl sulfone, hexahydro-1,3,5-triallyltriazine, triallyl phosphite, diallyl benzenephosphonate, triallyl aconitate, divinyl citraconate, trimethyloipropane trimethacrylate and diallyl fumarate.

26. The method of claim 24, wherein the cross-linking agent is selected from the group consisting of alpha-hydroxy acid esters.

27. The method of claim 24, wherein the cross-linked polymer strands have an average molecular weight of from about 3,000 to about 2,000,000.

28. The method of claim 1, further comprising
adding one or more working substance(s) to the polar liquid(s) of the polymerization system prior to polymerization wherein, after polymerization, a portion of the working substance(s)-containing liquid is occluded by the gel particles to give working substance-containing gel particles and wherein the working substance is one or more of a biomedical agent, a pharmaceutical agent, or a pharmaceutical excipient.

29. The method of claim 28, wherein the working substance-containing gel particles occlude from about 0.1 to about 90 weight percent working substance-containing liquid.

30. The method of claim 1, further comprising adding one or more working substance(s) to the suspension system, wherein the working substance is one or more of a biomedical agent, a pharmaceutical agent, or a pharmaceutical excipient.

31. The method of claim 30, wherein, upon formation of the shape-retentive aggregate, from about 0.1 to about 90 weight percent of the working substance(s)-containing-liquid is entrapped with in the shape-retentive aggregate.

32. The method of any one of claims 28-31, wherein the working substance(s) comprise one or more biomedical agent(s), which may be the same or different.

33. The method of claim 32, wherein one or more of the biomedical agent(s) comprise(s) one or more pharmaceutical agent(s).

34. The method of claim 33, wherein the pharmaceutical agent(s) further comprises/comprise one or more pharmaceutically acceptable excipient(s).

35. The method of claim 33, wherein the pharmaceutical agent(s) comprises/comprise a peptide or a protein.

36. The method of claim 33, wherein the pharmaceutical agent(s) is/are useful for the treatment of cancer.

37. The method of claim 33, wherein the pharmaceutical agent(s) is/are useful for the treatment of coronary artery disease.

38. The method of claim 33, wherein the pharmaceutical agent(s) is/are useful for the treatment of respiratory diseases.

39. The method of claim 33, wherein the pharmaceutical agent(s) is/are useful for the treatment of infectious diseases.

40. The method of claim 33, wherein the pharmaceutical agent(s) is/are useful for the treatment of ocular disease.

41. The method of claim 33, wherein the pharmaceutical agent(s) is/are growth factors.

42. The method of claim 33, wherein the biomedical agent(s) comprises/comprise one or more tissue-growth scaffold materials.

43. The method of claim 33, wherein the biomedical agent(s) comprises/comprise cosmetic tissue enhancement substances.

44. The method of claim 1, wherein the size of the gel particles is from about 10 to about 800 nanometers in diameter.

45. The method of claim 1, wherein the shape-retentive aggregate is elastic.

46. The method of claim 1, wherein from 1.27 to about 2.77 mole percent of surfactant is added to the liquid(s).

* * * * *